(12) United States Patent
Kay et al.

(10) Patent No.: US 11,759,546 B2
(45) Date of Patent: Sep. 19, 2023

(54) IMPLANTABLE OBJECTS, GUIDING DEVICES, AND METHODS OF USE THEREOF

(71) Applicant: RevBio, Inc., Lowell, MA (US)

(72) Inventors: George W. Kay, Sharon, MA (US); Brian J. Hess, Charlestown, MA (US)

(73) Assignee: RevBio, Inc., Lowell, MA (US)

( * ) Notice: Subject to any disclaimer, the term of this patent is extended or adjusted under 35 U.S.C. 154(b) by 292 days.

(21) Appl. No.: 15/778,520

(22) PCT Filed: Nov. 23, 2016

(86) PCT No.: PCT/US2016/063631
§ 371 (c)(1),
(2) Date: May 23, 2018

(87) PCT Pub. No.: WO2017/091748
PCT Pub. Date: Jun. 1, 2017

(65) Prior Publication Data
US 2018/0344894 A1    Dec. 6, 2018

Related U.S. Application Data

(60) Provisional application No. 62/258,766, filed on Nov. 23, 2015.

(51) Int. Cl.
| | |
|---|---|
| A61C 8/00 | (2006.01) |
| A61L 24/04 | (2006.01) |
| A61C 1/08 | (2006.01) |
| A61B 17/17 | (2006.01) |
| A61C 8/02 | (2006.01) |
| A61B 17/32 | (2006.01) |
| A61B 17/58 | (2006.01) |

(Continued)

(52) U.S. Cl.
CPC ............... *A61L 24/04* (2013.01); *A61B 17/17* (2013.01); *A61B 17/32* (2013.01); *A61B 17/58* (2013.01); *A61B 17/84* (2013.01); *A61B 17/86* (2013.01); *A61B 90/39* (2016.02); *A61C 1/07* (2013.01); *A61C 1/084* (2013.01); *A61C 8/00* (2013.01); *A61C 8/0006* (2013.01); *A61C 8/0009* (2013.01); *A61C 8/0036* (2013.01); *A61C 8/0048* (2013.01); *A61C 8/0068* (2013.01); *A61C 13/225* (2013.01); *A61F 2/447* (2013.01); *A61F 2/4611* (2013.01); *A61B 17/7062* (2013.01); *A61B 2017/564* (2013.01);

(Continued)

(58) Field of Classification Search
CPC ...... A61C 8/0006; A61C 8/0036; A61L 24/04
See application file for complete search history.

(56) References Cited

U.S. PATENT DOCUMENTS 3,628,248 A * 12/1971 Kroder .................. A61K 6/891
433/175
5,372,503 A * 12/1994 Elia .......................... A61C 8/00
433/173

(Continued)

OTHER PUBLICATIONS

International Search Report and Written Opinion for International Application No. PCT/US1663631 dated Mar. 27, 2017.

(Continued)

*Primary Examiner* — Ralph A Lewis
(74) *Attorney, Agent, or Firm* — Lando & Anastasi, LLP

(57) ABSTRACT

Embodiments of the disclosure relate to implantable objects and guiding devices, as well as recipient site preparation instruments, bone-implantable materials, and methods of fabrication and use thereof.

19 Claims, 19 Drawing Sheets

Implantable object in situ

(51) Int. Cl.
*A61C 13/225* (2006.01)
*A61B 90/00* (2016.01)
*A61B 17/84* (2006.01)
*A61B 17/86* (2006.01)
*A61C 1/07* (2006.01)
*A61F 2/44* (2006.01)
*A61F 2/46* (2006.01)
*A61B 17/56* (2006.01)
*A61B 17/70* (2006.01)
*A61F 2/30* (2006.01)
*F16B 11/00* (2006.01)

(52) U.S. Cl.
CPC ....... *A61B 2090/3983* (2016.02); *A61C 8/005* (2013.01); *A61C 2008/0046* (2013.01); *A61F 2002/30433* (2013.01); *A61F 2002/30448* (2013.01); *A61F 2002/4687* (2013.01); *F16B 11/00* (2013.01)

(56) References Cited

U.S. PATENT DOCUMENTS

| | | | | |
|---|---|---|---|---|
| 5,562,450 | A * | 10/1996 | Gieloff | A61C 8/0036 433/201.1 |
| 6,696,073 | B2 * | 2/2004 | Boyce | A61L 31/005 424/443 |
| 8,232,327 | B2 * | 7/2012 | Garigapati | A61K 38/1875 523/116 |
| 2005/0273114 | A1 | 12/2005 | Novak | |
| 2008/0090207 | A1 * | 4/2008 | Rubbert | A61C 8/0036 433/171 |
| 2009/0061389 | A1 | 3/2009 | Lomicka et al. | |
| 2010/0203478 | A1 | 8/2010 | Rubbert | |
| 2010/0256758 | A1 | 10/2010 | Gordon et al. | |
| 2011/0034931 | A1 | 2/2011 | Sawatari et al. | |
| 2011/0125003 | A1 | 5/2011 | Reach | |
| 2011/0277931 | A1 * | 11/2011 | Garigapati | A61L 24/06 156/331.6 |
| 2012/0070802 | A1 * | 3/2012 | Woodward, III | G06F 19/00 433/175 |
| 2013/0131741 | A1 | 5/2013 | Kourtis et al. | |
| 2014/0287377 | A1 | 9/2014 | Salcedo et al. | |

OTHER PUBLICATIONS

Partial Search Report in European Patent Application No. 16869292.9 dated Jul. 4, 2019.
Extended European Search Report in European Patent Application No. 16869292.9 dated Oct. 16, 2019.
Office Action in European Patent Application No. 16869292.9 dated Sep. 3, 2020.

* cited by examiner

View of an implantable object designed for spine articular process fusion e.g. facet joint View of an implantable object designed for spine articular process fusion, e.g. facet joint

IMPLANTABLE OBJECTS, GUIDING DEVICES, AND METHODS OF USE THEREOF

CROSS REFERENCE TO RELATED APPLICATIONS

This application is a U.S. National Stage Application under 35 U.S.C. § 371 of International Application No. PCT/US2016/063631, filed Nov. 23, 2016, which claims priority to U.S. Provisional Application 62/258,766, filed Nov. 23, 2015. The entire contents of each of the foregoing applications are incorporated herein by reference.

FIELD

Embodiments of the disclosure relate to implantable objects and guiding devices, as well as recipient site preparation instruments, bone-implantable materials, and methods of fabrication and use thereof.

BACKGROUND

The placement of implants into bone is an active area of surgery involving the attachment of a bone fragment or device (i.e., a foreign object (e.g., screw, a rod, a plate, or other material) to bone. One goal of these procedures is to achieve osseointegration, in which the implant is attached directly onto or into the lamellar bone without an intervening fibrous tissue capsule. A successfully osseointegrated implant is held in place in the bone without significant motion (less than 20 microns) between the implant and bone surface, this resulting from sufficient bone surface in contact with the implant surface providing mechanical resistance to forces applied.

Placement of an implant into bone involves first preparing the implantation site by mechanical means, usually drilling or milling, in an effort to provide the site with appropriate geometric and mechanical characteristics to allow seating of the implant body at the desired site. However, the current methods of preparation, which are subtractive, often compromise the outcome by inflicting damage to the implantation site through removal of useful sound bone, resulting in weakening the surrounding tissue and an increased reliance on bone grafts. For these reasons, many implants are typically not available for patient populations susceptible to bone fracture or breakage, such as those with moderate to severe osteoporosis or other conditions leading to weakened bone.

Computed tomography (CT) scan data may be used in planning guided implant surgery and implant reconstruction. In the oral context, in absence of dentition, a physical radiographic guide resting on the soft tissues and fitted with radiopaque markers is included in the field of examination and used as a spatial reference. Radiographic data are then used to generate virtual models from which physical surgical guides and provisional restorations are fabricated. Two requirements for precision are required in order for an accurate placement of an implant: 1.) the stable fixation of a guide device during the radiographic exposure, and 2.) an accurate and stable placement of the guide into the surgical site at the time of implant insertion. Inaccuracies in these tasks make up the two greatest uncontrolled sources of significant clinical error in guided implant surgery today. Other challenges relating to current protocols include high expense, the time-consuming nature of the operative procedures, and risk of graft failure. As such, there exists a need for new implant methods and devices in that minimize damage caused to the patient during the preparation of the implant bed, as well as methods for placement of implants that use indexing techniques to improve surgical outcomes. Furthermore, the development of new bone-implantable compositions that structurally support bone and provide fixation or load bearing support to implantable objects, drives the need for new forms and methods to facilitate the placement of such implantable objects.

SUMMARY

The present disclosure features devices and materials for implantation of objects into implantation sites (e.g., bones). Implantable objects, guiding devices, recipient site preparation instruments, and bone implantable materials, as well as methods of use and fabrication and kits thereof are described.

In one aspect, the present disclosure features a kit comprising: 1) an implantable object that is substantially free of a thread and comprises a bone-engaging element (e.g., a macro-rough surface, longitudinal groove, flute, fin, post, or stud); and 2) a guiding device that provides positioning, reference, orientation or retention of an implantable object in a geometrically defined position to a bone (e.g., a host bone) at an implantation site. In some embodiments, the implantable object matches the size, shape, or other dimension of the implantation site and the implantable object comprises a smooth surface and a changing contour (e.g, to avoid a critical structure). In some embodiments, the implantable object is substantially free of a thread and comprises a bone-engaging element (e.g., a macro-rough surface, longitudinal groove, flute, fin, post, or stud). In some embodiments, the implantation site comprises a bone or bone socket (e.g., tooth socket).

In some embodiments, the implantable object is custom produced (e.g., based on CAT scan data), e.g., to match the shape of the implant bed. In some embodiments, the implantable object fits within the inner wall of the metaphysis or diaphysis cortex or is about the size and/or shape of a tooth root. In some embodiments, the implantable object is between about 0.1 mm and about 50 mm in diameter (e.g., about 0.5 mm to about 25 mm or about 1 mm to about 10 mm). In some embodiments, the implantable object comprises a port or opening.

In some embodiments, the guiding device provides reference, position, orientation or retention of an implantable object in a geometrically defined position to a bone (e.g., a host bone) at an implantation site. In some embodiments, the guiding device comprises an opening for access to the space between the implantable object and an adhesive composition. In some embodiments, the guiding device is substantially rigid. In some embodiments, the guiding device is capable of release from the implantation site. In some embodiments, the guiding device comprises a naturally occurring polymer (e.g., collagen, a modified collagen, or gelatin) or a synthetic polymer (e.g., rubber, elastomer, PGA, or PLGA).

In some embodiments, the guiding device comprises at least 2, at least 3, at least 4, at least 5, or at least 6 components (e.g., implantable components). In some embodiments, the component (e.g., implantable component) is implanted fully in the bone. In some embodiments, the component (e.g., implantable component) is implanted partially in the bone.

In some embodiments, the kit further comprises a recipient site preparation instrument that acts subtractively or additively toward an implantation site to prepare said site for placement of an implantable object. In some embodiments, the implantation site comprises a bone or bone socket (e.g., tooth socket).

In some embodiments, a component of the RSP instrument (e.g., the RSP head) is custom produced (e.g., based on CAT scan data), e.g., to match the shape of the implantable object. In some embodiments, a component of the RSP instrument (e.g., the RSP head) fits within the inner wall of the metaphysis or diaphysis cortex or is about the size and/or shape of a tooth root. In some embodiments, a component of the RSP instrument (e.g., the RSP head) exhibits a displacement swing amplitude from about 2 μm to about 2 mm. In some embodiments, the direction of the displacement of a component of the RSP instrument (e.g., the RSP head) is aligned to be parallel with the path of insertion of the implantable object. In some embodiments, a component of the RSP instrument (e.g., the RSP head) exhibits a subsonic vibration (e.g., less than about 60 Hz), a sonic vibration (e.g., between about 60 Hz to about 25,000 Hz), or an ultrasonic vibration is between about 0.1 mm and about 50 mm in diameter (e.g., about 0.5 mm to about 25 mm or about 1 mm to about 10 mm).

In some embodiments, the kit further comprises an adhesive composition comprising a multivalent metal salt and an acidic compound. In some embodiments, the adhesive composition comprises an acidic compound of Formula (I):

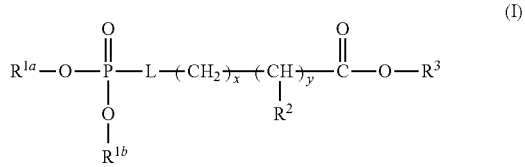

or a pharmaceutically acceptable salt thereof, wherein L is O, S, NH, or $CH_2$; each of $R^{1a}$ and $R^{1b}$ is independently H, optionally substituted alkyl, or optionally substituted aryl; $R^2$ is H, $NR^{4a}R^{4b}$, $C(O)R^5$, or $C(O)OR^5$; $R^3$ is H, optionally substituted alkyl, or optionally substituted aryl; each of $R^{4a}$ and $R^{4a}$ is independently H, $C(O)R^6$, or optionally substituted alkyl; $R^5$ is H, optionally substituted alkyl, or optionally substituted aryl; $R^6$ is optionally substituted alkyl or optionally substituted aryl; and each of x and y is independently 0, 1, 2, or 3; or Formula (II):

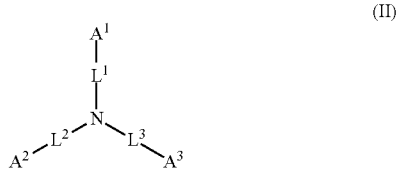

wherein each of $A^1$, $A^2$, and $A^3$ is independently selected from an acidic group (e.g., a carboxyl or phosphonyl); and each of $L^1$, $L^2$, and $L^3$ is independently bond, alkylene (e.g., $C_1$-$C_6$ alkylene), or heteroalkylene (e.g., $C_1$-$C_6$ heteroalkylene); or Formula (III):

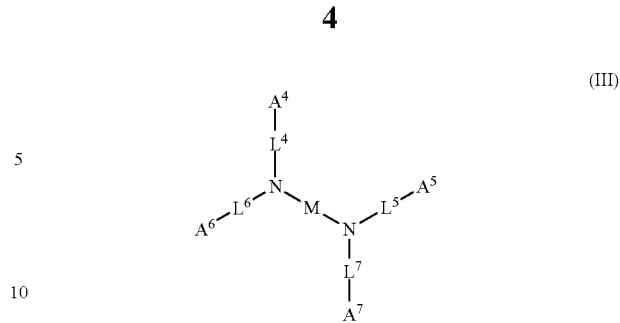

wherein each of $A^4$, $A^5$, $A^6$, and $A^7$ is independently an acidic group (e.g., a carboxyl or phosphonyl); each of $L^4$, $L^5$, $L^6$, and $L^7$ is independently bond, alkylene (e.g., $C_1$-$C_6$ alkylene), or heteroalkylene (e.g., $C_1$-$C_6$ heteroalkylene); and M is alkylene (e.g., $C_1$-$C_6$ alkylene) or heteroalkylene (e.g., $C_1$-$C_6$ heteroalkylene).

In another aspect, the present disclosure features a method for repairing a bone comprising placement of an implantable object at an implantation site, comprising (a) preparing the implantation site to receive the implantable object with a recipient site preparation instrument that matches the shape of the implantable object; (b) optionally applying an adhesive composition to the bone, to the implantable object or to both; (c) inserting the implantable object into implantation site in a desired orientation; and (d) allowing the adhesive composition to cure. In some embodiments, the implantable object matches the size, shape, or other dimension of the implantation site and the implantable object comprises a smooth surface and a changing contour (e.g, to avoid a critical structure). In some embodiments, the implantable object is substantially free of a thread and comprises a bone-engaging element (e.g., a macro-rough surface, longitudinal groove, flute, fin, post, or stud). In some embodiments, the implantation site comprises a bone or bone socket (e.g., tooth socket).

In some embodiments, the implantable object is custom produced (e.g., based on CAT scan data), e.g., to match the shape of the implant bed. In some embodiments, the implantable object fits within the inner wall of the metaphysis or diaphysis cortex or is about the size and/or shape of a tooth root. In some embodiments, the implantable object is between about 0.1 mm and about 50 mm in diameter (e.g., about 0.5 mm to about 25 mm or about 1 mm to about 10 mm). In some embodiments, the implantable object comprises a port or opening.

In some embodiments, the recipient site preparation instrument acts subtractively or additively toward an implantation site to prepare said site for placement of an implantable object. In some embodiments, the implantation site comprises a bone or bone socket (e.g., tooth socket). In some embodiments, a component of the RSP instrument (e.g., the RSP head) is custom produced (e.g., based on CAT scan data), e.g., to match the shape of the implantable object. In some embodiments, a component of the RSP instrument (e.g., the RSP head) fits within the inner wall of the metaphysis or diaphysis cortex or is about the size and/or shape of a tooth root. In some embodiments, a component of the RSP instrument (e.g., the RSP head) exhibits a displacement swing amplitude from about 2 μm to about 2 mm. In some embodiments, the direction of the displacement of a component of the RSP instrument (e.g., the RSP head) is aligned to be parallel with the path of insertion of the implantable object. In some embodiments, a component of the RSP instrument (e.g., the RSP head) exhibits a subsonic vibration (e.g., less than about 60 Hz), a sonic vibration (e.g., between about 60 Hz to about 25,000 Hz), or an ultrasonic vibration is between about 0.1 mm and about 50 mm in diameter (e.g., about 0.5 mm to about 25 mm or about 1 mm to about 10 mm).

In some embodiments, the adhesive composition comprises a multivalent metal salt and an acidic compound. In some embodiments, the adhesive composition comprises an acidic compound of Formula (I):

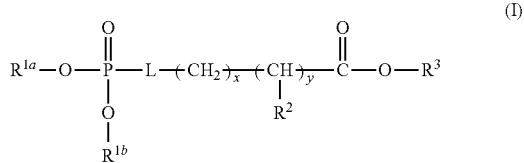

or a pharmaceutically acceptable salt thereof, wherein L is O, S, NH, or $CH_2$; each of $R^{1a}$ and $R^{1b}$ is independently H, optionally substituted alkyl, or optionally substituted aryl; $R^2$ is H, $NR^{4a}R^{4b}$, $C(O)R^5$, or $C(O)OR^5$; $R^3$ is H, optionally substituted alkyl, or optionally substituted aryl; each of $R^{4a}$ and $R^{4a}$ is independently H, $C(O)R^6$, or optionally substituted alkyl; $R^5$ is H, optionally substituted alkyl, or optionally substituted aryl; $R^6$ is optionally substituted alkyl or optionally substituted aryl; and each of x and y is independently 0, 1, 2, or 3; or Formula (II):

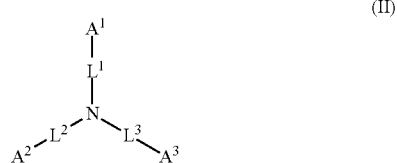

wherein each of $A^1$, $A^2$, and $A^3$ is independently selected from an acidic group (e.g., a carboxyl or phosphonyl); and each of $L^1$, $L^2$, and $L^3$ is independently bond, alkylene (e.g., $C_1$-$C_6$ alkylene), or heteroalkylene (e.g., $C_1$-$C_6$ heteroalkylene); or Formula (III):

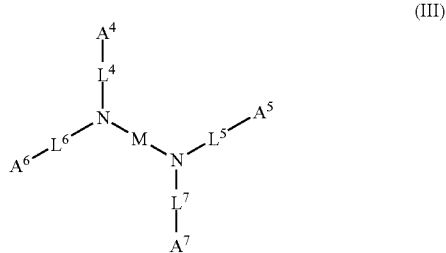

wherein each of $A^4$, $A^5$, $A^6$, and $A^7$ is independently an acidic group (e.g., a carboxyl or phosphonyl); each of $L^4$, $L^5$, $L^6$, and $L^7$ is independently bond, alkylene (e.g., $C_1$-$C_6$ alkylene), or heteroalkylene (e.g., $C_1$-$C_6$ heteroalkylene); and M is alkylene (e.g., $C_1$-$C_6$ alkylene) or heteroalkylene (e.g., $C_1$-$C_6$ heteroalkylene).

In another aspect, the present disclosure features a method for repairing a bone comprising placement of an implantable object, comprising: (a) stripping the periosteum off the external bone surface at a desired location; (b) applying an adhesive composition to the stripped bone; (c) placing the implantable object in contact with the adhesive composition and the bone in the desired orientation and location; (d) optionally inserting one or more retention bone screws; and (e) allowing the adhesive composition to cure. In some embodiments, the implantable object is an endosseous implant or an eposteal implant. In some embodiments, step (e) of the method occurs before or after step (c) or before or after step (d).

In some embodiments, the implantable object matches the size, shape, or other dimension of the implantation site and the implantable object comprises a smooth surface and a changing contour (e.g, to avoid a critical structure). In some embodiments, the implantable object is substantially free of a thread and comprises a bone-engaging element (e.g., a macro-rough surface, longitudinal groove, flute, fin, post, or stud). In some embodiments, the implantation site comprises a bone or bone socket (e.g., tooth socket).

In some embodiments, the implantable object is custom produced (e.g., based on CAT scan data), e.g., to match the shape of the implant bed. In some embodiments, the implantable object fits within the inner wall of the metaphysis or diaphysis cortex or is about the size and/or shape of a tooth root. In some embodiments, the implantable object is between about 0.1 mm and about 50 mm in diameter (e.g., about 0.5 mm to about 25 mm or about 1 mm to about 10 mm). In some embodiments, the implantable object comprises a port or opening.

In some embodiments, the method further comprises stripping soft issue, e.g., periodontal ligament, granulation tissue, or cyst lining, and/or shaping the bone with a recipient site preparation instrument. In some embodiments, the stripping and/or shaping occurs prior to or after application of the adhesive composition. In some embodiments, the recipient site preparation instrument acts subtractively or additively toward an implantation site to prepare said site for placement of an implantable object. In some embodiments, the implantation site comprises a bone or bone socket (e.g., tooth socket).

In some embodiments, a component of the RSP instrument (e.g., the RSP head) is custom produced (e.g., based on CAT scan data), e.g., to match the shape of the implantable object. In some embodiments, a component of the RSP instrument (e.g., the RSP head) fits within the inner wall of the metaphysis or diaphysis cortex or is about the size and/or shape of a tooth root. In some embodiments, a component of the RSP instrument (e.g., the RSP head) exhibits a displacement swing amplitude from about 2 μm to about 2 mm. In some embodiments, the direction of the displacement of a component of the RSP instrument (e.g., the RSP head) is aligned to be parallel with the path of insertion of the implantable object. In some embodiments, a component of the RSP instrument (e.g., the RSP head) exhibits a subsonic vibration (e.g., less than about 60 Hz), a sonic vibration (e.g., between about 60 Hz to about 25,000 Hz), or an ultrasonic vibration is between about 0.1 mm and about 50 mm in diameter (e.g., about 0.5 mm to about 25 mm or about 1 mm to about 10 mm).

In some embodiments, applying the adhesive composition is achieved by spreading or injecting. In some embodiments, the adhesive composition comprises a multivalent metal salt and an acidic compound. In some embodiments, the adhesive composition comprises an acidic compound of Formula (I):

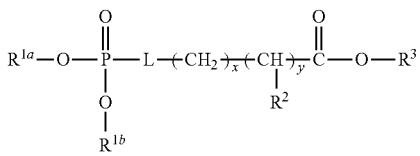

or a pharmaceutically acceptable salt thereof, wherein L is O, S, NH, or $CH_2$; each of $R^{1a}$ and $R^{1b}$ is independently H, optionally substituted alkyl, or optionally substituted aryl; $R^2$ is H, $NR^{4a}R^{4b}$, $C(O)R^5$, or $C(O)OR^5$; $R^3$ is H, optionally substituted alkyl, or optionally substituted aryl; each of $R^{4a}$ and $R^{4a}$ is independently H, $C(O)R^6$, or optionally substituted alkyl; $R^5$ is H, optionally substituted alkyl, or optionally substituted aryl; $R^6$ is optionally substituted alkyl or optionally substituted aryl; and each of x and y is independently 0, 1, 2, or 3; or Formula (II):

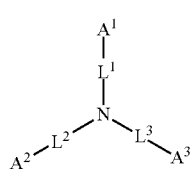

wherein each of $A^1$, $A^2$, and $A^3$ is independently selected from an acidic group (e.g., a carboxyl or phosphonyl); and each of $L^1$, $L^2$, and $L^3$ is independently bond, alkylene (e.g., $C_1$-$C_6$ alkylene), or heteroalkylene (e.g., $C_1$-$C_6$ heteroalkylene); or Formula (III):

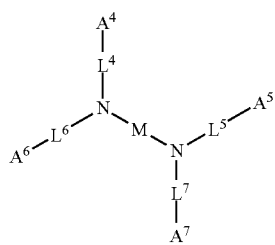

wherein each of $A^4$, $A^5$, $A^6$, and $A^7$ is independently an acidic group (e.g., a carboxyl or phosphonyl); each of $L^4$, $L^5$, $L^6$, and $L^7$ is independently bond, alkylene (e.g., $C_1$-$C_6$ alkylene), or heteroalkylene (e.g., $C_1$-$C_6$ heteroalkylene); and M is alkylene (e.g., $C_1$-$C_6$ alkylene) or heteroalkylene (e.g., $C_1$-$C_6$ heteroalkylene).

In another aspect, the present disclosure features an implantable object, wherein the shape of the implantable object matches the size, shape, or other dimension of the implantation site and the implantable object comprises a smooth surface and a changing contour (e.g, to avoid a critical structure).

In another aspect, the present disclosure features an implantable object, wherein the implantable object is substantially free of a thread and comprises a bone-engaging element (e.g., a macro-rough surface, longitudinal groove, flute, fin, post, or stud).

In another aspect, the present invention features an implantable object not requiring either an axis of rotational symmetry (i.e., a solid of rotation, e.g., a cylinder, bullet shape, etc.), an axis of translational and rotational symmetry (i.e., a screw shape) or a plane of bilateral symmetry (i.e., a plate) and featuring optimized efficiency of fit to the recipient site, In some embodiments, the implantable object matches the size, shape, or other dimension of the implantation site and the implantable object comprises a smooth surface and a changing contour (e.g, to avoid a critical structure). In some embodiments, the implantable object is substantially free of a thread and comprises a bone-engaging element (e.g., a macro-rough surface, longitudinal groove, flute, fin, post, or stud). In some embodiments, the implantation site comprises a bone or bone socket (e.g., tooth socket).

In some embodiments, the implantable object is custom produced (e.g., based on CAT scan data), e.g., to match the shape of the implant bed. In some embodiments, the implantable object fits within the inner wall of the metaphysis or diaphysis cortex or is about the size and/or shape of a tooth root. In some embodiments, the implantable object is between about 0.1 mm and about 50 mm in diameter (e.g., about 0.5 mm to about 25 mm or about 1 mm to about 10 mm). In some embodiments, the implantable object comprises a port or opening.

In some embodiments, the implantable object is rigidly held in place at least as long as the surgery or medical procedure in which it is being used. In some embodiments, the implantable object is rigidly held in place by bone. In some embodiments, the implantable object is rigid.

In some embodiments, the implantable object is adhered to bone surface. In some embodiments, the implantable object is adhered to the inner substance of a bone or the outer surface of a bone. In some embodiments, the implantable object is implanted fully in the bone. In some embodiments, the implantable object is implanted partially in the bone. In some embodiments, the implantable object is implanted partially in the bone and comprises an element remaining outside the bone. In some embodiments, the element remaining outside the bone is capable of physical contact with another device. In some embodiments, the element remaining outside the bone is capable of engaging another device (e.g., mechanically, magnetically, or otherwise physically). In some embodiments, the element remaining outside the bone comprises a substantially spherical surface. In some embodiments, the element remaining outside the bone comprises a cylindrical surface. In some embodiments, the element remaining outside the bone comprises a flat surface. In some embodiments, the element remaining outside the bone comprises a toroidal surface. In some embodiments, the element remaining outside the bone comprises a hard surface. In some embodiments, the element remaining outside the bone comprises a metallic element. In some embodiments, the element remaining outside the bone possesses radiopaque qualities. In some embodiments, the element remaining outside the bone emerges into the oral cavity. In some embodiments, the element remaining outside the bone emerges into the operative field during an orthopedic, oncological, neurological, ophthalmological, maxillofacial, etc. procedure. In some embodiments, the element remaining outside the bone emerges into the area of interest during oncological irradiation, resection, ablation, nerve stimulation, coagulation, repositioning, or other ablative or reconstructive procedure requiring a stable and consistent spatial reference over time.

In some embodiments, the implantable object is implanted into the jaw (e.g., the upper jaw or lower jaw). In some embodiments, the implantable object is a dental implant. In some embodiments, the implantable object is implanted into the middle ear. In some embodiments, the implantable object is implanted into the cranium or the facial skeleton. In some embodiments, the implantable object is implanted into one or more vertebrae. In some embodiments, the implantable object is implanted to make contact with one or more vertebrae. In some embodiments, the implantable object serves a function in spinal fusion. In some embodiments, the implantable object is implanted into the innominate bone or the pectoral girdle. In some embodiments, the implantable object is implanted into proximal or the distal regions of the long bones of the limbs. In some embodiments, the implantable object is an element of a prosthetic joint. In some embodiments, the implantable object is implanted into one or more of the carpal or the tarsal bones.

In some embodiments, the implantable object is used for the purpose of serving as a spatial reference. In some embodiments, the spatial reference is used in radiographic images or radiographic data. In some embodiments, the spatial reference is used in the construction of a model of tissues. In some embodiments, the model of tissues is a virtual model or a physical model. In some embodiments, the spatial reference is used in the construction of devices fitted to tissues.

In another aspect, the present disclosure features a guiding device, wherein the guiding device provides reference, position, orientation or retention of an implantable object in a geometrically defined position to a bone (e.g., a host bone) at an implantation site.

In another aspect, the present disclosure features a guiding device for providing shape to a bone-implantable material in contact with a bone for use in a dental, podiatric, orthopedic, veterinary, surgical, or other setting, wherein the guiding device comprises an opening for access to the space between the guiding device and the bone-implantable material.

In another aspect, the present disclosure features a guiding device for providing shape to a bone-implantable material in contact with a bone for use in bone grafting and bone implantation, wherein the guiding device comprises an opening for access to the space between the guiding device and the bone-implantable material.

In another aspect, the present disclosure features a guiding device for placement of an implantable object into a bone-implantable material at an implantation site related to bone, e.g., in the oral cavity, on the facial skeleton, on the cranium, on the spine, on the pectoral or pelvic girdles, or on the bones of the extremities, wherein the guiding device holds said implantable object in a geometrically defined position.

In some embodiments, the guiding device provides reference, position, orientation or retention of an implantable object in a geometrically defined position to a bone (e.g., a host bone) at an implantation site. In some embodiments, the guiding device comprises an opening for access to the space between the implantable object and an adhesive composition. In some embodiments, the guiding device is substantially rigid. In some embodiments, the guiding device is capable of release from the implantation site. In some embodiments, the guiding device comprises a naturally occurring polymer (e.g., collagen, a modified collagen, or gelatin) or a synthetic polymer (e.g., rubber, elastomer, PGA, or PLGA).

In some embodiments, the guiding device comprises at least 2, at least 3, at least 4, at least 5, or at least 6 components (e.g., implantable components). In some embodiments, the component (e.g., implantable component) is implanted fully in the bone. In some embodiments, the component (e.g., implantable component) is implanted partially in the bone.

In some embodiments, the guiding device is substantially rigid. In some embodiments, the guiding device is substantially elastic. In some embodiments, the guiding device is capable of release from the bone-implantable material. In some embodiments, the guiding device is designed not to release from the bone-implantable material. In some embodiments, the guiding device is designed to osseointegrate with implantation site bone once the bone-implantable material is resorbed by the host tissues. In some embodiments, the guiding device is not designed to osseointegrate with implantation site bone once the bone-implantable material is resorbed by the host tissues. In some embodiments, the guiding device is resorbable. In some embodiments, the guiding device comprises a naturally occurring polymer (e.g., collagen, a modified collaged, or gelatin) or a synthetic polymer (e.g., rubber, elastomer, PGA, or PLGA). In some embodiments, the guiding device comprises a water-soluble component.

In some embodiments, the guiding device comprises one or more openings. In some embodiments, the opening is a window or flap. In some embodiments, the guiding device may further engage an instrument for delivery of the bone-implantable material. In some embodiments, the instrument for delivery of the bone-implantable material comprises a carrier, cannula, syringe, tube, forceps, catheter, or needle. In some embodiments, the guiding device further comprises a means for placement of the instrument for delivery.

In some embodiments, the guiding device further comprises a mechanism for removing heat from the bone-implantable material. In some embodiments, the mechanism for removing heat comprises a thermal mass heat sink.

In some embodiments, the guiding device is supported by adjacent host tissue.

In some embodiments, the guiding device is constructed to fit the specific site of application.

In some embodiments, the guiding device is constructed to fit the specific site of application through the use of site morphology records (e.g., based on radiographic data, magnetic resonance data, ultrasound data, or optical scan data).

In some embodiments, the guiding device comprises a means of venting the space between the guiding device and the bone-implantable material.

In some embodiments, the guiding device is held in a geometrically defined manner.

In some embodiments, the guiding device is held in a geometrically defined manner in reference to rotational axes (e.g., all three rotational axes) and translational axes (e.g., all three translational axes).

In some embodiments, the guiding device is capable of holding a bone-shaping instrument, e.g., in relation to a bone.

In some embodiments, the bone-shaping instrument acts subtractively or additively toward the bone. In some embodiments, the bone-shaping instrument acts subtractively and the subtractive interaction comprises abrasion, attrition, chipping, drilling, shaving, or other means of modification. In some embodiments, the bone-shaping instrument acts additively and the additive interaction comprises augmentation.

In some embodiments, the bone-shaping instrument acts subtractively and the subtractive interaction comprises abrasion, attrition, chipping, drilling, shaving, or other means of modification.

In some embodiments, the guiding device is capable of holding a soft tissue cutting instrument, i.e., in relation to a tissues (e.g., orbital rim, cranium, vertebra, etc.)

In some embodiments, the soft tissue cutting instrument acts through the use of a sharp edge or through application of concentrated energy (e.g., laser beam, electrosurgical tip, Bovie, etc.).

In some embodiments, the guiding device is capable of holding an electrode, e.g., an ablation instrument, a nerve tissue stimulating instrument, e.g., brain stimulating electrode in relation to the cranium.

In some embodiments, the guiding device is capable of holding or placement of an implantable object, e.g., directly or indirectly. In some embodiments, the guiding device is capable of attachment to an implantable object, e.g., directly or indirectly. In some embodiments, the guiding device is capable of attachment to an implantable object directly through application of a compression force (e.g., friction).

In some embodiments, the guiding device is capable attachment to an implantable object indirectly through an intermediary element. In some embodiments, the intermediary element comprises a carrier, a retention aid, a screw, a keeper or a clip. In some embodiments, the intermediary element is capable of mechanical fixation to the implantable object. In some embodiments, the intermediary element is capable of mechanical fixation to the guiding device. In some embodiments, the fixation is capable of being released through a rotation, compression, or translation of the intermediary element. In some embodiments, the fixation is capable of being released by the application of heat (e.g., thermal expansion or phase change, etc.). In some embodiments, the fixation is capable of being released through deformation of the intermediary element. In some embodiments, the fixation is capable of being release by application of a compression force.

In some embodiments, the guiding device holds one or more implantable objects in a geometrically defined manner, e.g., in relation to a rotational axis or a translational axis. In some embodiments, the one or more implantable objects comprises at least 2, at least 3, at least 4, at least 5, or at least 6 implantable objects. In some embodiments, the one or more implantable objects comprises at least 6, at least 7, at least 8, at least 9, or at least 10 implantable objects. In some embodiments, the one or more implantable objects comprises at least 11, at least 12, at least 13, at least 14, or at least 15 implantable objects. In some embodiments, the guiding device is capable of holding an implantable object in a geometrically defined manner in relation to the bone. In some embodiments, the guiding device is capable of holding an implantable object in a geometrically defined manner in relation to another device. In some embodiments, the guiding device is capable of holding an implantable object in a geometrically defined manner in relation to a bone-implantable material. In some embodiments, the guiding device is capable of holding an implantable object in a geometrically defined manner in relation to a bone-implantable material during the application of said bone-implantable material. In some embodiments, the guiding device is capable of holding an implantable object in a geometrically defined manner in relation to a bone-implantable material during the setting of said bone-implantable material. In some embodiments, the guiding device is capable of holding an implantable object in a geometrically defined manner in relation to a bone-implantable material while the bone-implantable material is curing, i.e., becoming substantially solid. In some embodiments, the guiding device is capable of holding an implantable object in a geometrically defined manner in relation to a bone-implantable material while the bone-implantable material is forming an adhesive bond to a bone. In some embodiments, the guiding device is capable of holding an implantable object in a geometrically defined manner in relation to a bone-implantable material while the bone-implantable material is forming an adhesive bond to the implantable object. In some embodiments, the guiding device is capable of holding an implantable object in a geometrically defined manner in relation to a bone-implantable material while the bone-implantable material is becoming substantially load-bearing.

In another aspect, the present disclosure features a recipient site preparation (RSP) instrument. In some embodiments, the RSP instrument acts subtractively or additively toward an implantation site to prepare said site for placement of an implantable object. In some embodiments, the implantation site comprises a bone or bone socket (e.g., tooth socket).

In another aspect, the present invention features a RSP instrument comprising both the form of the implantable device and lack of radial asymmetry along the axis of insertion of the implantable.

In some embodiments, a component of the RSP instrument (e.g., the RSP head) is custom produced (e.g., based on CAT scan data), e.g., to match the shape of the implantable object. In some embodiments, a component of the RSP instrument (e.g., the RSP head) fits within the inner wall of the metaphysis or diaphysis cortex or is about the size and/or shape of a tooth root. In some embodiments, a component of the RSP instrument (e.g., the RSP head) exhibits a displacement swing amplitude from about 2 μm to about 2 mm. In some embodiments, the direction of the displacement of a component of the RSP instrument (e.g., the RSP head) is aligned to be parallel with the path of insertion of the implantable object. In some embodiments, a component of the RSP instrument (e.g., the RSP head) exhibits a subsonic vibration (e.g., less than about 60 Hz), a sonic vibration (e.g., between about 60 Hz to about 25,000 Hz), or an ultrasonic vibration is between about 0.1 mm and about 50 mm in diameter (e.g., about 0.5 mm to about 25 mm or about 1 mm to about 10 mm).

DETAILED DESCRIPTION

Implantable or Transplantable Objects

Figure 1:
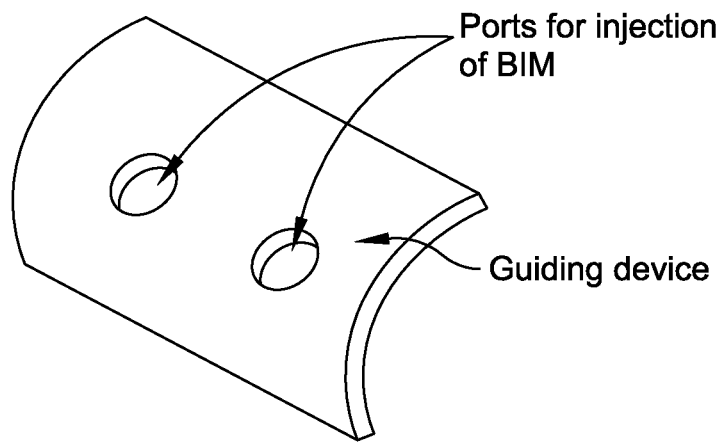
FIG. 1 is an illustration of an opening in an exemplary guiding device (e.g., form or guide).

In another aspect, the present disclosure features an implantable object or a transplantable object. In some embodiments, the implantable object comprises an implant (e.g., a dental implant, a mini-implant, an orthopedic implant, a suture anchor, a cochlear implant). In some embodiments, the transplantable object comprises tissue from another patient (e.g., allograft, xenograft) or tissue from another anatomic site of the patient (e.g., autograft). In some embodiments, the transplantable object comprises coral. In some embodiments, the implantable or transplantable object comprises various shapes and forms (e.g., a cage, a rod, a patch, a plug, a beam, a plate, a screw, a rod, a spacer, a disc, or other shape determined by the geometry or anatomy of the implantation or transplantation site). In some embodiments, a guiding device directly or indirectly holds an implantable or transplantable object. In some embodiments, the implantable or transplantable object is placed at the implantation site (e.g., into bone, or onto or in between bone surfaces) or the transplantation site (e.g., ocean floor). In some embodiments, the implantable or transplantable object is implanted into a certain site in the patient's body (e.g., mandible or maxilla, the skull, a vertebra, the innominate bone, the pectoral girdle, or other bones). In some embodiments, the implantable or transplantable object is embedded into the bone-implantable material (e.g., adhesive composition).

Exemplary implantable objects of the present disclosure may comprise metals, metallic alloys, polymers, minerals, ceramics, inorganics, organics, bone-implantable materials (e.g., adhesive compositions) or a combination thereof. In some embodiments, the implant comprises a metal, e.g., calcium, silicon, copper, silver, gold, zinc, iron, titanium, aluminum, cobalt, chromium, tantalum, molybdenum. In some embodiments, the implantable object comprises a metallic alloy, e.g., Titanium-4V-4Al, steel (e.g., stainless steel), bronze, brass, cobalt-chromium. In some embodiments, the implantable object comprises a polymer, e.g., a polyamide, glass, carbon, aromatic (e.g., polyphenylene vinylene) and conjugated (e.g., polyacetylene) polymers, intrinsically conductive polymers (e.g., polyaniline, polypyrrole, polythiophene), poly(ether ketone), poly(ethylene), poly(urethane), poly(methyl methacrylate), poly(carbonate), or poly(acrylic acid) polymers or a copolymer.

The implantable object may comprise resorbable and/or non-resorbable materials. In some embodiments, the implantable object comprises non-resorbable materials. In some embodiments, the implantable object comprises resorbable materials. In some embodiments, the implantable object comprises a combination of non-resorbable and resorbable materials.

The implantable object may comprise components that resorb at different rates. For example, the rate of resorption may vary due to intrinsic differences (e.g., composition, density, porosity) or extrinsic differences (e.g., shape, surface to volume ratio, thickness). In some embodiments, the implantable object (or certain components thereof) may resorb over a period of time of about 1 day, about 1 week, about 2 weeks, about 4 weeks, about 2 months, about 3 months, about 4 months, about 5 months, about 6 months, about 8 months, about 10 months, about 1 year, about 2 years, about 5 years, about 10 years, or longer.

Figure 12:
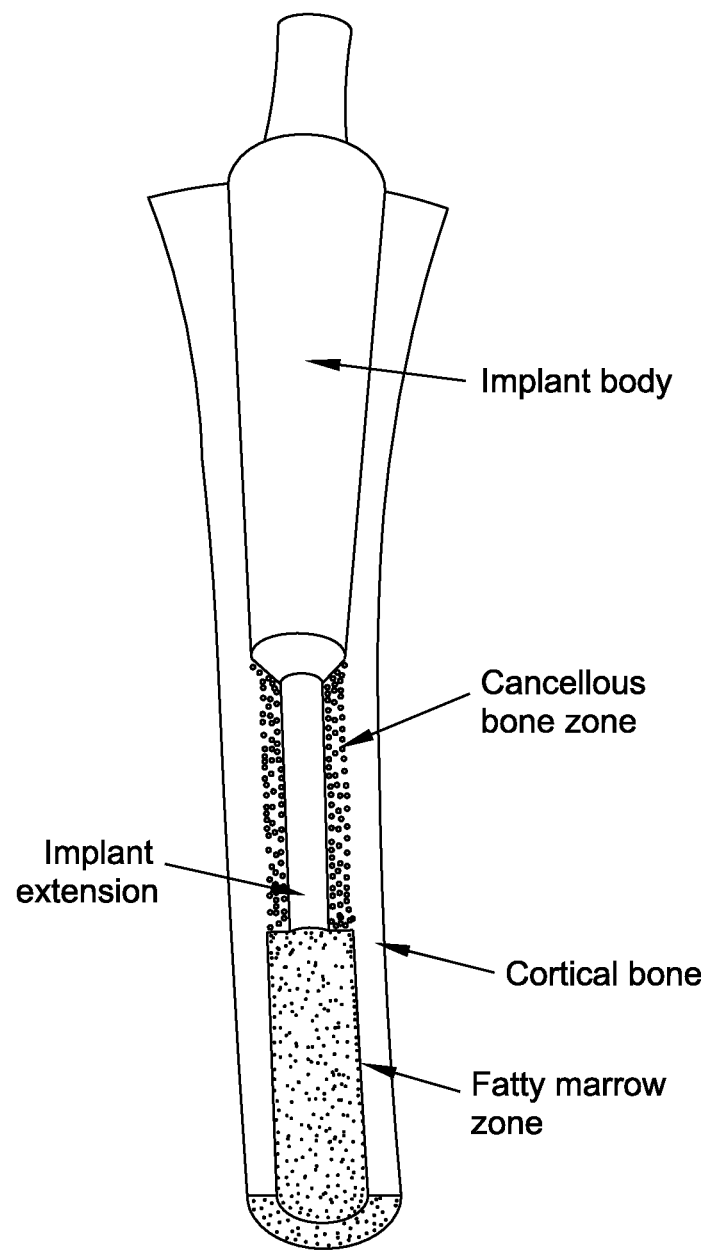
FIG. 12 illustrates an endosseous implantable object fitted to the endosteal surface of the diaphysis-metaphysis segment of a long bone, which demonstrates the implant extension feature engaging medullary cancellous bone beyond the zone of the low-tolerance fit of the implant body to the cortex.
Figure 13A:
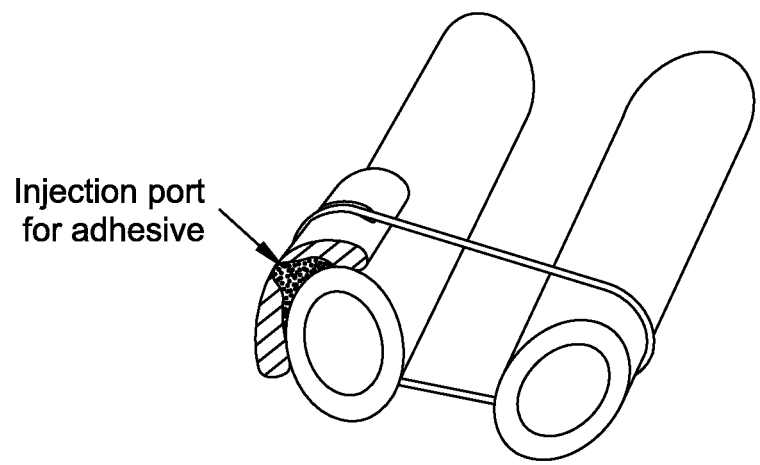
FIG. 13A illustrates an eposteal implantable object perforated to provide an injection port for the application and distribution of the bone-implantable material (e.g., adhesive composition) into the bone-implantable object gap space. Exemplified is an application in the orthopedic space with treatment for bunions. A metal suture maintains a corrected and better aligned position of the bones in the foot. The implantable object is applied to and adhered to the second metatarsal fibular aspect to serve as a base and retain an indwelling metal suture looping around the first metatarsal. Its use prevents the fracture of the second metatarsal
Figure 13B:
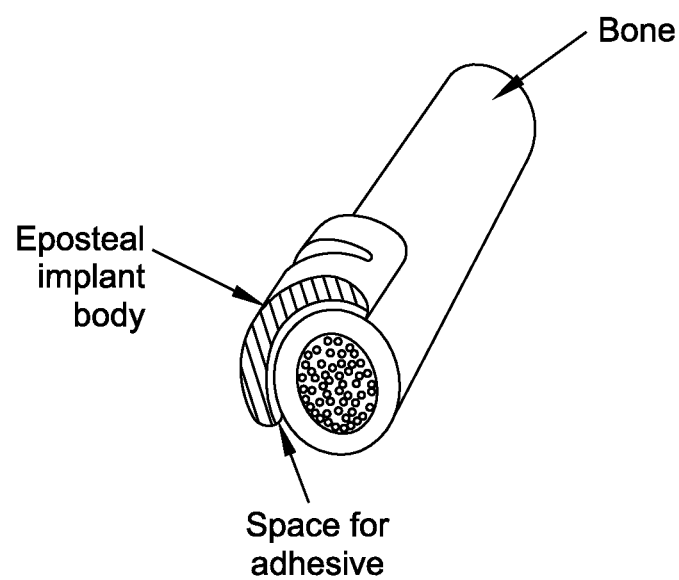
FIG. 13B illustrates an eposteal implantable object applied to the external surface of a long bone.

The implantable object may be endosseous, eposteal, or transosteal. The implantable object may be trans-mucosal or transdermal. In some embodiments, the implantable object is endosseous e.g., and engages the interior of the bone, e.g., as shown in FIG. 12. In other embodiments, the implantable object is eposteal (e.g., sub-periosteal), e.g., and engages the external surface of the bone, e.g., as shown in FIGS. 13A-B.

The shape of the implantable object may vary depending on the recipient site. In some embodiments, the implantable object is custom produced to match the shape or size of the recipient site (i.e., implant bed). In these cases, the production method may be informed by patient data, such as CAT scan, optical scan, or X-ray images. In some embodiments, the implantable object is pre-made in one or a variety of standard shapes suitable for particular applications (e.g., spinal fusion cages). For example, in the femoral stem or another long bone context, the implantable object may have a cross-sectional shape that approximates the usual shapes of the inner wall of the metaphysis or diaphysis cortex, depending on the application. In the dental context, the implantable object may reflect the size and shape of a specific tooth root to be extracted, already extracted or absent. The implantable object may also represent a category of tooth, e.g., mandibular incisor, maxillary cuspid, or may represent a series of ellipsoids or paraboloids of given certain idealized proportions.

The implantable object shape may also vary depending on the context of the potential implantation site and its use. In some embodiments, the implantable object may mimic or approximate all or part of the shape of a bone or a tooth (e.g., a tooth, such as the root or tooth shaft, a fragment of the calvarium, a nasal bone, etc.). In some embodiments, the implantable object is symmetrical in shape (e.g., rotationally symmetric). In some embodiments, the implantable object is not symmetrical in shape (e.g., not rotationally symmetric). In some embodiments, the implantable object has a cross sectional shape that is roughly oval, roughly triangular, or roughly figure eight-shaped. In some embodiments, the implantable object is not an object of rotation or a flat plate.

In the dental implant context, the implantable object shape may approximate the tooth root. In some embodiments, the implantable object comprises the shape of the entire tooth bone void, the root or a part of the tooth root, e.g., the cortex, medullary space, or a void present due to a pathological process. For example, the roughly oval or roughly triangular cross section of many tooth roots might provide a better fit to the available spaces in the jaws, thus maximizing stabilization, retention and providing optimal stress distribution. A range of shapes and sizes for the implantable object may accommodate the range of anatomical conditions presented by the patient. The method of preparation of the implant bed disclosed herein may allow for the implantable object shape to extend beyond the approximate solid of rotation form (e.g., a cylinder, a bullet shape, or a screw) accommodated within drill hole formed by a spun bone drill or a flat plate, perforated of not, inserted into a slot cut into the bone.

In orthopedic implant context, the implantable object may approximate the shape of a particular bone or part of a bone (e.g., the femoral stem, cranial flap, an aspect of the vertebra, or metatarsal sling) or space between bones including margins of the adjacent bones (e.g., facet joint). In these cases, the implantable object may be shaped to be close-fitting to the specific implantation site rather than constrained to solids of rotation, such as drill bits, flat plates or other arbitrary shapes.

Figure 7A:
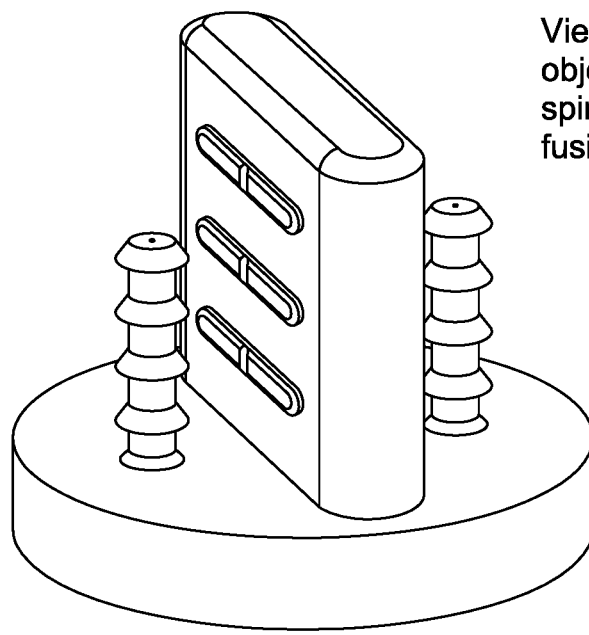
FIG. 7A illustrates an exemplary implantable object designed for spine fusion between the articular processes at the site of the facet joint.
Figure 7B:
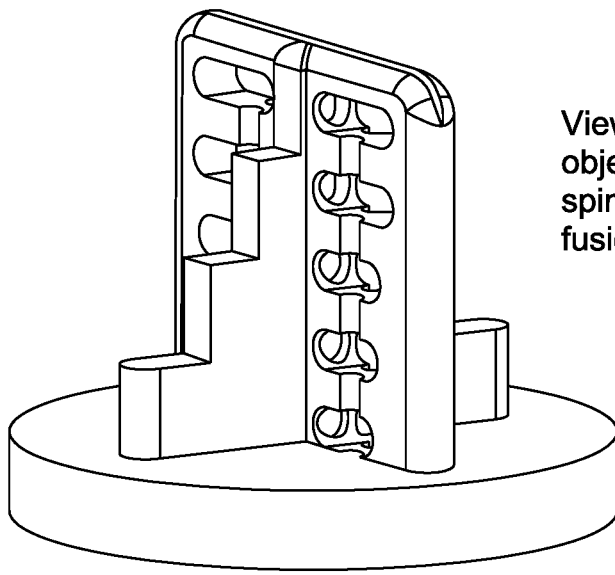
FIG. 7B illustrates an exemplary implantable object designed for spine fusion between the articular processes at the site of the facet joint.
Figure 7C:
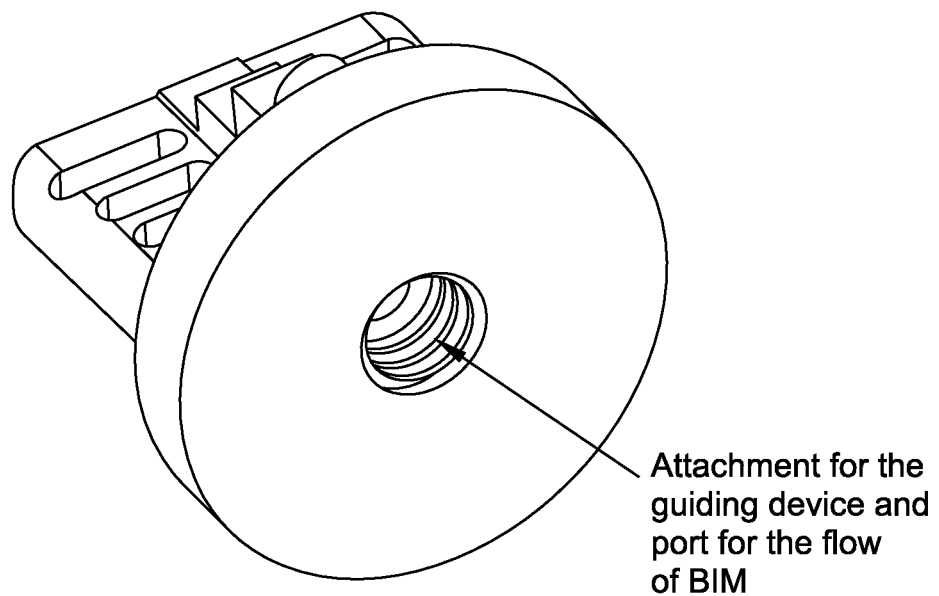
FIG. 7C illustrates an exemplary implantable object designed for spine fusion between the articular processes at the site of the facet joint demonstrating the site of attachment of the guiding device which also can conduct flow of a bone-implantable material (e.g., adhesive composition).

In some embodiments, the shape of the implantable object comprises design elements as a means of introducing a bone-implantable material (e.g., adhesive composition) once the implantable object is seated in the recipient site, e.g., through injection or cannula, as shown in FIG. 13A and FIG. 7C. These design elements also provide a space relief for venting of a bone-implantable material (e.g., adhesive composition). Exemplary design elements to provide said introduction or relief of a bone-implantable material include a port, channel, groove, slot, window, flap, hole, or other access mechanism.

The implantable object may also be shaped to provide resistance to rotation. In this case, the implantable object may not have an axis of rotation, an axis of shear translation (e.g., a solid of rotation or a plate shape), or an axis which combines rotation with translation (e.g., a screw). To enhance resistance to rotational moments about the long axis of the bone the eccentricity of the recipient site might be emphasized. Furthermore, the bone-engaging surface might comprise a macro-rough surface, longitudinal groove, flutes, fin, studs, posts, studs, or other feature which is capable of resisting rotation, e.g., either during healing or in the long term following bone ingrowth, as shown in FIGS. 7A-7B.

In some embodiments, the implantable object comprises an extension beyond the tip of the part of the implantable object retained by the adhesive or specifically prepared to engage the bone surface, e.g., an extension of smaller diameter or with higher fit tolerance. Said extension may increase the stability of the implant or enhance the resistance of a stump prosthesis implant to angular moments (stresses at an angle to the long axis of the bone and the implant) particularly if it engages mechanically stable tissues which might include calcified tissues such as medullary bone or distant cortical bone. An example of such an extension is shown in FIG. 12. In some embodiments, the implantable object may comprise an extension that is between about 0.1 cm and 1.0 cm, between about 1.0 cm 3.0 cm, between about 3.0 cm and 6.0 cm, between about 6.0 cm and 12.0 cm, between about 12.0 cm and 18.0 cm, and longer in length than about 18.0 cm or longer in length, i.e., beyond the edge of the part of the implant which is closely fitted to the bone surface. An implantable object featuring such an extension might require site preparation by conventional means, e.g., by a rotary instrument or impact, to allow desired seating.

Recipient Site Preparation Instruments

In some embodiments, the recipient site preparation (RSP) instrument acts subtractively or additively toward the bone. In some embodiments, the RSP instrument acts subtractively toward the bone, and the subtractive interaction comprises abrasion, attrition, chipping, or other means of modification of the bone through removal of substance. In some embodiments, the RSP instrument acts additively toward the bone, and the additive interaction comprises augmentation. In some embodiments, the RSP instrument acts to compact the bone by reducing the volume but not substantially reducing the mass of the calcified tissue.

The RSP instrument may be used to prepare the recipient site for placement of an implantable object into or onto a bony tissue, such as a prosthetic limb attachment, prosthetic joint attachment, maxillofacial prosthesis, dental implant with a crown or denture restoration, or any other prosthetic device benefitting from firm and defined direct, or indirect, contact with the skeleton. In some embodiments, an RSP instrument for this implantable object shape may be matched in its three-dimensional shape and size to the implantable object and need not be intended to be rotated.

The RSP instrument may comprise features designed to improve its performance, such as design features to improve cutting efficiency or to limit heat generation. Exemplary features to improve performance may include choice of the particle size and distribution (e.g., abrasive particle size and distribution) and the presence of cutting edges or points, as well as the separation distance between these features. The RSP instrument may also include design elements for easier removal of the spoils (e.g., bone slurry or bone chips) of the RSP process, such as a conduit for flow of a liquid (e.g., saline, water), grooves, perforations, internal irrigation, or a hollow basket design. The RSP instrument may also include design elements for removal of heat generated during the RSP process, such as a conduit for flow of a liquid (e.g., saline, water), grooves, perforations, internal irrigation, or a hollow basket design.

In some embodiments, the RSP instrument has a displacement swing amplitude from about 2 µm to about 2 mm, e.g., about 5 µm, about 10 µm, about 25 µm, about 50 µm, about 100 µm, about 250 µm, about 500 µm, about 750 µm, about 1 mm, about 1.25 mm, about 1.5 mm, about 1.75 mm, or about 2 mm. In some embodiments, the RSP instrument exhibits a subsonic vibration (e.g., less than about 60 Hz), a sonic vibration (e.g., between about 60 Hz to about 25,000 Hz), or an ultrasonic vibration (e.g., greater than about 25,000 Hz). The vibration, or the reciprocal motion of the RSP instrument may be generated through magnetostrictive, piezoelectric, electromechanical, magnetic, hydraulic means, or other. In some embodiments, the RSP instrument has a small swing displacement. One of the advantages of a small swing displacement is the improved selectivity of cutting of the relatively brittle bone and cartilage and sparing of the relatively elastic soft tissues, e.g., nerves, blood vessels, muscle, enveloping membranes, etc., thus providing a method with minimal collateral damage at the surgical site. In addition, the small swing vibration has a relatively compact configuration compared to that of many electrically powered saws and drills that use circular motion rather than vibrational motion. In some embodiments, the motion of the RSP instrument might coincide with the natural resonant frequency of the vibrating element.

In some embodiments, the direction of the displacement of the RSP head is aligned to be parallel with the path of insertion of the implantable object. In some embodiments, the direction of the displacement of the RSP head is aligned to be at a small angle, e.g., about 0.1 degree to about 1.0 degrees, about 1.0 degrees to about 2.0 degrees, about 2.0 degrees to about 5.0 degrees, about 5.0 degree to about 10.0 degrees, or about 10.0 degree to about 15.0 degrees to path of insertion of the implantable object. In some embodiments, the direction of the displacement of the RSP head is aligned to be at a larger angle, e.g., about 15 degrees to about 25 degrees, about 25 degrees to about 45 degrees, about 45 degrees to about 60 degrees, about 60 degrees to about 75 degrees, or about 75 degrees to about 90 degrees to path of insertion of the implantable object.

The RSP instrument may comprise a combination of modes to power its motion. In addition, the motion may be used on a single RSP instrument, with the orientation of the direction of the impulse, the relative phase of the vibrations, its intensity, and the timing and duration of application of the vibration might depend on variety of factors. These factors may include the scale of the cutting or compaction task (e.g., hip bone vs metatarsal bone), the density of the bone substrate (e.g., compact cortical vs cancellous, or healthy vs osteoporotic), the desired rate of removal of the bone substrate, the rate of production of bone chips/slurry to be removed, heat generation control, or another factor. The direction, frequency, amplitude and phase of vibration might be the same or different for the multiple motive devices or means whether they act simultaneously, sequentially or singly.

The RSP instrument may comprise a number of distinct components, including a bone-contacting element, a head, and a motive element. In some embodiments, the design of the connection between the bone-contacting element, head, and the motive element(s) allows for appropriate displacement path and amplitude without undue fatigue of the material through proper choice of materials and structural shapes. This in combination with abrasive, cutting, or smooth areas of the instrument results in the removal and/or compaction of the bone tissue may create the desired shape of the cavity for implant placement. In some embodiments, the RSP instrument or the implantable object may completely fill the initial bony void. In some embodiments, the RSP instrument or implantable object may not completely fill the initial bony void. Exemplary bony voids include a void in the alveolar ridge, e.g., left after the extraction of a tooth, or a void in the femoral medullary space devoid of trabecular bone. In some embodiments, the adhesive composition may fill the gap in the bony void not filled by the RSP instrument or the implantable object.

The design of the RSP instrument may include an abrasive or cutting aspect, which may, e.g., be in contact with some or all of the bone being prepared for implantable object placement. The distribution of the abrasive and the cutting elements may include variation in the roughness and size of the abrasive and cutting character. In some embodiments, the abrasive and cutting elements comprise grooves that may be uniform in size or may be of variable sizes, e.g., large or small. The abrasive and cutting elements may also comprise additional features, such as areas of relief or channels, to aid in clearing debris or cooling of the surface. The designs might also include specialized shapes to reflect certain anatomical situations, e.g., those involving the proximity of critical structures which must be avoided (e.g., nerves, blood vessels, tendons, etc.) as shown in FIGS. 15A-I. In the dental context, these structures might include the mental foramen, the incisive foramen, the inferior alveolar canal, the nasal floor, or the thin buccal plate of bone. In the spine fusion context, these structures might include the dorsal or ventral nerve roots. Shown are the lack of rotational symmetry of the instrument, the non-uniform distribution of the abrasive material on its surface, and the absence of the abrasive on selected areas of the surface preventing cutting of the bone by that sector of the head.

The RSP instrument might comprise an extension along its long axis in the direction away from the bone. The extension might be used for orientation and evaluation of angle of the osteotomy being prepared. The extension might also be of length equal to the substrate-contacting part of the head of the instrument to provide further orientation information to the operator.

The RSP instrument might comprise a mark, a groove, a collar, a notch, or another indicator of the depth of penetration of the instrument into the substance or the substance being worked to provide further orientation information to the operator.

The specific design of one or more of the RSP instrument elements may be made at any point in the implant procedure, e.g., during the planning phases (prior to implantation), or during the implantation process. In some embodiments, custom fabrication of the RSP instrument and the implantable object occurs concurrently with the design step. The selection of a specific implantable object shape, and instrument shape, may be made by considering one or more of the following factors: (1) measurement or scan of an extracted or evulsed tissue (e.g., freshly-extracted tooth root at the site of planned implantation) or the implantation site (e.g., tooth extraction socket, intervertebral disc space, inter-facet joint, amputation site); (2) clinical measurement of the planned implantation site; (3) measurement of flat radiographic image (e.g., periapical image); (4) measurement a tomographic image (e.g., a panoramic study); (5) measurement of 3-dimensional radiographic image (e.g., CAT or cone beam CT image), (6) optical scan of the planned implantation site or the extracted tooth root; and/or (7) the output of a software program using any of the foregoing sources of information. The choice of the form of the RSP instrument or implantable object may also depend on an aspect of the size and shape of the extracted of evulsed tissue (e.g., the neck of the tooth formerly occupying the planned implantation site). The method for use of the RSP instrument may be automatic, in that it forms the host site to receive a preformed implantable object in a desired orientation. The design and fabrication of the implantable object might involve the use of CAD/CAM software.

In some embodiments, the implantable object may be attached, directly or indirectly, to the motive element of the RSP instrument, and serve as a component of the RSP instrument in forming the recipient site for its implantation.

In some embodiments, the mass of the substrate-contacting element, e.g., bone contacting part, might constitute a small fraction of the entire RSP instrument. In some embodiments, the mass of the RSP instrument but not of the substrate-contacting element might be augmented to increase its inertial mass and thus increase precision and stability of the instrument. In some embodiments, the instrument is hand-held. In some embodiments, the instrument is attached to a supporting structure.

Guiding Devices

Figure 3A:
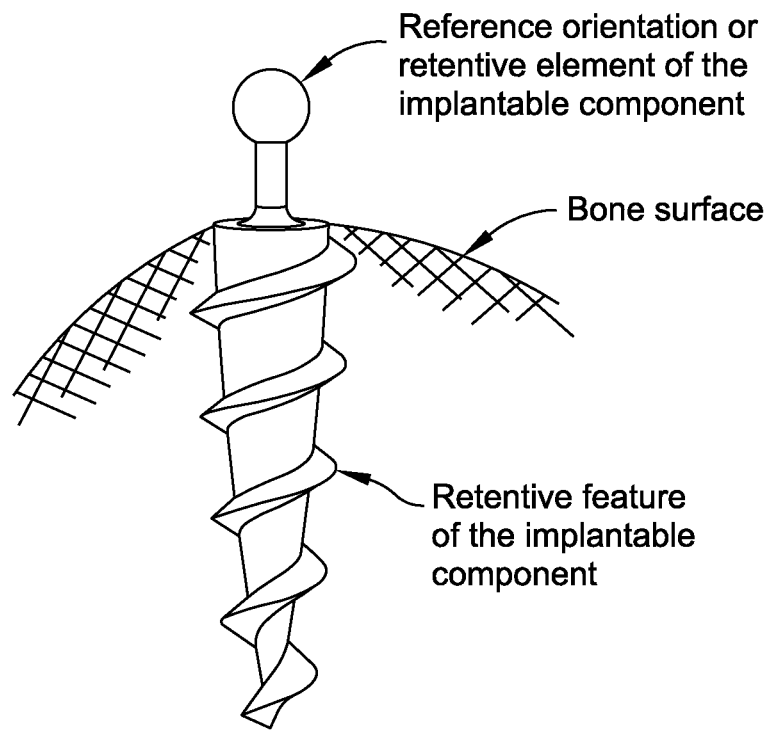
FIG. 3A illustrates an exemplary implantable component designed for screw retention to the bone demonstrating a transmucosal or transdermal reference element, that has penetrated the soft tissue, e.g., skin or gingiva.
Figure 3B:
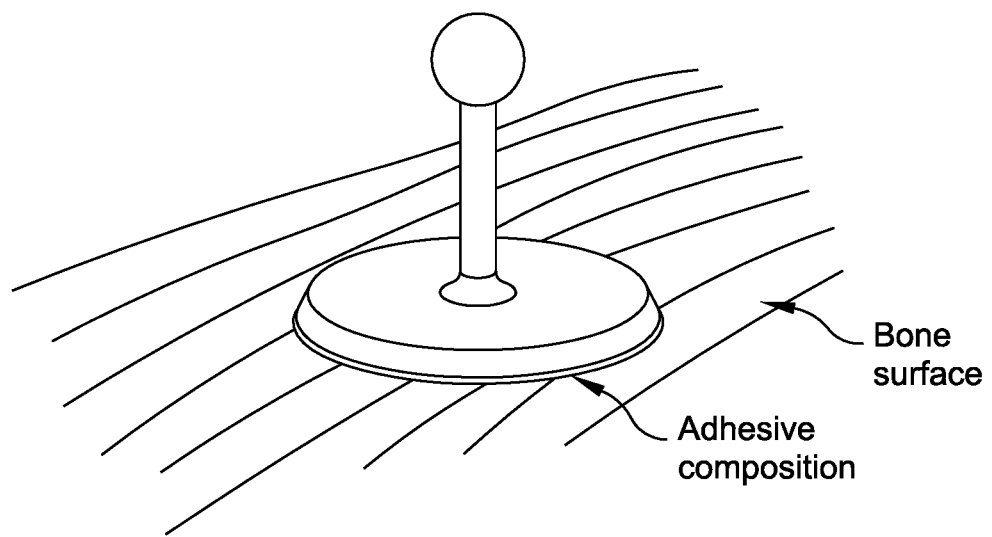
FIG. 3B illustrates an exemplary component of a guiding device designed for adhesive fixation to the bone demonstrating a layer of bone-implantable material (BIM, e.g., adhesive composition) retaining the base to bone.

Described herein are also guiding devices that may provide orientation and retention to a component. In some embodiments, the guiding device comprises a structure. In some embodiments, the structure comprises a plurality of components. In some embodiments, the guiding device comprises one or several components. In some embodiments, the guiding device is an assembly comprising components. In some embodiments, the guiding device comprises two or three components. In some embodiments, the guiding device comprises four, five, or six components. In some embodiments, the guiding device comprises 7, 8, 9, 10 or 11 components. In some embodiments, the guiding device comprises 12 or more components. In some embodiments, the component comprises a bridging component capable of attaching to other components. In some embodiments, the component comprises an implantable component inserted into a host site (e.g., bone) and retained by a screw feature as shown in FIG. 3A, by a bone implantable material (e.g., adhesive composition), or by any similar means. In some embodiments, the component comprises an implantable component inserted onto a host site (e.g., bone) and retained by a bone implantable material (e.g., adhesive composition) as shown in FIG. 3B. In some embodiments, the components are attached to one another by an element either directly or indirectly through intermediary components.

Figure 4:
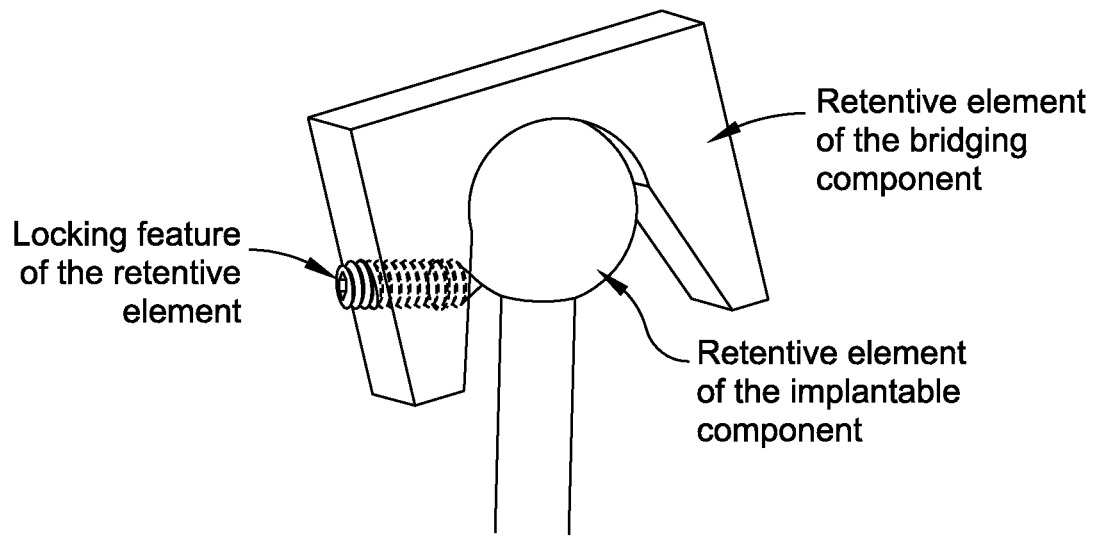
FIG. 4 illustrates an exemplary interaction of the retentive element of the bridging component of the guiding device and the retentive element of the implantable component of the guiding device, highlighting the elective locking feature.
Figure 6A:
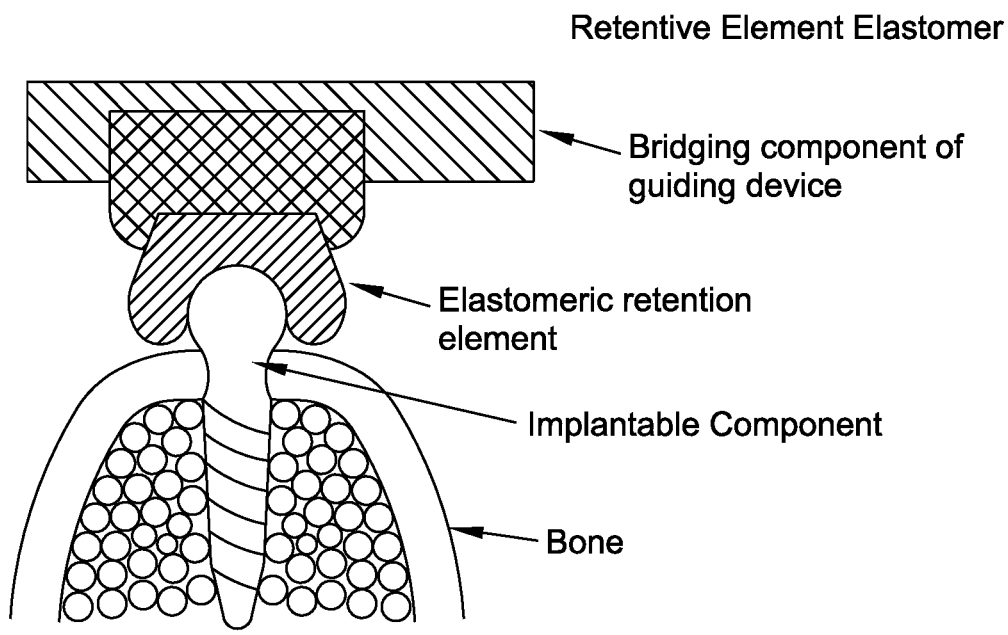
FIG. 6A is an illustration of a multi-component guiding device shown with a retention element (e.g., elastomer) serving as an intermediary component to attach from a retention element (e.g., the keeper) of the guiding device bridging component to the reference element of an implantable component (e.g., a mini-implant).
Figure 6B:
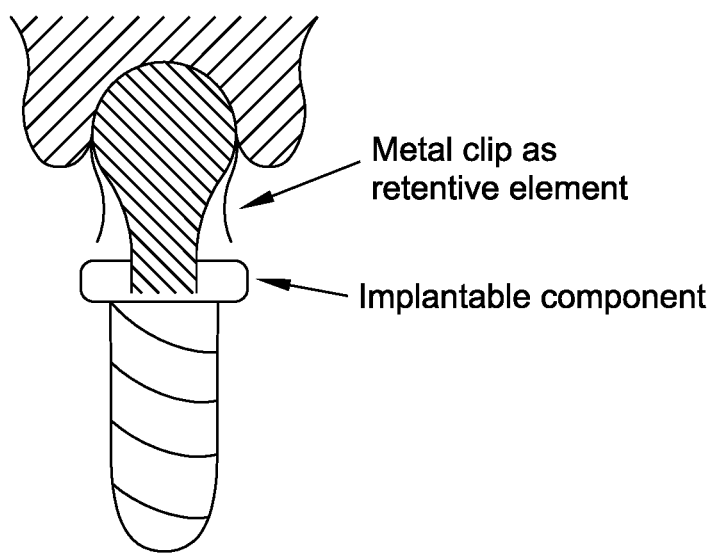
FIG. 6B is an illustration of a multi-component guiding device shown with a retention element (e.g., metal clip) serving as an intermediary component to attach from a retention element (e.g., the keeper) of the guiding device bridging component to the reference element of an implantable component (e.g., a mini-implant).

In some embodiments, the guiding device is comprised of rigid or elastic components. In some embodiments, the guiding device is substantially rigid. In some embodiments, the guiding device is substantially elastic. In some embodiments the components comprising the guiding device might be composed of different materials or materials possessing varied mechanical (e.g., stiffness, permeation, actuation), biophysical (e.g., solubility, speed of degradation, etc.), pharmaceutical (e.g., contain and diffuse drugs), or biochemical properties (e.g., contain and diffuse chemotactic agents, signaling compounds, sites for attachment of cells, etc.). In some embodiments, the components comprise various shapes (e.g., flat, cylindrical, spherical, ellipsoidal, toroidal, or a surface segment of any of these or their combinations) or features (e.g., a thread, a bit, a dovetail, a socket, a notch, a slot, a channel, a barrel, a piston) that alone or through assembly allow for the intended use or uses of the guiding device at various phases of use. In some embodiments, the shapes or features form elements to be used for reference, orientation, or retention functions of the components. In some embodiments the elements might be used alone or in any combination for the performance of reference, placement (e.g., an inserter, a driver, a syringe), orientation (e.g., a key, a notch, a slide, a knob), or retention (e.g., a screw, a keeper, a lock, a latch, a snap, a clip, a spring, an o-ring) functions. An exemplary guiding device with a screw retentive element used to attach the bridging component to the implantable component is shown in FIG. 4. In some embodiments, the elements may comprise metals, elastomers, rubber, or plastics. An exemplary guiding device with an elastomeric retentive element used to attach the bridging component to the implantable component is shown in FIG. 6A. An exemplary guiding device with metal clip retentive element used to attach the bridging component to the implantable component is shown in FIG. 6B.

In some embodiments, the element (e.g., reference element, retention element, orientation element) of the implantable component that extends outside the bone comprises a partial or full spherical surface as shown in FIG. 3A. In some embodiments, the element of the implantable component that extends outside the bone comprises a partial or full cylindrical surface. In some embodiments, the element of the implantable component that extends outside the bone comprises a partial or full toroidal surface. In some embodiments, the element of the implantable component that extends outside the bone comprises a flat surface. In some embodiments, the element of the implantable component that extends outside the bone comprises a hard surface.

In some embodiments, the element (e.g., reference element, orientation element) of the implantable component that extends outside the bone comprises radiopaque qualities. In some embodiments, the element of the implantable component that extends outside the bone comprises a metal (e.g., Ti, Cr, Ni, Fe, Au, Ag, Pt, Pd, Cu, etc). In some embodiments, there are multiple implantable components (e.g., about 2, about 3, about 4, about 5, about 6, about 7, about 8, about 9, about 10, or more) placed at the implantation site (e.g., into bone, or onto or in between bone surfaces) which comprises a system of radiopaque elements to define a frame of reference.

In some embodiments, the guiding device or components of the guiding device are indwelling, removable, biodegradable or resorbable. In some embodiments, the guiding device comprises a naturally occurring polymer or a synthetic polymer. In some embodiments, the guiding device comprises a naturally occurring polymer (e.g., collagen, modified collagen, or gelatin). In some embodiments, the guiding device comprises a synthetic polymer (e.g., rubber, elastomer, PGA, or PLGA). In some embodiments, the guiding device comprises water soluble components. In some embodiments, one component of the guided device is degraded or resorbed (e.g., selectively degraded or resorbed) before another component is degraded or resorbed.

In some embodiments, the shape of the guiding device is modifiable. In some embodiments, the guiding device retains the memory of a preferred shape for function. In some embodiments, the guiding device retains the memory of a preferred shape for function and is stored or applied in an altered shape. In some embodiments, the guiding device is applied rolled up, folded, or in an otherwise more convenient form for the mode of application (e.g., an injection). In some embodiments, the guiding device is applied rolled up, folded, or in an otherwise more convenient form for storage. In some embodiments, the guiding device is held in a desired shape for application by another guiding device. In some embodiments, said other guiding device is modified (e.g., loses its shape or strength) in the destination environment. In some embodiments, the guiding device is applied in its desired final form. In some embodiments, the guiding device is applied in a desired shape and then is modified (e.g., loses its shape or strength) in the destination environment. In some embodiments, the change in shape accompanies dissolution or hydration of component parts of the guiding device.

In some embodiments, the guiding device comprises an opening (e.g., a window, a flap, a vent, a port, a channel, or another orifice) to allow access to the interior of the guiding device. In some embodiments, the guiding device comprises an opening to constrain the path of an instrument, implantable object, or bone-implantable material through the guiding device. In some embodiments, the guiding device comprises an opening to allow access for the instrument, implantable object, or bone-implantable material to the interior of the guiding device. In some embodiments, the opening allows injection, venting, or inspection of the bone-implantable material. In some embodiments, the opening is useful during the application or setting of the bone-implantable material, or other phase of use thereof. In some embodiments, the opening allows for attachment of a carrier, cannula, syringe, tube, forceps, carrier, or needle) for application of the bone-implantable material.

Figure 2:
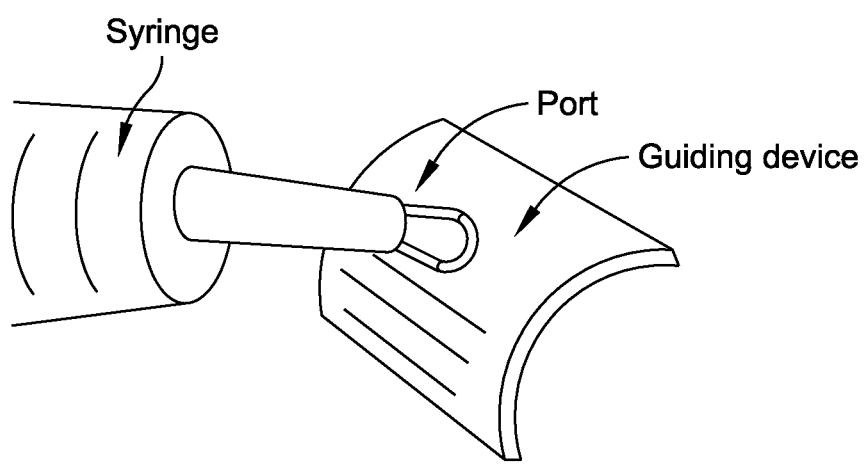
FIG. 2 is an illustration of the attachment of an exemplary instrument (e.g., a syringe) to an exemplary guiding device (e.g., form or guide) to inject bone-implantable material, BIM, (e.g., adhesive composition) through an opening in the device.

In some embodiments, the guiding device comprises an opening to allow inspection through the guiding device. In some embodiments, the guiding device comprises an inspection port or window. In some embodiments, the guiding device comprises a means of venting the space between the guiding device and the bone-implantable material. In some embodiments, the guiding device comprises an opening to allow for modification of the shape or size of the guiding device. In some embodiments, the guiding device comprises an opening to allow for modification of the bone-implantable material held in place by the guiding device. In some embodiments, the opening in the guiding device is exemplified in FIGS. 1-2.

In some embodiments, the guiding device does not comprise an opening (e.g., a window, flap, vent, or other orifice). In some embodiments, the guiding device does not comprise an opening (e.g., a window, flap, vent, or other orifice) that provides access to the interior of the guiding device. In some embodiments, the guiding device is capable of attachment to an instrument used for injection of a bone-implantable material. In some embodiments, the guiding device is supported by an instrument used for injection of a bone-implantable material. In some embodiments, the instrument comprises a carrier, cannula, syringe, tube, forceps, carrier, or needle.

In some embodiments, the guiding device further comprises a mechanism for removing heat from the bone-implantable material. In some embodiments, the mechanism comprises a thermal mass heat sink. In some embodiments, the mechanism comprises a fluidic means of removing heat from the composition. In some embodiments, the mechanism comprises a space for an endothermic reaction to consume heat generated from the bone-implantable material.

In some embodiments, the guiding device is custom made based on a specific need (e.g., based on the need of a specific patient). In some embodiments, the guiding device is constructed to individually fit the site of application. In some embodiments, the guiding device is constructed to individually fit the site of application through the use of morphology records. In some embodiments, the morphology records are based on data obtained from a patient. In some embodiments, the data obtained from a patient comprise radiographic data, magnetic resonance data, ultrasound data, or optical data, or a combination of several of the data types. In some embodiments, the guiding device is custom made to the match the anatomical details of a specific patient.

Figure 10:
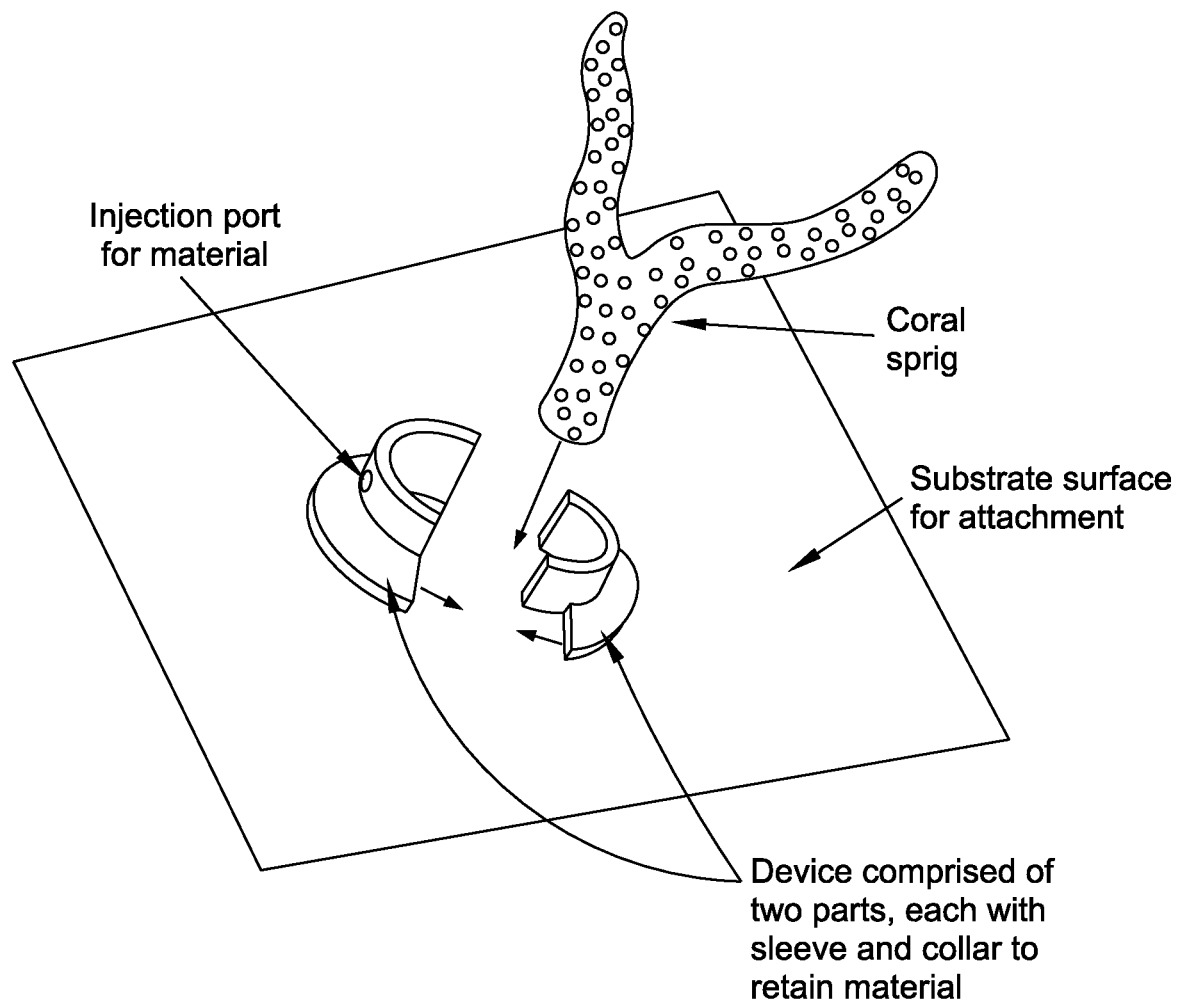
FIG. 10 is an illustration of an exemplary multi-component guiding device (e.g., form or guide) comprising two bridging components with sleeve and collar elements that interlock to each other in use to relate an exemplary transplantable object (e.g., coral) and attach the transplantable object to a substrate (e.g. ocean floor) with exemplary bone-implantable material (e.g., adhesive composition) applied through injection port of guiding device, as used in coral restoration.

In some embodiments, the patient is a human. In some embodiments, the patient is an adult or a child. In some embodiments, the patient is osteoporotic or osteopenic. In some embodiments, the patient is a non-human mammal, e.g., a primate, a dog, a horse, a cow, a pig, or other mammal. In some embodiments, the patient is an invertebrate, e.g., coral as shown in FIG. 10. In some embodiments, the patient is a non-animal substance (e.g., metal, rock, ceramic, concrete, polymer, glass or composites) or a structure comprising (e.g., metal, rock, ceramic, concrete, polymer, glass, or composites) or a substrate (e.g., ocean floor, river bed).

In some embodiments, the guiding device is applied to the site of use without direct visualization (e.g., blindly). In some embodiments, the guiding device is applied to the site of use without direct visualization (e.g., blindly) in a closed procedure through a minimal incision or injection.

In some embodiments, the guiding device, or a subassembly or component of the guiding device, is produced (e.g., produced in part or in full) through digitally controlled milling, grinding, cutting, drilling, or other subtractive method. In some embodiments, the guiding device, or a subassembly or component of the guiding device, is produced (e.g., produced in part or in full) through a digitally controlled three-dimensional printing process or other additive method. In some embodiments, the guiding device, or a subassembly or component of the guiding device, is produced (e.g., produced in part or in full) through a three-dimensional printing (e.g., binder jetting), three-dimensional photofixation lithography, stereolithography, or similar method of producing a solid form. In some embodiments, the guiding device, or subassemblies or components of the guiding device, is produced (e.g., produced in part or in full) through extrusion, molding, stamping, forging, die tapping, lathing, casting, electrospinning, spin lacing, or similar method of producing a solid form.

Bone-Implantable Materials

Described herein are bone implantable materials (BIM) that exhibit load-bearing or adhesive properties (e.g., to bone tissue, to titanium and its alloys, to stainless steels, etc.). In some embodiments, the BIM is biodegradable, resorbable, or osteoconductive. In some embodiments, the BIM is substantially stable (e.g., dimensionally, e.g., linearly or volumetrically) while undergoing a process, e.g., setting, curing, hardening, biodegradation, resorption and bone deposition. In some embodiments, the process (e.g., setting, curing, hardening, biodegradation, resorption, remodeling) substantially preserves the size and form of the BIM until such process reaches completion, yielding substantially unchanged size and form composed of substance resulting from the process (e.g., set, cured or hardened BIM; or new bone deposited as a result of turnover of BIM to bone). In some embodiments, the BIM might comprise adhesive compositions comprising a mixture of a multivalent metal salt, an acidic compound, and an aqueous medium.

Exemplary multivalent metal salts may be organic or inorganic in nature and include calcium phosphates (e.g., hydroxyapatite, octacalcium phosphate, tetracalcium phosphate, tricalcium phosphate), calcium nitrate, calcium citrate, calcium carbonate, magnesium phosphates, sodium silicates, lithium phosphates, titanium phosphates, strontium phosphates, barium phosphates, zinc phosphates, calcium oxide, magnesium oxide, and combinations thereof.

The amount of each multivalent metal salt (e.g., a calcium phosphate or calcium oxide or a combination thereof) may vary, e.g., between about 10% to about 90 weight by weight (w/w) of the combined mass of the multivalent metal salt and a compound. In some embodiments, the amount of the multivalent metal salt (e.g., a calcium phosphate or calcium oxide or a combination thereof) is in the range of about 10% to about 90%, about 15% to about 85%, about 20% to about 80%, about 30% to about 75%, about 40% to about 70%, or about 50% to about 65% w/w of the total composition. In other embodiments, the amount of the metal salt (e.g., a calcium phosphate or calcium oxide or a combination thereof) is in the range of about 5% to about 95%, about 10% to about 85%, about 15% to about 75%, about 20% to about 65%, about 25% to about 55%, or about 35% to about 50% w/w of the combined mass of the multivalent metal salt and a compound.

In some embodiments, the multivalent metal salt comprises calcium. In some embodiments, the multivalent metal salt comprises calcium and phosphate. In some embodiments, the multivalent metal salt comprises tetracalcium phosphate. In some embodiments, the composition comprises a plurality of multivalent metal salt compounds. In some embodiments, the plurality comprises tetracalcium phosphate and at least one other multivalent metal salt compound. In some embodiments, the multivalent metal salt comprises hydroxyapatite. In some embodiments, the multivalent metal salts comprise tricalcium phosphate. In some embodiments, the tricalcium phosphate comprises either alpha tricalcium phosphate or beta tricalcium phosphate. In some embodiments, the multivalent metal salts comprise an oxide. In some embodiments, the multivalent metal salt is calcium oxide. In some embodiments, the multivalent metal salt compound does not comprise tetracalcium phosphate. In some embodiments, the composition comprises tricalcium phosphate and calcium oxide.

In some embodiments, the multivalent metal salt is initially provided as a powder or as a granule. These powders may exhibit a mean particle size of about 0.001 to about 0.250 mm, about 0.005 to about 0.150 mm, about 0.25005 to about 0.75075 mm, 0.25 to about 0.5010 to about 0.050 mm, about 0.015 to about 0.025 mm, about 0.020 to about 0.060 mm, about 0.020 to about 0.040 mm, about 0.040 to about 0.100 mm, about 0.040 to about 0.060 mm, about 0.060 to about 0.150 mm, or about 0.060 to about 0.125 mm. The mean particle size may be bi-modal to include any combination of mean particle sizes as previously described. These granules may exhibit a mean granule size of about 0.050 mm to about 5 mm, about 0.100 to about 1.500 mm, about 0.125 to 1.000 mm, 0.125 to 0.500 mm, about 0.125 to 0.250 mm, about 0.250 to 0.750 mm, about 0.250 to 0.500 mm, about 0.500 to 1.00 mm, about 0.500 to 0.750 mm. The mean granule size may be multi-modal to include any combination of mean granule sizes as previously described. The granules may be supplied with a various proportion of porosity and a various size of internal pores. In some embodiments, varying sizes of said powders or granules may be used in the adhesive composition.

Exemplary acidic compounds may be of Formula (I):

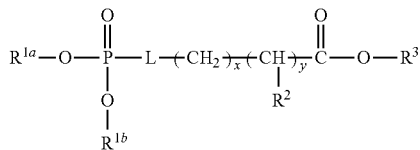

wherein L is O, S, NH, or $CH_2$; each of $R^{1a}$ and $R^{1b}$ is independently H, optionally substituted alkyl, or optionally substituted aryl; $R^2$ is H, $NR^{4a}R^{4b}$, $C(O)R^5$, or $C(O)OR^5$; $R^3$ is H, optionally substituted alkyl, or optionally substituted aryl; each of $R^{4a}$ and $R^{4b}$ is independently H, $C(O)R^6$, or optionally substituted alkyl; $R^5$ is H, optionally substituted alkyl, or optionally substituted aryl; $R^6$ is optionally substituted alkyl or optionally substituted aryl; and each of x and y is independently 0, 1, 2, or 3.

In some embodiments, L is O or S. In some embodiments, L is O. In some embodiments, each of $R^{1a}$ and $R^{1b}$ is independently H. In some embodiments, L is O, and each of $R^{1a}$ and $R^{1b}$ is H. In some embodiments, $R^2$ is H, $NR^{4a}R^{4b}$, or $C(O)R^5$. In some embodiments, $R^2$ is $NR^{4a}R^{4b}$. In some embodiments, $R^2$ is $NR^{4a}R^{4b}$ and each of $R^{4a}$ and $R^{4b}$ is independently H. In some embodiments, L is O, each of $R^{1a}$ and $R^{1b}$ is independently H, $R^2$ is $NR^{4a}R^{4b}$, and each of $R^{4a}$ and $R^{4b}$ is independently H. In some embodiments, $R^3$ is H. In some embodiments, L is O, each of $R^{1a}$ and $R^{1b}$ is independently H, $R^2$ is $NR^{4a}R^{4b}$, each of $R^{4a}$ and $R^{4b}$ is independently H, and $R^3$ is H. In some embodiments, each of x and y is independently 0 or 1. In some embodiments, each of x and y is independently 1. In some embodiments, L is O, each of $R^{1a}$ and $R^{1b}$ is independently H, $R^2$ is $NR^{4a}R^{4b}$, each of $R^{4a}$ and $R^{4b}$ is independently H, $R^3$ is H, and each of x and y is 1. In some embodiments, the acidic compound of Formula (I) is phosphoserine.

Exemplary acidic compounds may be of Formula (II):

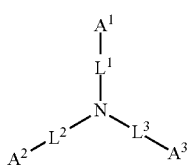

wherein: each of $A^1$, $A^2$, and $A^3$ is independently selected from an acidic group (e.g., a carboxyl or phosphonyl); and each of $L^1$, $L^2$, and $L^3$ is independently bond, alkylene (e.g., $C_1$-$C_6$ alkylene), or heteroalkylene (e.g., $C_1$-$C_6$ heteroalkylene).

In some embodiments, each of $A^1$, $A^2$, and $A^3$ is independently a carboxyl or phosphonyl. In some embodiments, $A^1$ is carboxyl, and $A^2$ and $A^3$ are phosphonyl. In some embodiments, $A^1$, $A^2$ and $A^3$ are phosphonyl.

In some embodiments, each of $L^1$, $L^2$, and $L^3$ is $C_1$-$C_3$ alkylene. In some embodiments, each of $L^1$, $L^2$, and $L^3$ is $C_1$ alkylene.

In some embodiments, the acidic compound of Formula (II) is a compound of Formula (II-a) or (II-b).

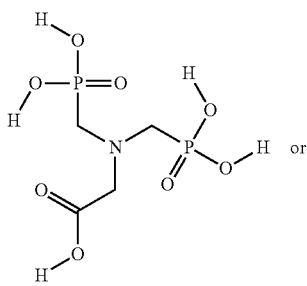

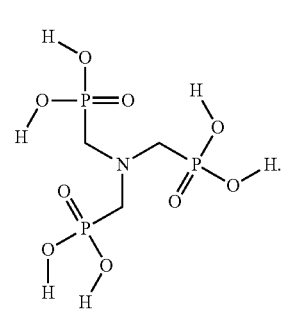

Exemplary acidic compounds may be of Formula (III):

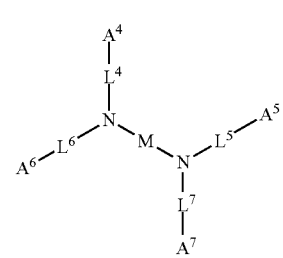

wherein: each of $A^4$, $A^5$, $A^6$, and $A^7$ is independently an acidic group (e.g., a carboxyl or phosphonyl); each of $L^4$, $L^5$, $L^6$, and $L^7$ is independently bond, alkylene (e.g., $C_1$-$C_6$ alkylene), or heteroalkylene (e.g., $C_1$-$C_6$ heteroalkylene); and M is alkylene (e.g., $C_1$-$C_6$ alkylene) or heteroalkylene (e.g., $C_1$-$C_6$ heteroalkylene).

In some embodiments, $A^4$, $A^5$, $A^6$ and $A^7$ are carboxyl.

In some embodiments, $L^4$, $L^5$, $L^6$, and $L^7$ are $C_1$-$C_3$ alkylene. In some embodiments, $L^4$, $L^5$, $L^6$, and $L^7$ are $C_1$ alkylene.

In some embodiments, M is $C_1$-$C_4$ alkylene. In some embodiments, M is $C_2$ alkylene. In some embodiments, M is $C_3$ alkylene. In some embodiments, M is $C_2$-$C_6$ heteroalkylene. In some embodiments, M is $C_6$ heteroalkylene.

In some embodiments, the acidic compound of Formula (III) is an acidic compound of Formula (III-a), (III-b), or (III-c).

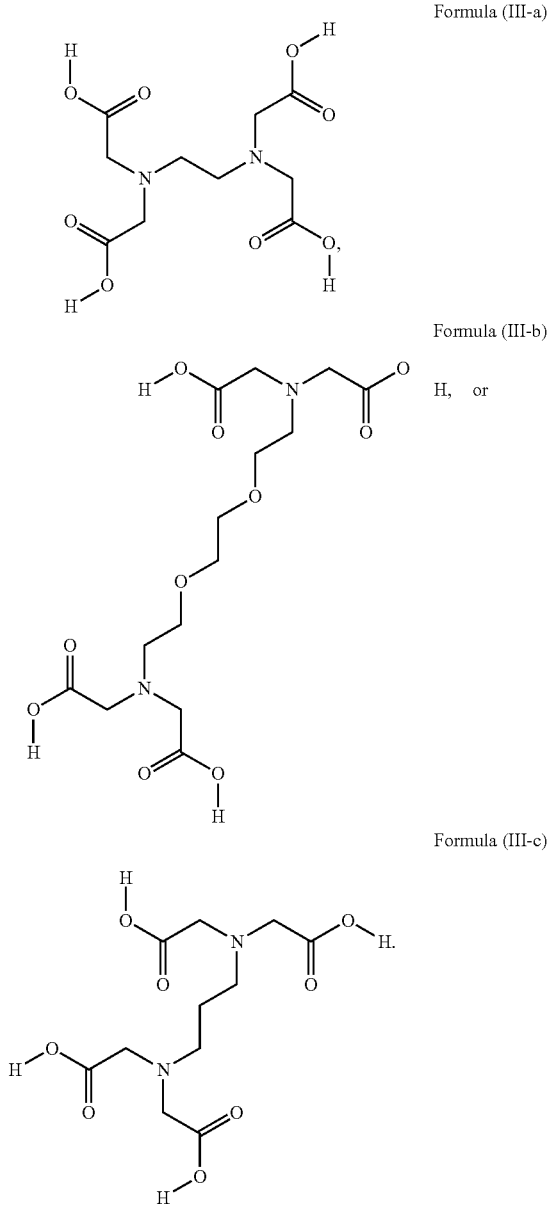

Formula (III-a)

Formula (III-b)

H, or

Formula (III-c)

As used herein, the term "optionally substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds (e.g., alkyl, alkenyl, alkynyl, cycloalkyl, heterocycloalkyl, aryl, or heteroaryl, any of which may itself be further substituted), as well as halogen, carbonyl (e.g., aldehyde, ketone, ester, carboxyl, or formyl), thiocarbonyl (e.g., thioester, thiocarboxylate, or thioformate), amino, —N($R^b$)($R^c$), wherein each $R^b$ and $R^c$ is independently H or $C_1$-$C_6$ alkyl, cyano, nitro, —$SO_2$N($R^b$)($R^c$), —SOR$^d$, and S(O)$_2$R$^d$, wherein each $R^b$, $R^c$, and $R^d$ is independently H or $C_1$-$C_6$ alkyl. Illustrative substituents include, for example, those described herein above. The permissible substituents can be one or more and the same or different for appropriate organic compounds. This disclosure is not intended to be limited in any manner by the permissible substituents of organic compounds. It will be further understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The acidic compound (e.g., a compound of Formula (I), (II), or (III)) may adopt any stereoisomeric form or contain a mixture of stereoisomers. For example, the acidic compound may be a mixture of D,L-phosphoserine, or contain substantially pure D-phosphoserine or substantially pure L-phosphoserine. In many embodiments, the stereochemistry of acidic compound does not significantly impact the regeneration properties of the composition. In some embodiments, the particular stereochemistry of the organic phosphate or the ratio of stereoisomers of the acidic compound has a significant impact on the adhesive properties of the composition.

In some embodiments, the acidic compound (e.g., a compound of Formula (I), (II), or (III)) is present in an amount greater than or equal to about 0.1% (w/w) of the composition. In some embodiments, the acidic compound (e.g., a compound of Formula (I), (II), or (III)) is present in an amount greater than or equal to about 0.1% (w/w), about 0.5% (w/w), about 1% (w/w), about 3% (w/w), about 5% (w/w), about 10% (w/w), about 20% (w/w), about 30% (w/w), about 40% (w/w), about 50% (w/w), about 60% (w/w), about 70% (w/w), about 80% (w/w), about 90% (w/w), about 95% (w/w), or up to 100% of the composition.

In the present disclosure, the multivalent metal salts (e.g., calcium phosphates, calcium oxide or combinations thereof) may react with the acidic compounds to form an adhesive composition when combined with an aqueous medium. In some embodiments, the aqueous medium comprises water (e.g., sterile water), saliva, buffers (e.g., sodium phosphate, potassium phosphate, or saline (e.g., phosphate buffered saline)), blood, blood-based solutions (e.g., plasma, serum, bone marrow), spinal fluid, dental pulp, cell-based solutions (e.g, solutions comprising fibroblasts, platelets, odontoblasts, stem cells (e.g., mesenchymal stem cells) histiocytes, macrophages, mast cells, or plasma cells), or combinations thereof in the form of aqueous solutions, suspensions, and colloids. In some embodiments, the aqueous medium comprises sterile water, distilled water, deionized water, sea water, or fresh water.

In some embodiments, the aqueous medium comprises water from the environment, e.g., fresh water, salt water or brackish water from the oceans, seas, bays, rivers, streams, ponds or other moving or standing water sources.

The compositions described herein have a tacky state after mixing with an aqueous medium. This tacky property is retained for a number of minutes, e.g., up to 12 minutes, up to about 4 minutes, up to about 2 minutes, after mixing with the aqueous medium. In the tacky state, the compositions will adhere bone to bone and bone to other materials. The tacky state can allow the materials to be positioned or repositioned without appreciable loss of cured strength. In some embodiments, the tacky state is retained for a number of seconds, e.g., up to 60 seconds, up to 30 seconds, up to 20 seconds, up to 10 seconds.

In the putty state, which follows the tacky state, the compositions can be shaped or sculpted, for example to fill voids in bone. This putty state is retained for a number of minutes, e.g., up to 15 minutes, up to about 8 minutes, up to about 5 minutes, or up to about 3 minutes, after mixing with the aqueous medium.

The combined time of the tacky state and the putty state referred to as working time. Typical compositions have a working time of up to 8 minutes from initial mixing after which time the compositions have sufficiently begun hardening. After the putty state, the compositions may harden and the materials that have been affixed to each other cannot be separated without the application of significant force. The compositions typically will begin to harden within about 8 minutes, e.g., within about 5 minutes, after mixing with the aqueous medium. The described tacky, putty, and set state occur in a wet environment or dry environment.

In some embodiments, the compositions may further comprise an additive. An additive may be used to impart additional functionality to the composition of the disclosure, such as improving or affecting the handling, texture, durability, strength, or resorption rate of the material, or to provide additional cosmetic or medical properties. Exemplary additives may include a metal (e.g. copper, silver, gold, iron, titanium, aluminum, cobalt, chromium, tantalum), a metallic alloy (e.g. bronze, brass, stainless steel, cobalt-chromium), a salt (e.g., calcium phosphates (e.g., dicalcium phosphate, monocalcium phosphate, beta tricalcium phosphate, hydroxyapatite, alpha tricalcium phosphate), calcium sulfate, calcium carbonate, calcium bicarbonate, calcium iodide, barium sulfate, sodium carbonate, sodium bicarbonate, sodium chloride, potassium chloride), a pore forming agent (e.g., through release of gas (e.g., calcium carbonate, sodium carbonate, sodium bicarbonate) or through dissolution of a solid (e.g., sodium chloride, potassium chloride)), a humectant (e.g., sorbitol, or another hygroscopic compound), reducing or oxidizing agents, rust inhibitors, a polymeric alcohol (e.g., polyethylene glycol), a filler, a formulation base, a viscosity modifier (e.g., polyol (e.g., glycerol, mannitol, sorbitol, trehalose, lactose, glucose, fructose, or sucrose)), an abrasive, a coloring agent (e.g., a dye, pigment, or opacifier), a flavoring agent (e.g., a sweetener), a medication that acts locally (e.g., an anesthetic, coagulant, clotting factor, chemotactic agent, and an agent inducing phenotypic change in local cells or tissues), a medication that acts systemically (e.g., an analgesic, anticoagulant, hormone, vitamin, pain reliever, anti-inflammatory agent, chemotactic agent, or agent inducing phenotypic change in local cells or tissues), an antimicrobial agent (e.g., an antibacterial, antiviral, antifungal agent), an antifouling agent (e.g., copper, silver, or other transition metal salts) or a combination thereof. In some embodiments, the additive comprises a polymer. The biologically active substances (e.g., medicines, drugs) in the categories above might include active substances or precursors, which become biologically active upon modification after interaction with the surrounding environment. The biologically active substances might include a stem cell (e.g., an embryotic, adult, induced pluripotent, or mesenchymal stem cell) or bone tissue components (e.g., autograft, allograft, xenograft). The substances might be synthetic, semisynthetic, or biologically derived (e.g., peptides, proteins, or small molecules). The substances might include, but not be limited to an anti-inflammatory compound (e.g., a steroid, nonsteroidal anti-inflammatory drug, or cyclooxygenase inhibitor), a complement protein, a bone morphogenic factor or protein, a hormone active locally or systemically (e.g., parathyroid hormone, calcitocin, or prostoglandin), or other small molecule (e.g., a calciferol, secosteroids).

In some embodiments, the additive is a polymer. Suitable polymers incorporated as additives into the adhesive composition may contain functional groups that contains electronegative atoms as the bonding sites of the polymer surfaces to the available metal ions, such as electronegative carbonyl oxygen atom(s) of the ester group or electronegative nitrogen atom(s) of the amine group as the bonding sites of the polymer surfaces to the available metal ions. These functional groups can be either in the backbone chain of the polymer or in groups pendant to the polymer chain. These polymeric based compounds may include, but are not limited to, one or more of the following; poly(L-lactide), poly(D,L-lactide), polyglycolide, poly(□-caprolactone), poly(teramethylglycolic-acid), poly(dioxanone), poly(hydroxybutyrate), poly(hydroxyvalerate), poly(lactide-co-glycolide), poly(glycolide-co-trimethylene carbonate), poly(glycolide-co-caprolactone), poly(glycolide-co-dioxanone-co-trimethylenecarbonate), poly(tetramethylglycolic-acid-co-dioxanone-co-trimethylenecarbonate), poly(glycolide-co-caprolactone-co-lactide-co-trimethylenecarbonate), poly(hydroxybutyrate-co-hydroxyvalerate), poly(methylmethacrylate), poly(acrylate), polyamines, polyamides, polyimidazoles, poly(vinyl-pyrrolidone), collagen, silk, chitosan, hyaluronic acid, gelatin and/or mixtures thereof. In addition, copolymers of the above homopolymers also can be used. Additionally, suitable polymers used as an additive might comprise those that are capable of conducting electricity (e.g., polypyrrole, polyaniline, polyacetyline, poly-p-phenylene, poly-p-phenylene-vinylene, polythiophene, and hemosin).

The general structural nature of a polymer (e.g., a polymer used as an additive in an adhesive composition described herein) may include a linear homo and copolymer, a cross linked polymer, a block polymer, a branched polymer, a hyper branched polymer, or a star shaped polymer. The polymers can be added to the formulation in the form of a solution, powder, fiber, resin, liquid crystal, hydrogel, chip, flake, and the like. The polymeric material can be included directly within the adhesive composition or can be an adjunct that is applied in situ as the cement is applied to the bone.

In some embodiments, the adhesive composition comprises a plurality of said additives. In some embodiments, certain additives may be provided as powders or granules or solutes or any combination thereof. These powders may exhibit a mean particle size of about 0.001 to about 0.250 mm, about 0.005 to about 0.150 mm, about 0.25005 to about 0.75075 mm, 0.25 to about 0.5010 to about 0.050 mm, about 0.015 to about 0.025 mm, about 0.020 to about 0.060 mm, about 0.020 to about 0.040 mm, about 0.040 to about 0.100 mm, about 0.040 to about 0.060 mm, about 0.060 to about 0.150 mm, or about 0.060 to about 0.125 mm. The mean particle size may be bi-modal to include any combination of mean particle sizes as previously described. These granules may exhibit a mean granule size of about 0.050 mm to about 5 mm, about 0.100 to about 1.500 mm, about 0.125 to 1.000 mm, 0.125 to 0.500 mm, about 0.125 to 0.250 mm, about 0.250 to 0.750 mm, about 0.250 to 0.500 mm, about 0.500 to 1.00 mm, about 0.500 to 0.750 mm. The mean granule size may be multi-modal to include any combination of mean granule sizes as previously described. In some embodiments, varying sizes of said powders or granules may be used in the adhesive composition. The form of the granules may be roughly spherical, roughly prolate ellipsoidal, roughly oblate ellipsoidal. The form may approximate flakes, plates, rods, or products of random fracture or crushing, e.g., shards, cracked crusts, or shapes of boulders, gravel, crushed rock, etc, In some embodiments, certain additives may be provided as fibers. In some embodiments, the fibers may exhibit a mean fiber diameter of about 0.010 mm to about 2 mm, about 0.010 mm to about 0.50 mm, or about 0.025 mm to about 0.075 mm. These fibers may exhibit a mean fiber length of about 0.025 mm to about 50.0 mm, about 0.50 mm to 10 mm, or about 1.00 mm to about 3.50 mm. The mean fiber diameter or length may be multi-modal to include any combination of mean fiber diameter or length.

Methods of Use

The present disclosure features methods of using an implantable object, a guiding device, a recipient site preparation instrument, or s, In some embodiments, the guiding device is used to shape a bone-implantable material to a desired outcome (e.g., a desired shape or size). In some embodiments, the guiding device defines the volume to be occupied by the bone-implantable material. In some embodiments, the guiding device defines the desired shape of the bone-implantable material. In some embodiments, the guiding device defines the volume to be excluded from a space (i.e., block out, retract, etc.). In some embodiments, the guiding device serves as a barrier to prevent the spread of the bone-implantable material. In some embodiments, the guiding device prevents contact of the bone-implantable material with a critical structure, e.g., a nerve, a blood vessel, or a duct.

In some embodiments, the guiding device is used to compress the bone-implantable material to the implantation site (e.g., into bone, or onto or in between bone surfaces). In some embodiments, the guiding device is capable of compressing the bone-implantable material to the implantation site (e.g., into bone, or onto or in between bone surfaces).

In some embodiments, the guiding device is used to dam or prevent the bone-implantable material from spreading to a specific area.

In some embodiments, the guiding device is released from the bone-implantable material. In some embodiments, the guiding device adheres to the bone-implantable material.

In some embodiments, the guiding device remains in use during the closure of a wound. In some embodiments, the guiding device is removed prior to the closure of a wound. In some embodiments, the guiding device is used and remains in situ after the closure of a wound.

In some embodiments, the guiding device is applied at the site of action during a diagnostic or surgical procedure. In some embodiments, the guiding device is used repeatedly for similar purpose (e.g., during oncological irradiation procedures) and removed each time the procedure is completed. In some embodiments, the guiding device is used repeatedly for different purposes (e.g., to hold a pattern for osteotomies during craniotomy and then again for holding the cranial flap, or its replacement implant, during its fixation after the intracranial procedure or calvarial resection is completed). In some embodiments, the guiding device remains at the site of application as means of external fixation during a healing period.

In some embodiments, the guiding device is used to hold, in an unambiguous relationship to tissues, an instrument used in performance of a procedure (e.g., a soft tissue cutting instrument, a hard tissue cutting instrument, a radiation source, etc.). In some embodiments, the guiding device is used to hold, in an unambiguous relationship to the tissues, an instrument used in performance of an intracranial procedure or spinal procedure. In some embodiments, the guiding device is used to hold or secure a bone-shaping instrument in an unambiguous relationship to a bone. In another aspect, the present disclosure features a method of use of a guiding device for the placement of an implantable object. In some embodiments, the method comprises use of a guiding device for the placement of an implantable object into a bone-implantable material.

In some embodiments, the guiding device is used to hold an implantable object. In some embodiments, the guiding device is capable of holding one or more implantable objects. In some embodiments, the guiding device is capable of holding one or more implantable objects in a geometrically defined manner.

In some embodiments, the method comprises use of a guiding device to hold the implantable object in a geometrically defined manner to a bone-implantable material. In some embodiments, the method comprises use of a guiding device to hold the implantable object in a geometrically defined manner to a bone-implantable material during the application of said bone-implantable material. In some embodiments, the method comprises use of a guiding device to hold the implantable object in a geometrically defined manner while a bone-implantable material is curing, e.g., becoming substantially solid. In some embodiments, the method comprises use of a guiding device to hold the implantable object in a geometrically defined manner to an element, e.g., reference element, orientation element, retention element, while the bone-implantable material is curing, e.g., becoming substantially solid. In some embodiments, the method comprises use of a guiding device to hold the implantable object in a geometrically defined manner while the adhesive bond of the bone-implantable material to the implantable object is forming. In some embodiments, the method comprises use of a guiding device to hold the implantable object in a geometrically defined manner while the adhesive bond of the bone-implantable material between the implantable material and a bone is forming.

In some embodiments, the method comprises use of a guiding device to hold the implantable object in a geometrically defined manner while the bone-implantable material is applied (e.g., injected) to the space between the implantable object and a bone. In some embodiments, the method comprises use of a guiding device to hold the implantable object in a geometrically defined manner, wherein the guiding device allows for the adjustment of the position of the implantable object relative to the guiding device. In some embodiments, the method comprises use of a guiding device to hold the implantable object in a geometrically defined manner, wherein the guiding device allows for the adjustment of the position of the implantable object relative to the guiding device and its retention elements. In some embodiments, the adjustment of the position occurs in the rotational, translational, or angular dimensions relative to the guiding device.

In some embodiments, the method comprises detection of the relative position and orientation of the implantable component. In some embodiments, the detection of the relative position and orientation of the implantable component comprises use of a radiopaque element (e.g., reference element). In some embodiments, the implantable object comprises the radiopaque element. In some embodiments, the method comprises detection of the relative position and orientation of the elements of the implantable object or the implantable component that remain above or outside of the bone.

In some embodiments, the method further comprises recording the relative position and orientation of the implantable component. In some embodiments, the method further comprises observing the relative position and orientation of the implantable component.

In some embodiments, the method comprises determination of the spatial relationship between the positions of the implantable components observed. In some embodiments, the method comprises determination of the spatial relationships between the position of the implantable component and certain tissues recorded in the field. In some embodiments, the certain tissues comprise skeletal elements and the investing soft tissues, e.g., nerves, cartilage, ligaments, tendons and muscle. In some embodiments, the skeletal elements comprise the bones of the spine, the skull, the mandible, the pelvic and pectoral girdles, and extremities. In some embodiments, the tissues comprise the diaphyses and metaphyses of the long bones, the jaws, the bones of the face, the bones of the cranium, the bones of the base of the skull, the bones of the spine, the innominate bone, the bones of the wrist, the bones of the knee, the bones of the elbow, the bones of the shoulder, the bones of the wrist, the bones of the ankle, and other bones.

In some embodiments, the method comprises determination of the spatial relationships between the implantable components observed radiographically and relating these relationships to said implantable component in the patient. In some embodiments, the method comprises determination of the spatial relationships between the implantable component observed radiographically and relating these relationships to said implantable component in a physical representation of the patient (e.g., a cast or model of the patient).

In some embodiments, the method comprises construction of a model of the spatial relationships between the implantable component observed and the tissues recorded in the field. In some embodiments, the model is a virtual model or a physical model. In some embodiments, the method comprises use of a model (e.g., a virtual model or a physical model) to construct a reference framework relating the implantable component to the imaged field. In some embodiments, the model is a virtual model or a physical model. In some embodiments, the method comprises use of a model (e.g., a virtual model or a physical model) to construct a reference framework relating the implantable component to another implantable component.

In some embodiments, the method further comprises the use of a reference framework to plan surgical treatment. In some embodiments, the surgical treatment comprises the placement of the implantable object. In some embodiments, the surgical treatment comprises the placement of more than one implantable object. In some embodiment, the surgical treatment comprises the placement of a bone graft. In some embodiment, the surgical treatment comprises the placement of a dental implant.

Figure 9:
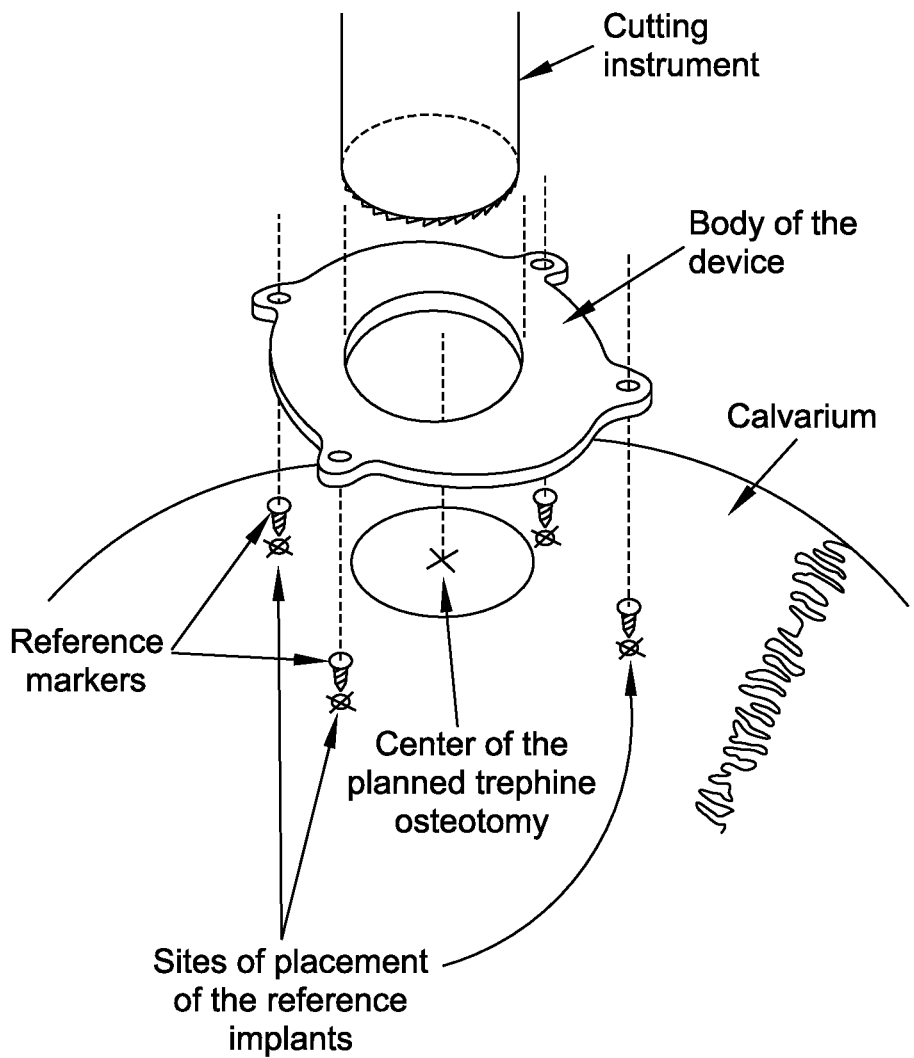
FIG. 9 is an illustration of an exemplary multi-component guiding device (e.g., form or guide) in use with exemplary guiding device implantable components (e.g., mini-implant) serving as reference elements to relate and attach the guiding device bridging component to a bone site (e.g. calvarium) in a substantially immobile geometrically defined manner in use with exemplary cutting instruments for trephine osteotomy.

In some embodiments, the method further comprises construction of a guiding device for surgical incising, cutting, milling or drilling, chipping, abrading, or the like, or other means of modification of the shape of a tissue as shown in FIG. 9. In some embodiments, the method comprises use of the reference framework to construct a guiding device for relating an implantable object (e.g., calvarial segment implant replacing resected diseased tissue) to the tissues in the field. In some embodiments, the method comprises the use of the reference framework to construct a guiding device for relating an implantable object to another implantable object, or more than one implantable object.

In some embodiments, the method comprises the use of the reference framework to construct a guiding device for relating an anatomical object being replaced to its original position prior to its removal (e.g., cranial flap in the context of a brain surgery) In some embodiments, the method comprises use of the reference framework to construct a guiding device for relating an anatomical object being replaced to a planned location different from its original anatomical position (e.g., facial bone segment during orthognathic procedure, e.g., sagittal split osteotomy).

In some embodiments, the method comprises the use of the reference framework above to construct a guiding device that contacts, attaches to, is retained by, or otherwise physically relates to an implantable component or an implantable object, e.g., reference, orientation, or retention element. In some embodiments, the method comprises use of an implantable object retention element to precisely attach, retain, or otherwise physically relate the guiding device to certain tissues.

In some embodiments, the method comprises the use of a shape replica or analog of an implantable object in the physical form of a model to represent the reference elements corresponding to virtual reference points. In some embodiments, the method comprises use of an elastically deformable component for retention of the guiding device to a reference element. In some embodiments, the method comprises the use of frictional resistance for retention of the guiding device to an element, e.g., orientation or retention element. In some embodiments, the method comprises the use of magnetic force for retention of the guiding device to an element, e.g., orientation or retention element. In some embodiments, the method comprises the use of chemical adhesion for retention of the guiding device to an element.

In some embodiments, an existing reference element comprises a tooth or teeth, or other hard and non-displaceable object in the field of interest.

In some embodiments, the method comprises the use of resilient materials as components of the guiding device. In some embodiments, the resilient materials contact the retention elements of the implantable component or implantable reference element. In some embodiments, the resilient materials mechanically engage the retention elements of the implantable component or implantable reference element. In some embodiments, the mechanical engaging comprises a precise locking of the subcomponents of one or more of the implantable components or implantable reference element with the guiding device. In some embodiments, the resilient subcomponents comprise a synthetic polymer (e.g., rubber, elastomer, PGA, or PLGA) or a naturally occurring polymer (e.g., collagen, a modified collagen, or a gelatin). In some embodiments, the resilient subcomponents comprise elastic metal subcomponents.

In some embodiments, the method comprises the use of magnetic force.

In some embodiments, the method comprises precisely observing the relationship between the guiding device and the implantable component or an implantable reference element. In some embodiments, the method comprises precisely observing the relationship between the guiding device and the implantable component or an implantable reference element with certain tissues.

In some embodiments, the method comprises attaching additional objects, instruments, or devices to the guiding device in a defined planned relationship to the implantable component or implantable reference element. In some embodiments, the method comprises attaching additional objects, instruments (e.g., cutting instruments, radiation source, etc.), or devices (e.g., prosthetic joint parts, stump prosthesis implants, cochlear implants, etc.) to the guiding device in a defined planned relationship to certain hard (e.g., the innominate bone, proximal femur metaphysis or diaphysis, distal femur, humerus or tibia, the jaws, teeth, the bones of the spine, bones of the cranium, bones of the wrist or the ankle, the bones of the hand or the foot, etc.) or soft (e.g., the brain, the spinal cord, the eye, the gums, and other soft tissues immobilized by surrounding or nearby hard tissues) tissues by making use of the defined planned relationship between the guiding device and the implantable component or implantable reference element.

In some embodiments, the method comprises precisely relating surgical cutting instruments to certain tissues by using the defined and planned precise relationship to the implantable component or implantable reference element. In some embodiments, the method comprises precisely relating graft deposits to certain tissues by using the defined and planned precise relationship to the implantable component or implantable reference element.

In some embodiments, the method comprises precisely relating graft delivering, graft containing, graft forming, graft shaping or otherwise graft handling devices to certain tissues by using the defined and planned precise relationship to the implantable component or implantable reference element. In some embodiments, the method comprises precisely relating implants, implant holders, implant carriers, or other implant handling devices to the tissues by using the defined and planned precise relationship to the implantable component or implantable reference element. In some embodiments, the method comprises precisely relating implants, implant holders, implant carriers, or other implant handling devices to the tissues and to each other by using the defined and planned precise relationship to the implantable component or implantable reference element. In some embodiments, the precisely relating comprises relation in a rotational axis and translational axis. In some embodiments, the precisely relating comprises relation in all three rotational axes and all three translational axes.

Figure 5:
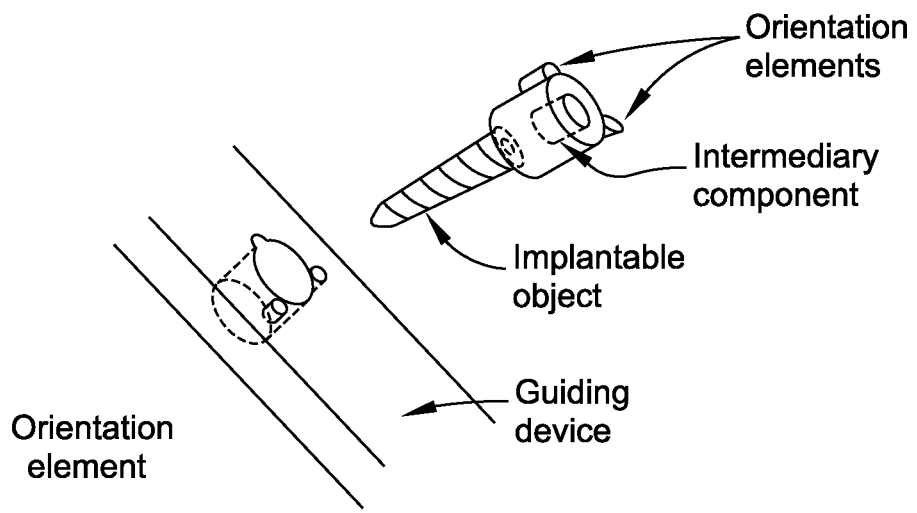
FIG. 5 is an illustration of an exemplary multi-component guiding device (e.g., form or guide) as used in a dental setting. The illustration depicts the insertion of an exemplary implantable object attached to an intermediary component of the guiding device and inserted using said bridging component of the guiding device, and highlights optional rotational indices as orientation elements.

In some embodiments, the method comprises a firm, unambiguous, and rotationally indexed attachment of the implantable object to the guiding device prior to attaching the guiding device to an implantable reference element. In some embodiments, the method comprises a firm, unambiguous, and rotationally indexed attachment of the guiding device to an implantable reference element prior to relating the implantable object to the guiding device. In some embodiments, the method comprises relating and orienting the implantable object to the guiding device by interlocking of features of the guiding device to features of the implantable object or an attached intermediary component (e.g., carrier) thereof in a rotationally indexed and unambiguous spatial relationship as shown in FIG. 5.

In some embodiments, the method comprises confirming the planned placement of the implantable object through the use of the precise relationship between the implantable reference element and each of the implantable objects being implanted.

In some embodiments, the method comprises fabrication of restorative devices in defined planned precise relationship to the tissues and anticipated functional relationships to the implantable object or implantable reference element. In some embodiments, the restorative devices are temporary or used on an interim basis. In some embodiments, the restorative devices are definitive. In some embodiments, the restorative devices are dental restorations. In some embodiments, the restorative devices are maxillofacial restorations. In some embodiments, the restorative devices are orthopedic prostheses. In some embodiments, the restorative devices are artificial joint elements. In some embodiments, the restorative devices are limb prosthesis elements. In some embodiments, the restorative devices are prostheses aiding in hearing or vision.

In some embodiments, the guiding device indirectly or directly holds an implantable object in a defined spatial relationship to another object. In some embodiments, the guiding device directly or indirectly holds an implantable object in a defined spatial relationship to another object just prior to and/or during the attachment of an implantable object to the bone. In some embodiments, the attachment to bone is in the form of luting, adhering or cementation into the desired position in the bone.

Figure 8A:
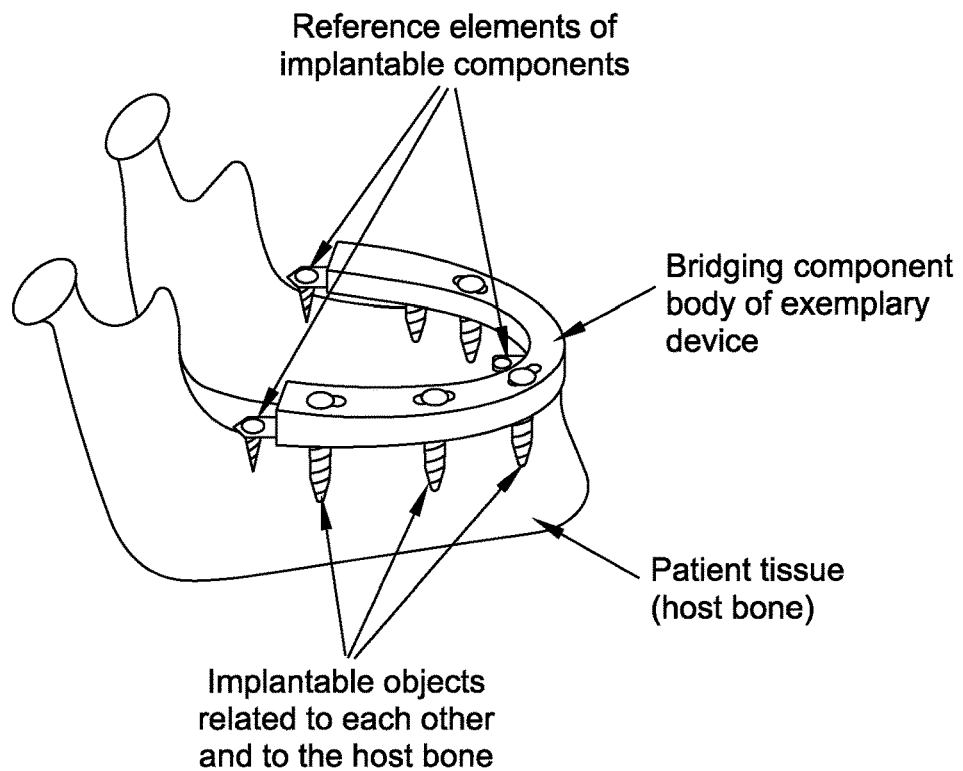
FIG. 8A is an illustration of an exemplary multi-component guiding device (e.g., form or guide) in use with exemplary guiding device implantable components (e.g., mini-implant) serving as reference elements to relate the guiding device bridging component to a bone site (e.g. host tissue) in a substantially immobile geometrically defined manner in use with exemplary implantable objects to be attached to the host bone surfaces, as used in a dental setting.
Figure 8B:
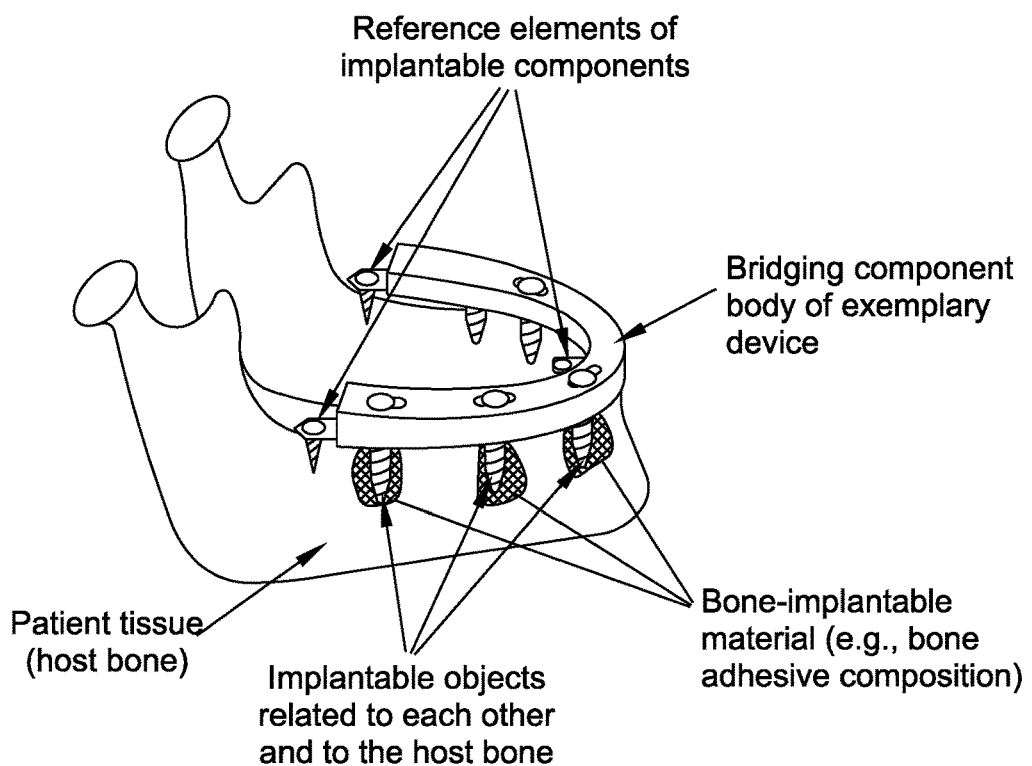
FIG. 8B is an illustration of an exemplary multi-component guiding device (e.g., form or guide) in use with exemplary guiding device implantable components (e.g., mini-implant) serving as reference elements to relate the guiding device bridging component to a bone site (e.g. host tissue) in a substantially immobile geometrically defined manner in use with exemplary implantable objects and an exemplary bone-implantable material, (e.g., adhesive composition) applied to stabilize implantable objects to the host bone surfaces, as used in a dental setting.

In some embodiments, the guiding device indirectly or directly holds an implantable object in a defined spatial relationship to another object. In some embodiments, the guiding device indirectly or directly holds one or more implantable objects in a defined spatial relationship to another object as depicted in FIG. 8A. In some embodiments, the implantable object is used with a guiding device and a bone-implantable material (e.g., adhesive composition) in a dental setting and comprises the features and characteristics depicted in FIG. 8B.

In some embodiments, the guiding device holds an implantable object in a geometrically defined manner. In some embodiments, the guiding device holds an implantable object in a geometrically defined manner in reference to a rotational axis or a translational axis. In some embodiments, the guiding device holds an implantable object in a geometrically defined manner in reference to one or more rotational axes (e.g., all three rotational axes) or one or more translational axes (e.g., all three translational axes).

In some embodiments, the guiding device holds an implantable object in a geometrically defined manner relative to a reference marker. In some embodiments, the guiding device holds an implantable object in a geometrically defined manner relative to another device. In some embodiments, the guiding device holds an implantable object in a geometrically defined manner relative to one or more dental restorations. In some embodiments, the guiding device holds an implantable object in a geometrically defined manner relative to a dental implant or restorations of said dental implants.

In some embodiments, the guiding device holds more than one implantable object in a geometrically defined manner. In some embodiments, the guiding device holds more than one implantable object in a geometrically defined manner in reference to a rotational axis or a translational axis. In some embodiments, the guiding device holds more than one implantable object in a geometrically defined manner in reference to one or more rotational axes (e.g., all three rotational axes) or one or more translational axes (e.g., all three translational axes). In some embodiments, the guiding device holds more than one implantable object in a geometrically defined manner relative to a reference marker. In some embodiments, the guiding device holds more than one implantable object in a geometrically defined manner relative to another device. In some embodiments, the guiding device holds more than one implantable object in a geometrically defined manner relative to one or more dental restorations. In some embodiments, the guiding device holds more than one implantable object in a geometrically defined manner relative to a dental implant or restorations of said dental implants.

In some embodiments, the guiding device holds the implantable object directly. In some embodiments, the guiding device holds the implantable object directly by application of retention elements through mechanical fixation. In some embodiments, mechanical fixation comprises compression force (e.g., friction), screw fixation, plastic deformation, elastic deformation, or magnetic force retention.

In some embodiments, the orientation elements of a guiding device component define the rotational positions possible for mating other components of the guiding device. In some embodiments, the number of rotational positions is equal to m, in which one guiding device component mating interface to another guiding device component possesses m-fold radial symmetry. In some embodiments, the integer m can be a range from 1 to 20. The defined rotational position of the orientation element allows defined placement of components of a guiding device. In some embodiments, one-fold symmetry is preferred for unambiguous placement of a guiding device component to another guiding device component.

In some embodiments, the orientation elements of the guiding device define the rotational positions possible for mating other devices (e.g., an implantable object, an instrument). In some embodiments, the number of rotational positions is equal to m, in which the guiding device mating interface to the device possesses n-fold radial symmetry. In some embodiments, the integer n can be a range from 1 to 20. The defined rotational position of the orientation element allows defined placement of a device or devices. In some embodiments, one-fold symmetry is preferred for unambiguous placement of a device or devices.

In some embodiments, the guiding device and the implantable object are separated by removal of the mechanical fixation. In some embodiments, the mechanical fixation is released through rotation, compression, or translation of the retention element. In some embodiments, the fixation is released through deformation of the retention element. In some embodiments, the fixation is released through the use of mechanical force to deform an element (e.g., spring, snap, o-ring, or clip). In some embodiments, the fixation is released through a change in the thermodynamic state of the retention element, e.g., through the addition or removal of heat. In some embodiments, the removal of the mechanical fixation may include a change in the crystal lattice or state (e.g., solid to liquid) of the retention element.

In some embodiments, the guiding device holds the implantable object indirectly. In some embodiments, the guiding device holds the implantable object indirectly through attachment to an intermediary component that is attached to the implantable object by application of retention elements through mechanical fixation. In some embodiments, mechanical fixation comprises compression force (e.g., friction), screw fixation, plastic deformation, elastic deformation, or magnetic force retention. In some embodiments, the intermediary component is a carrier, a retention aid, a keeper, a screw, or a clip. In some embodiments, the intermediary component is a healing abutment or a prosthetic abutment. In some embodiments, the intermediary component comprises an orientation element. In some embodiments, the intermediary component remains in place after implantation. In some embodiments, the intermediary component is removed after implantation. In some embodiments, the intermediary component provides mechanical fixation to the guiding device or the implantable object. In some embodiments, the mechanical fixation is made without releasing the intermediary component from the guiding device. In some embodiments, the mechanical fixation is released without releasing the intermediary component from the guiding device. In some embodiments, the mechanical fixation is made without releasing the intermediary component from the implantable object. In some embodiments, the mechanical fixation is released without releasing the intermediary component from the implantable object. In some embodiments, the orientation elements of the intermediary component and the guiding device define the rotational positions possible for mating other devices (e.g., an implantable object). In some embodiments, the number of rotational positions is equal to p, in which the intermediary component mating interface to the guiding device possesses p-fold radial symmetry. In some embodiments, the integer p can be a range from 1 to 20. The defined rotational position of the orientation element allows defined placement of a device or devices. In some embodiments, one-fold symmetry is preferred for unambiguous placement of a device or devices.

In some embodiments, the guiding device and the intermediary component or the intermediary component and the implantable object are separated by removal of the mechanical fixation. In some embodiments, the mechanical fixation is released through rotation, compression, or translation of the retention element. In some embodiments, the fixation is released through deformation of the retention element. In some embodiments, the fixation is released through the use of mechanical force (e.g., spring, snap, o-ring, or clip). In some embodiments, the fixation is released through a change in the thermodynamic state of the retention element, e.g., through the addition or removal of heat. In some embodiments, the removal of the mechanical fixation may include a change in the crystal lattice or state (e.g., solid to liquid) of the retention element.

In some embodiments, the intermediary component occludes sections of the external surface of the implantable object. In some embodiments, the intermediary component prevents materials and instruments from contacting sections of the implantable object. In some embodiments, the intermediary component gives shape to a material that is in the process of hardening (e.g., curing, e.g., a bone-implantable material) while in contact with the material.

In some embodiments, the guiding device holds the implantable object in a geometrically defined manner within an implantation site (e.g., into bone, or onto or in between bone surfaces) to facilitate application of a bone-implantable material. In some embodiments, the guiding device holds the implantable object in a geometrically defined manner through the engagement of orientation or retention elements during the application of said bone-implantable material (e.g., adhesive composition) into the space between bone and the implantable object. In some embodiments, the guiding device holds the implantable object substantially immobile and in a geometrically defined manner while a bone-implantable material is curing, e.g., becoming substantially solid. In some embodiments, the guiding device holds the implantable object substantially immobile and in a geometrically defined manner to a reference element while the bone-implantable material is curing, e.g., becoming substantially solid. In some embodiments, the guiding device holds the implantable object substantially immobile and in a geometrically defined manner while the adhesive bond of the bone-implantable material to the implantable object is forming. In some embodiments, the guiding device holds the implantable object substantially immobile and in a geometrically defined manner while the adhesive bond of the bone-implantable material between the implantable material and a bone is forming.

In some embodiments, the guiding device holds the implantable object substantially immobile and in a geometrically defined manner while the bone-implantable material is applied (e.g., injected) to the space between the implantable object and bone. In some embodiments, the guiding device holds the implantable object in a geometrically defined manner and allows for the adjustment of the position of the implantable object relative to the guiding device. In some embodiments, the guiding device holds the implantable object in a geometrically defined manner and allows for the adjustment of the position of the implantable object relative to the guiding device and its retention elements. In some embodiments, the adjustment of the position occurs in the rotational, translational, or angular dimensions relative to the guiding device.

In some embodiments, the guiding device comprises an element (e.g., orientation, reference, retention) on an implantable component or a plurality of elements on implantable components that is surgically placed into or onto hard tissue in order to design and fabricate the bridging structure component of the guiding device for use in a future diagnostic, medical or surgical procedure. In some embodiments, the reference element of the implantable component is used during the collection of anatomical records from a patient. In some embodiments, the orientation element also serves as a retention element that is used as a physical point of attachment for the guiding device during a surgery or medical procedure. In some embodiments, the reference element and retention element are the same. In some embodiments, the orientation element is used in the absence of a hard, radio-dense reference point, or in the absence of hard tissues, for example, in the absence of teeth in the vicinity of the area of interest (e.g., in the edentulous maxilla) during any phase of the diagnostic workup or the surgery or medical procedure itself. Examples of such instances include, but are not limited to, flapless surgery in the edentulous maxilla, retaining and positioning of cutting instruments during a craniotomy or intracranial procedures, ophthalmological procedures, spine surgery, or other applications requiring precise incisions or implant placement (e.g., those that might involve the ossicular chain, maxillofacial prostheses, or more precise placement of prosthetic joint articulation surfaces) that may be recognized or known to those practiced in the art.

In some embodiments, the orientation element comprises rigid material. In some embodiments, the orientation element comprises elastic material. In some embodiments, the orientation element is rigidly held by the tissues. In some embodiments, the orientation element is rigidly held by the tissues for a period of time, e.g., at least as long as the surgery or medical procedure or longer, e.g., for several minutes, hours, days, months, or years after the surgery or medical procedure.

In some embodiments, the orientation element is capable of load bearing under physical contact. In some embodiments, the orientation element exhibits a load-bearing capacity of greater than about 0.5 MPa, e.g., about 1.0 MPa, about 1.5 MPa, about 2.0 MPa, about 3.0 MPa, about 5.0 MPa, about 10.0 MPa, or more.

In some embodiments, the implantable object ranges in size from about 0.1 mm to about 30 cm in any given dimension. In some embodiments, the implantable object is between about 0.1 mm to about 10 mm, e.g., about 0.1 mm, 0.25 mm, about 0.5 mm, about 0.75 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, or about 10 mm. In some embodiments, the implantable object is between about 1 mm and about 10 cm, e.g., about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 1 cm, about 2 cm, about 3 cm, about 4 cm, about 5 cm, about 6 cm, about 7 cm, about 8 cm, about 9 cm, about 10 cm, about 15 cm, about 25 cm or about 30 cm.

Figure 14A:
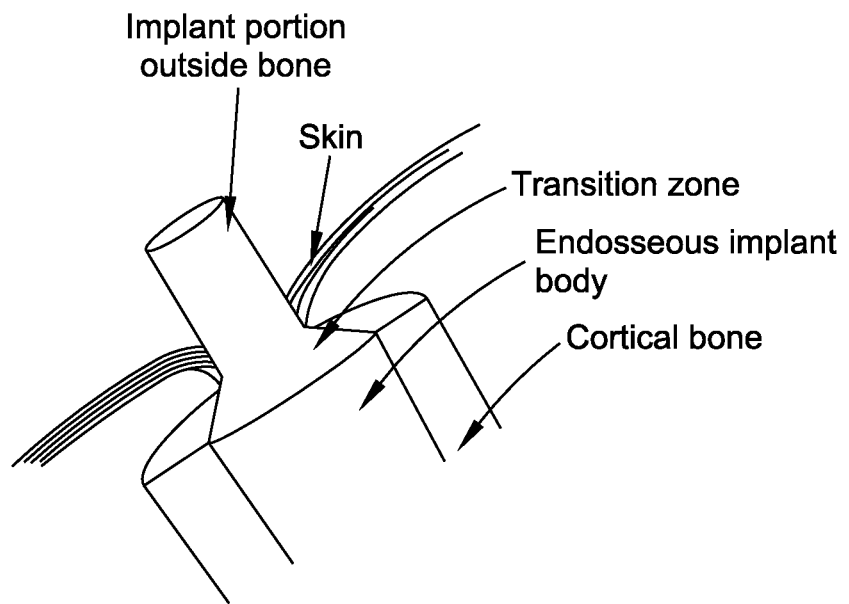
FIG. 14A illustrates an embodiment of a transdermal endosseous implantable object which comprises a "platform-switching" transition zone in a partial cutaway view. The broader endosseous part of the implantable object mechanically engages the bone with the optional use of a bone-implantable material (e.g., adhesive composition), while the narrower superficial part emerges transdermally for an attachment to a prosthesis, for example. The transition zone provides a favorable contour for soft tissue cuff attachment, easing cleaning.
Figure 14B:
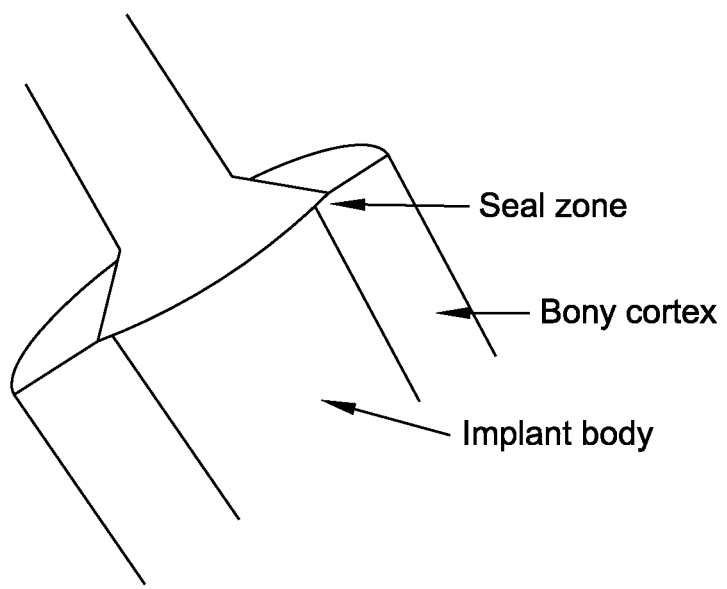
FIG. 14B illustrates a variant of the geometry of the transdermal endosseous implantable object in the previous figure which allows for a diminished thickness of the bone-implantable material (e.g., adhesive composition) at the seal zone by the means of a small widening of the transition zone surface as compared to the implantable object body diameter. Such a feature would provide a positive seat for the implantable object against a flat surface of the bone stump and limit the thickness of the adhesive composition grout seam.
Figure 14C:
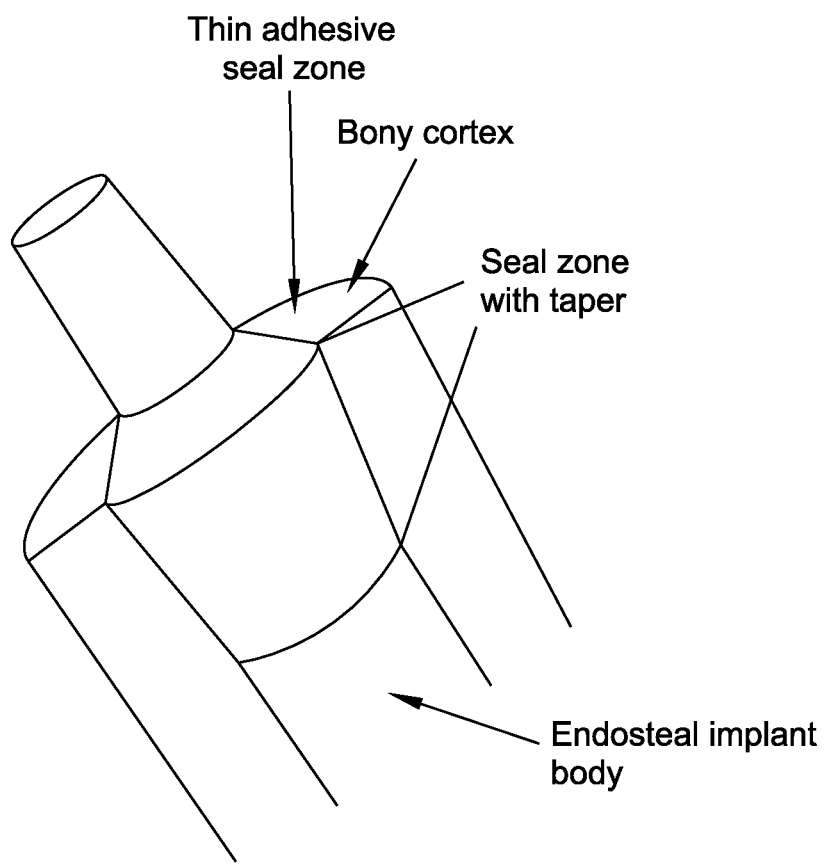
FIG. 14C illustrates a variant in the geometry of the transdermal endosseous implantable object fit to the implantation site to limit the bone-implantable material (e.g., adhesive composition) seam thickness at exit point from the endosseous space. This variant uses a taper, a conic frustum surface to accomplish the diminution of the film thickness on seating in disproportion to the gap around the implantable object body proper.
Figure 15A:
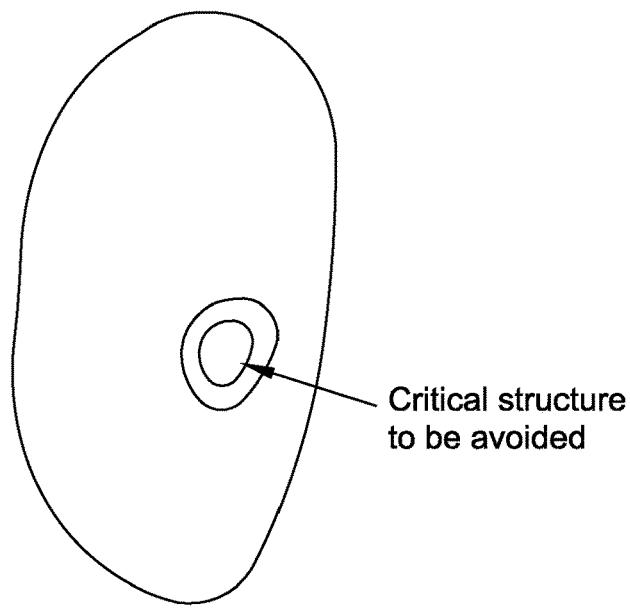
FIG. 15A. illustrates a cross-sectional image of an implantation site with a critical structure, e.g., nerve, blood vessel, coursing through it.
Figure 15B:
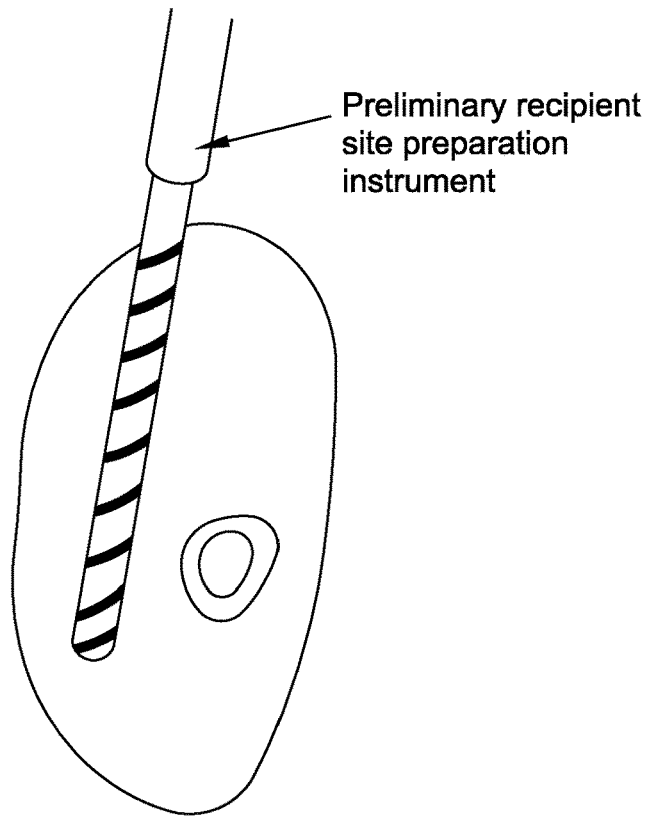
FIG. 15B illustrates an implantation site with preliminary site preparation instrument at the site of its action.
Figure 15C:
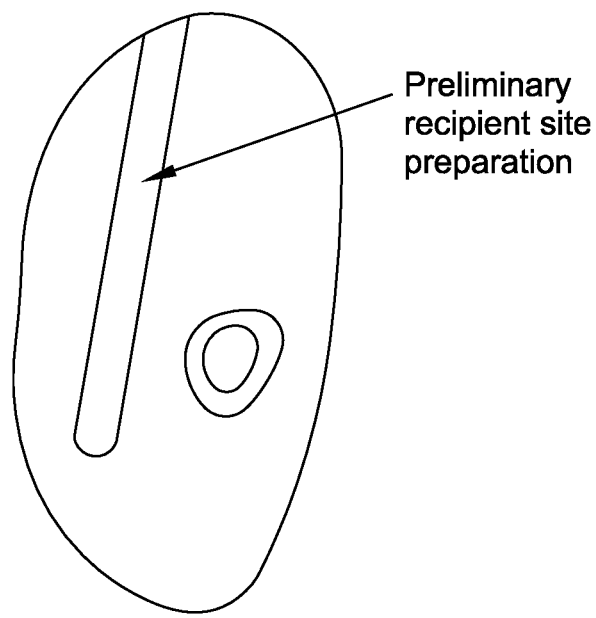
FIG. 15C illustrates the preliminary recipient site preparation.
Figure 15D:
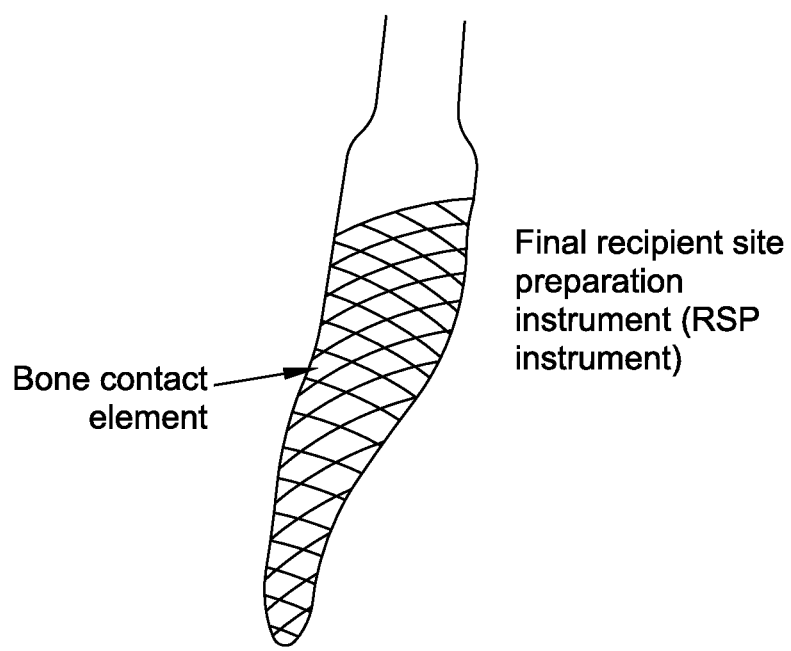
FIG. 15D illustrates a view of the Recipient Site Preparation (RSP) instrument illustrating the bone-contacting element.
Figure 15E:
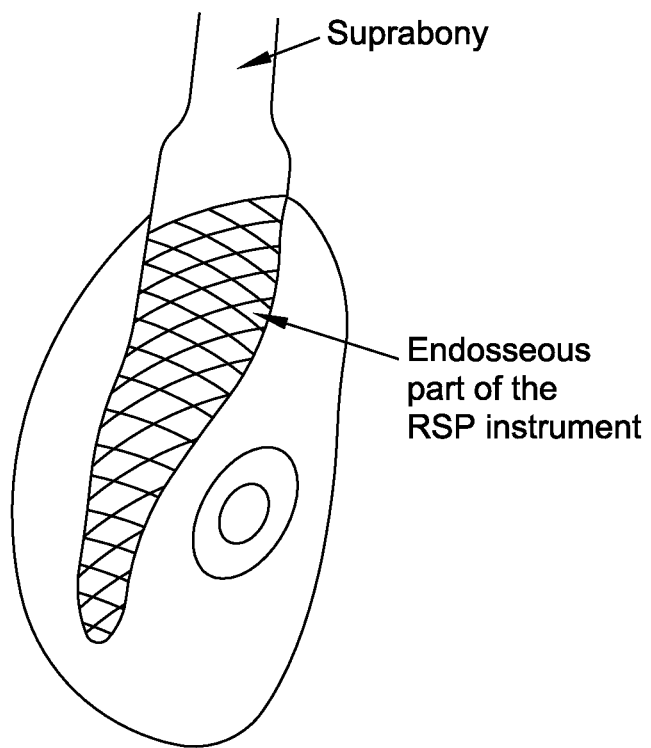
FIG. 15E illustrates a view of the RSP Instrument at the site of its action demonstrating the design of the shape resulting in avoidance of the critical structure
Figure 15F:
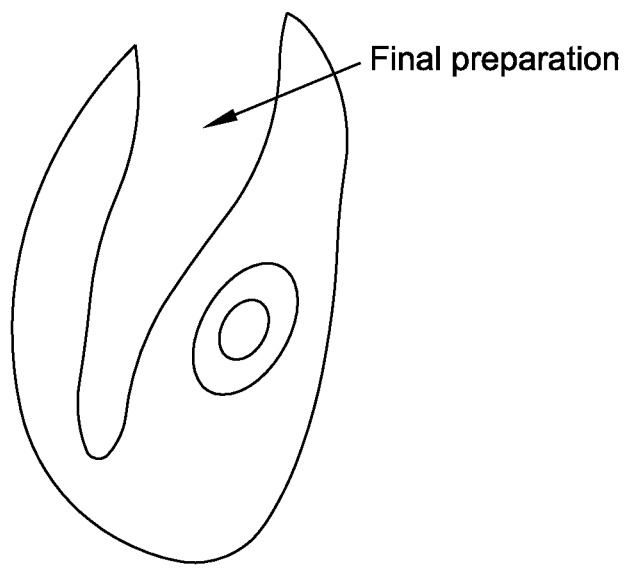
FIG. 15F illustrates a cross-sectional view of the Recipient Site in its completed state.
Figure 15G:
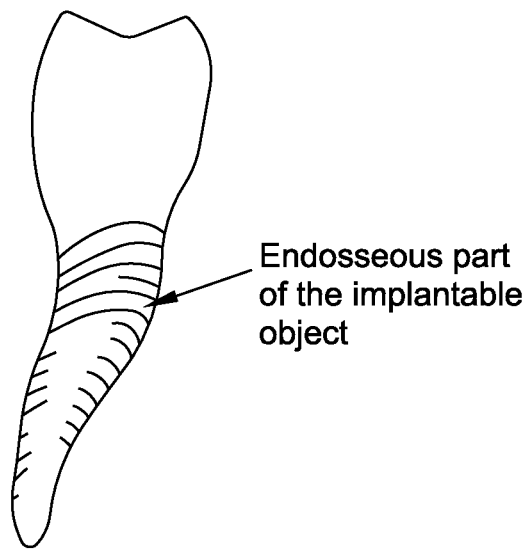
FIG. 15G illustrates a view of the implantable object demonstrating the endosseous part as well as the suprabony part, e.g., a dental prosthetic crown.
Figure 15H:
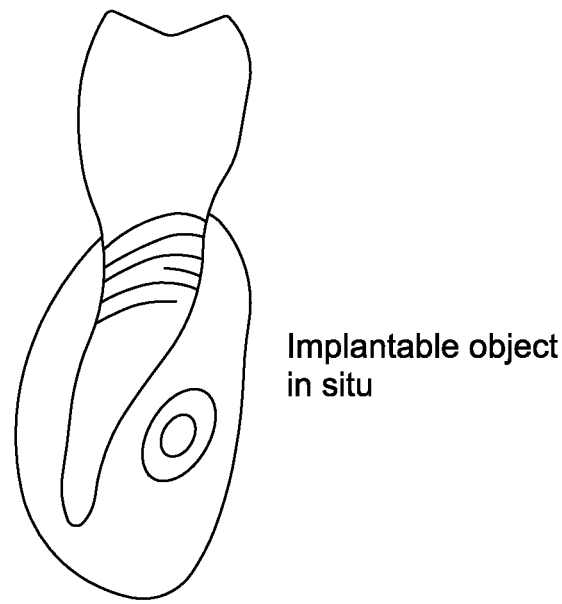
FIGS. 15H-15I illustrate views of the implantable object in situ at the recipient site (FIG. 15H), demonstrating the layer of bone-implantable material (e.g., adhesive composition) retaining it to the recipient site (FIG. 15I).
Figure 15I:
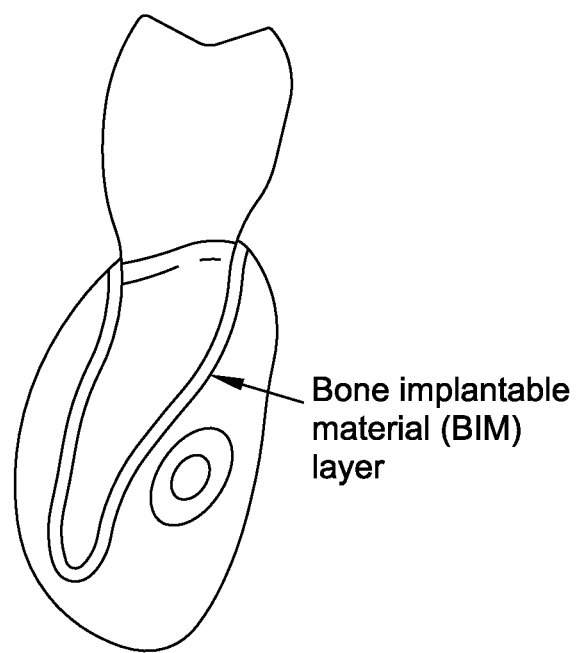

In some embodiments, the implantable object is placed at the implantation site (e.g., into bone, or onto or in between bone surfaces). In some embodiments, the implantable object is implanted fully into bone (e.g., the entire surface of the implantable object is submerged into bone). In some embodiments, the implantable object is implanted at least partially into bone. In some embodiments, the implantable object is implanted into bone and a portion of it extends transdermally. In some embodiments, the implantable object possesses a "platform-switching" transition zone between the endosseous and transdermal portions as shown in FIG. 14A. The broader endosseous part of the implantable object mechanically engages the bone with the optional use of a bone-implantable material (e.g., adhesive composition), while the narrower superficial part emerges transdermally for an attachment to a prosthesis. The transition zone provides a favorable contour for soft tissue cuff attachment, easing cleaning. In some embodiments, the geometry of the endosseous-transdermal implantable object allows for a diminished thickness of the bone-implantable material (e.g., adhesive composition) at the seal zone by the means of a small widening of the transition zone surface as compared to the endosseous portion of the implantable object body diameter as shown in FIG. 14B. Such a feature would provide a positive seat for the implantable object against a flat surface of the bone stump and limit the thickness of the adhesive composition grout seam. In some embodiments, the geometry of the endosseous-transdermal implantable object allows for a diminished thickness of the bone-implantable material (e.g., adhesive composition) at the seal zone by the means of a taper, a conic frustum surface to accomplish the diminution of the film thickness on seating in disproportion to the gap around the endosseous portion of the implantable object body proper as shown in FIG. 14C. In some embodiments, the implantable object is implanted at least partially into bone and comprises an element (e.g., reference element, retention element, orientation element) remaining outside the bone. In some embodiments, the element of the implantable object that remains outside the bone allows physical contact with a device (e.g., a guiding device (e.g., a form, a mold, a guide, a positioning aid), restorative device, a prosthetic device, an instrument). In some embodiments, the element of the implantable object that remains outside the bone engages with (e.g., attaches to or retains) a guiding device or another device (e.g., mechanically, magnetically, or otherwise physically).

In some embodiments, the element (e.g., reference element, retention element, orientation element) of the implantable object that remains outside of the bone emerges into the oral cavity. In some embodiments, the element of the implantable object that remains outside of the bone emerges into the oral cavity and engages with (e.g., attaches to or retains) a guiding device or another device (e.g., mechanically, magnetically, or otherwise physically). In some embodiments, the element of the implantable object that remains outside of the bone emerges into the oral cavity and engages with (e.g., attaches to or retains) a guiding device or another device (e.g., mechanically, magnetically, or otherwise physically) and comprises the surface of a partial or full sphere the substance of which is radiopaque.

In some embodiments, the implantable object is implanted into the jaw (e.g., the upper jaw or lower jaw). In some embodiments, the implantable object is implanted into the jaw (e.g., the upper jaw or lower jaw) and comprises an element (e.g., reference element, retention element, orientation element) that allows for physical contact with a guiding device or another device in the oral cavity.

In some embodiments, the implantable object is implanted into the middle ear (e.g., a bone in the middle ear). In some embodiments, the implantable object is implanted in the middle ear (e.g., a bone in the middle ear) and comprises an element (e.g., reference element, retention element, orientation element) that allows for physical contact with a guiding device or another device in the ear.

In some embodiments, the implantable object is implanted into the facial skeleton, the cranium, the spine, the pectoral or the pelvic girdle bones, the long bones of the limbs, the bones of the wrist or the bones of the ankle and comprises an element that allows for unambiguous physical contact with a guiding device or another device within the anatomical region.

In some embodiments, the implantable object comprises a reference element. In some embodiments, the implantable object is used for the purpose of serving as a spatial reference in radiographic images or data.

In some embodiments, the implantable object is used together with another implantable object (e.g., a mini-implant). In some embodiments, one or more implantable objects are used together. In some embodiments, the one or more implantable objects comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more implantable objects. In some embodiments, the one or more implantable objects comprise between 1 and about 2, 1 and about 3, 1 and about 4, 1 and about 5, and 1 and about 6 implantable objects.

In some embodiments, one or more implantable components are used together for the purpose of serving as a spatial reference in radiographic images. In some embodiments, one or more, two or more, or three or more implantable components are used together or with an anatomic reference element (e.g. a calcified feature (e.g. a tooth, a bone surface)) for the purpose of serving as a spatial reference in radiographic data. In some embodiments, one or more implantable components are used together or with an anatomic reference element for the purpose of serving as a spatial reference in the construction of virtual models (e.g., virtual models of tissues). In some embodiments, one or more implantable components are used together or with an anatomic reference element for the purpose of serving as a spatial reference in the construction of physical models (e.g., physical models of tissues, organs, or lesions). In some embodiments, one or more implantable components are used together or with an anatomic reference element for the purpose of serving as a spatial reference in the design and construction of devices (e.g., guiding devices, implantable objects, instruments for recipient site preparation) fitted to the tissues recorded by radiographic means.

In some embodiments, the present disclosure features methods of using the records produced by observing and recording the positions of said elements (e.g., reference elements) of the implantable components to construct physical and/or virtual models of the tissues in proximity to the markers. In some embodiments, the use of the reference elements of the implantable components results in greater precision in the course of planning and execution of treatment based on scanned (e.g., CT, optical, MRI) anatomical structures (e.g., patient structures, casts, impressions, implantable objects) from numerous or different acquisition sources, as they can be spatially cross-referenced (e.g., indexed) and digitally integrated into one output.

In some embodiments, the models constructed from data, such as the placement of the reference element of the implantable component, are used to construct a spatial reference framework. In some embodiments, the spatial reference framework is then used for precise planning of surgical procedures, implantable object placements, dental reconstructions, oncological irradiation protocols, resection or ablation of brain regions, reconstructive procedures and other applications. This reference framework is capable of relating devices (e.g., a guiding device (e.g., a form, a mold, a guide, a positioning aid), restorative device, a prosthetic device, an instrument) in all three translational degrees of freedom as well as all three rotational degrees of freedom. This means that the placement of devices can be indexed precisely in the axis of rotation corresponding to their long axis. That in turn allows for preplanning of the geometry (e.g., rotation, length, diameter) of devices attached to them. This also means that the paths of action of the recipient site preparation instruments can be programmed with much improved precision when they are attached to the elements (i.e., orientation elements, retentive elements) physically available on the implantable components used in the development of the reference framework. In the dental case, it means that single crowns can be fabricated without a separate visit for impression. In the case of artificial hip joint prosthetic device placement, it means that the length and rotation of the leg can be preplanned and controlled more precisely.

The same reference elements of the implantable components used in the data collection and model construction might also serve in their physical form as the orientation and retentive elements of the guiding device holding the implantable objects or instruments with a high degree of precision. The value of this system also lies in the ability to cross-reference optical (e.g., three-dimensional optical scans), radiographic (e.g., CAT and CBCT scans, with and without contrast, PET scans, etc.), magnetic resonance (e.g., functional MRI), or physical (e.g., casts) records, as needed, and physical attachment in an easily repeatable and precise fashion for clinical use even in the absence of hard tissues available at the surface for reference in the clinical situation.

In some embodiments, the spatial framework is not used solely to relate an implantable object to a particular site but to guide placement and action of instruments, devices, or materials during non-implantation procedures (e.g., biopsy, resection, ablation, oncologic irradiation, etc.).

In some embodiments, the implantable object is implanted without an osteotomy procedure. In some embodiments, the implantable object is implanted following an osteotomy procedure. In either case, the implantable object may be placed into the host site, stabilized, and retained through the use of a bone-implantable material (e.g., an adhesive composition). In some embodiments, the bone-implantable material (e.g., an adhesive composition) is added into the implantation site prior to placement of the implantable object. In some embodiments, the bone-implantable material (e.g., an adhesive composition) is added into the implantation site after placement of the implantable object. In some embodiments, the bone-implantable material (e.g., an adhesive composition) is added into the implantation site at various times during the implantation process, e.g., prior to or after placement of the implantable object. In some embodiments, a bone-implantable material (e.g., an adhesive composition) is added into the implantation site by application to the implantable object prior to its placement at the implantation site. In some embodiments, the bone-implantable material (e.g., an adhesive composition) is added into the implantation site by injection through the implantable object. In some embodiments, the bone-implantable material (e.g., an adhesive composition) is added into the implantation site by injection through a guiding device attached to the implantable object.

Once inserted into the recipient site, the implantable object may exhibit primary stability due to the press fit retention or due to the presence of a bone-implantable material (e.g., an adhesive composition). The bone-implantable material (e.g., an adhesive composition) may retain the implantable object and/or fill the void or voids which exist between the form of the implantable object and the walls of the surrounding bone after the osteotomy is completed. In some embodiments, the combination of an implantable object that fits the natural shapes of the bone contours and the bone-implantable material (e.g., an adhesive composition) eliminates the need for drilling the bone to obtain a particular (e.g., rotationally symmetrical) implant bed shape. In some embodiments, the combination of an implantable object that fits the natural shapes of the bone contours and a bone-implantable material (e.g., an adhesive composition) eliminates the need for impacting the prosthesis into the bone with excessive force, which may be detrimental to the subject (e.g., an osteoporotic subject). The application of these processes would be beneficial in any endosseous implant site whether intraoral and transmucosal, extraoral and transdermal, or deep within the connective tissue compartment (e.g., with prosthetic joint retention application). Those practiced in the art might find other contexts for implant stabilization using implantable objects or the preparation process described in this disclosure.

Figure 11:
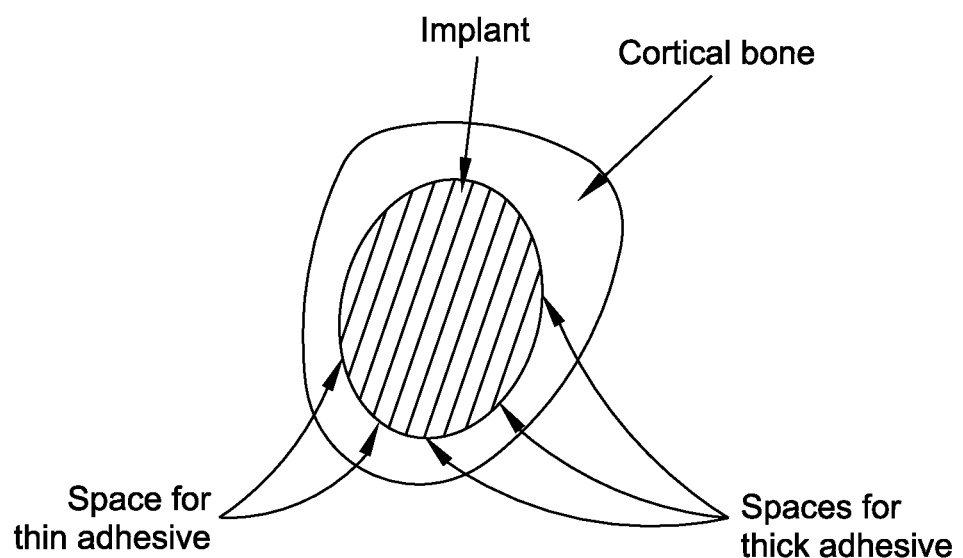
FIG. 11 illustrates in a cross-sectional schematic view the seating of an implantable object in the medullary space of a long bone comprising features providing a broadly distributed variation in the thickness of the bone-implantable material, (e.g., adhesive composition) between the implant surface and the contacting bone surface.

The quantity or the thickness of the layer of a bone-implantable material (e.g., adhesive composition) required to set and/or stabilize an implantable object may vary. The implantable object shape might comprise design features allowing for variation in the thickness of the bone-implantable material (e.g., an adhesive composition) between the recipient bone surface and the implantable object surface as shown in FIG. 11. The features (e.g., longitudinal, transverse, or spiral grooves and ridges) might vary the bone-implantable material (e.g., an adhesive composition) thickness by about 0.01 to 0.1 mm, by about 0.1 mm to 0.3 mm, by about 0.3 mm to 0.5 mm, by about 0.5 mm to 0.8 mm, by about 0.8 mm to 1.2 mm, by about 1.2 mm to 1.5 mm, by about 1.5 mm to 2.0 mm thickness, by about 2.0 mm to 2.5 mm, by about 2.5 mm to 3.0 mm, and/or by more than 3.0 mm. The purpose of such to is to provide for a more gradual transition of mechanical properties during the resorption and replacement process between the bone-implantable material (e.g., adhesive composition)-only contact to bone and ankylosis, i.e., to enhance secondary stability.

The elimination of the rotary instrument preparation as the only practical choice for preparing the recipient site allows for non-rotating, i.e., not rotationally symmetric, implantable object shapes to be employed resulting in greater resistance to torques and consequently lowering the risk of loosening. This factor might be of some consequence in improving the secondary implant stability, particularly concerning rotation about the long axis of the implant, in amputation stump prostheses, for example.

The methods described herein may be used to replace or restore a bone or a segment of bone with an implantable object and/or a bone-implantable material. A bone or segment of bone to be replaced or restored may be present in a subject. In some embodiments, the subject has a disease, e.g., a bone disorder or disease. Exemplary bone diseases or disorders include bone tissue malignancy (e.g., osteosarcoma), malignancy of tissues associated with the bone (e.g., multiple myeloma), distant malignancy metastasized to a bone, osteoporosis, rickets, osteogenesis imperfecta, Paget's disease of the bone, fibrous dysplasia, hearing loss, renal osteodystrophy, infection of the bone, severe and handicapping malocclusion, osteonecrosis, or other genetic, developmental or degenerative disease. In some embodiments, the implantable object is used to prevent or treat a defect in a subject, e.g., caused by a disease or condition, such as cancer (e.g., osteosarcoma), osteoporosis, rickets, osteogenesis imperfecta, Paget's disease of the bone, hearing loss, renal osteodystrophy, a malignancy of the bone, infection of the bone, or other genetic, developmental or degenerative disease. In some embodiments, the subject has experienced a trauma, such as a broken bone, fractured bone, or damaged tooth relating to a disease or condition, such as cancer (e.g., osteosarcoma), osteoporosis, rickets, osteogenesis imperfecta, Paget's disease of the bone, hearing loss, renal osteodystrophy, a malignancy of the bone, infection of the bone, or other genetic or developmental disease.

The methods described herein may be used to treat a subject suffering from or afflicted with any disease or condition that impacts the structural integrity of the bony skeleton with an implantable object or bone-implantable material. In some embodiments, the subject is a child. In some embodiments, the subject is an adult. In some embodiments, the subject is a senior (e.g., an adult over the age of about 50, about 55, about 60, about 65, about 70, about 75, about 80) or in a decline of the skeletal state. In some embodiments, the subject is a human or a non-human animal.

The method described herein may be used to fill a recent extraction socket, resection or amputation site where a physical cavity is present, in fine trabecular bone which might be relatively easily shaped, e.g., maxillary tuberosity, or an area of denser bone which might be first instrumented with bone cutting instruments to provide preliminary shaping, e.g., drills, to initiate a cavity which is then refined with the recipient site preparation instrument to the desired shape.

In some embodiments, soft tissue membranes, attached soft tissue remnants or cartilage may be present at the recipient site. These materials might form a barrier to the adhesive attachment of the implantable object with the bone-implantable material (e.g., adhesive composition) to the bone and thus should be substantially removed prior to the implantable object insertion, thus allowing for increased stabilization and improved osseointegration to occur. The removal of attached soft tissues or cartilage might be considered a part of the recipient site preparation, particularly indicated when no cutting or abrasion of the bone at the implantation site (e.g., into bone, or onto or in between bone surfaces) is required. In the eposteal implantable object placement context, removal of attached soft tissues may comprise stripping or reflection of the periosteum, or removal of ligament or tendon insertions from the implantable object recipient site bone surface. In the post-extraction context removal of attached soft tissues may comprise removal of the periodontal ligament remnants from the alveolus at the host site. In the spine fusion context, the removal of the disk or articular cartilage from the facet joints should be substantial to accomplish an adhesive bond with a bone-implantable material.

In some embodiments, removal of the soft tissue remnants is accomplished by hand curettage or mechanically. In the case of hand curettage, an appropriately sized and shaped hand instrument with a sharp edge might be used to dislodge the soft tissues off bone surface. In the case of mechanical removal, a recipient site preparation instrument with a vibrating tip, e.g., of an ultrasonic, sonic or subsonic frequency, may be used, equipped with an appropriately sized and shaped head. The head might have one or more cutting edges or might comprise appropriately sized abrasive surface elements. Soft tissue membranes and attached soft tissues not interfering with the adhesive wetting of the recipient site bone may be maintained as they may be beneficial, e.g., confine the bone-implantable material (e.g., adhesive composition) to the implantation site (e.g., into bone, or onto or in between bone surfaces), accelerate healing, be the source of beneficial progenitor cells (e.g., stem cells, osteoblasts) etc.

In certain embodiments, the form of the implantable object is undersized compared to the shape matching implantation site (e.g., into bone, or onto or in between bone surfaces) preparation. In these instances, the method described herein may be used to fill the gap space or interface with a bone-implantable material (e.g., adhesive composition) to provide primary fixation upon cure. The bone-implantable material (e.g., adhesive composition) may be used to fill gaps within the structure of the local marrow spaces of the cancellous bone in efforts to augment the local bone density and enhance the fixation strength of the shape matching implantable object to bone.

In some embodiments, the method of placing an implantable object (e.g., an endosseous implant) at its implantation site (e.g., into bone, or onto or in between bone surfaces) comprises the following steps: (a) preparing the implantation site (e.g., into bone, or onto or in between bone surfaces) to receive the implantable object; (b) optionally applying the bone-implantable material (e.g., adhesive composition) to the bone, to the implantable object or to both; (c) inserting the implantable object into implantation site (e.g., into bone, or onto or in between bone surfaces) in the desired orientation; and (d) allowing the bone-implantable material (e.g., adhesive composition) to cure. In some embodiments, the method further comprises stripping soft issue, e.g., periodontal ligament, granulation tissue, or cyst lining, and/or shaping the bone with the recipient site preparation instrument prior to or after application of the bone-implantable material (e.g., adhesive composition).

In some embodiments, the method of placing an implantable object (e.g., an eposteal implant) on the surface of a bone (e.g., external surface of a bone) comprises the following steps: (a) stripping or reflecting the periosteum off the external bone surface at a desired location; (b) applying a bone-implantable material (e.g., adhesive composition) to the bare bone; (c) placing the implantable object in contact with the bone-implantable material (e.g., adhesive composition) and the bone in the desired orientation and location; (d) optionally inserting one or more implantable objects; and (e) allowing the bone-implantable material (e.g., adhesive composition) to cure.

In some embodiments, the method of placing an implantable object (e.g., an eposteal implant) on the surface of a bone (e.g., external surface of a bone) comprises the following steps: (a) stripping or reflecting the periosteum off the external bone surface at a desired location; (b) applying bone-implantable material (e.g., adhesive composition) to the stripped bone; (c) placing the implantable object in contact with the bone-implantable material (e.g., adhesive composition) and the bone in the desired orientation and location; (d) optionally inserting one or more implantable objects; and (e) allowing the bone-implantable material (e.g., adhesive composition) to cure. Application of the bone-implantable material (e.g., adhesive composition) may be achieved through any means, e.g., spreading or injecting. In some embodiments, step (e) may occur at several points during the implantation procedure, including before or after step (c) or before or after step (d).

In some embodiments, the recipient site preparation instrument may be operated by a person (e.g., a skilled operator). In some embodiments, the recipient site preparation instrument may be operated through robotic means or via a navigated procedure. If operated through robotic means, the navigation may be, e.g., remote or guided by telemetry data, strain gauge data, optical data, radiographic data, or by direct human observation. In some embodiments, the recipient site preparation instrument may be preprogrammed or guided by actions determined contemporaneously. In some embodiments, the use of the recipient site preparation instrument may comprise a guiding device.

In some embodiments, any or all of the implantable objects or recipient site preparation instruments is custom produced, wholly or in part, for the individual situation and individual patient. Each of these components may be produced by 3-D printing methods, sintering of powders, milling by cutting instruments or abrasives, electrochemical milling, firing of ceramics, abrasion by slurry or powder streams or a combination of these and other methods of fabrication.

The surface of the implantable object might comprise varied surface types, e.g., machined, polished, etched, blasted with abrasive, porous, microporous, etc., on a single device. The purpose of these features might include improved healing kinetics, improved bone attachment and stress distribution of the deep parts, improved soft tissue attachment near the neck, improved cleansability of superficial parts, improved retention of an attached prosthesis, etc. The guiding device, implantable object, the recipient site preparation instrument, and optionally the bone-implantable material (e.g., adhesive composition) might be packaged as a set for the convenience of the surgeon, e.g., as a kit. The guiding device, implantable object, and the recipient site preparation instrument might be custom fabricated as a set through such means as three dimensional printing, with processing, e.g., hardening, abrasive application, etching, blasting, heat treatment, surface nitride deposition, etc., to be performed on the various parts of the two devices prior to packaging of the matched kit.

EXAMPLES

Some embodiments presented herein are further described in detail by reference to the following examples. These examples are provided for purposes of illustration and are not intended to be limiting unless otherwise specified. The disclosure should be construed to encompass any and all variations which become evident as a result of the teaching provided herein.

Without further description, it is believed that one of ordinary skill in the art can, using the preceding description and the following illustrative examples, make and utilize the compounds and practice the claimed methods. The following examples specifically point out various aspects of the disclosure, and are not to be construed as limiting in any way the remainder of the disclosure.

Example 1: Bone Implantable Materials

Composition BA is a bone-implantable material (BIM) comprising a multivalent metal (e.g., tetracalcium phosphate), an acidic compound (e.g., phosphoserine), and an aqueous medium. Composition BA is a bone-adhesive, osteoconductive, and biodegradable material capable of becoming a substantially size- and form-preserving solid after application and curing.

Example 2: Guide for Shaping of Bone Implantable Material (BIM)

Guiding Device A is a mold relating to a bone site in a geometrically defined manner and possessing desirable form for shaping a bone implantable material, BIM, (e.g., Composition BA) as it cures.
Method of Use:
1. Guiding Device A is (surgically) introduced to the site of action
2. BIM is applied to the space between bone surface and Guiding Device A (e.g., injected through an opening in Guiding Device A, loaded into the Guiding Device A prior to its placement at the site of implantation, loaded into the site of implantation prior to the placement of the Guiding Device A).
3. BIM is allowed to set while in the space defined (e.g., delimited) by Guiding Device A and the bone surface.
4. Guiding Device A is separated from the formed and hardened BIM and removed intraoperatively (or left in situ and biodegraded over time subsequent to the surgery).
5. The resulting composite bone-BIM volume is greater than original bone volume and possesses desired form.
6. BIM, e.g., Composition BA, is replaced by bone tissue substance through biodegradation and/or resorption and/or remodeling over time.
7. An augmented bone volume is the result of the procedure.

Example 3: Guiding Device for Placing Implants

Guiding Device B is a guide (i.e., a positioner) fabricated to be capable of relating to a bone site in a substantially immobile geometrically defined manner and be retained by one or several Implantable Components IC, which are substantially immobile, in a geometrically defined manner by reversible means. The ICs are intended to be attached to the bone at a specific site and in a specific orientation, and then to remain at the site (e.g., as indwelling reference points for radiography, points of physical attachment through retention elements, etc.). BIM is a bone-implantable material (e.g., Composition BA).
Method of Use:
1. One, or several, ICs are attached to the Bridging Component of the Guiding Device B to form the complete Guiding Device B.
2. Guiding Device B is then surgically introduced to the site of action.
3. BIM is applied to contact both the bone surface and ICs, contacting or enclosing parts of ICs and filling voids or gaps between the bone surface and ICs.
4. As BIM is allowed to set, the ICs are attached to bone.
5. Parts of Guiding Device B, including the Bridging Component, might be removed intraoperatively, allowed to biodegrade, or remain indefinitely.
6. BIM is degraded, resorbed and replaced by bone tissue, maintaining the attachment of the IOs to bone in their predetermined locations and orientations.
7. ICs remain attached postoperatively as points of attachment through their retention elements or spatial references through their reference elements for future treatment or diagnostic procedures, as needed.

Example 4: Guiding Device for Placing Implants

The Bridging Component of the Guiding Device C is a guide fabricated to be capable of relating to a bone site in a substantially immobile, geometrically defined manner and retaining one or several Implantable Objects IO, substantially immobile in a geometrically defined manner, by reversible means. Implantable Object IO is intended to be precisely attached to an implantation site (e.g., into bone, or onto or in between bone surfaces) and in a specific orientation relative the three translational dimensions and the three rotational axes and then to remain indwelling (e.g., prosthetic joint element, dental implant, attachment for limb amputation prosthesis, etc.). BIM is a bone-implantable material (e.g., Composition BA).
Method of Use:
1. An IO, or several, is attached to the Bridging Component of the Guiding Device C.
2. Guiding Device C is (surgically) introduced to the site of action in a desired relationship to the bone.
3. BIM is applied to contact bone surface and IO, enclosing parts of IO and filling voids or gaps between the bone surface and IO. The application of BIM may precede, be concurrent, or be subsequent to step 2.
4. IO is adhesively attached to bone as BIM is allowed to set or cure.
5. Guiding Device C is removed intraoperatively.
6. The implantable object IO, or several, remains in situ to function as BIM is degraded and replaced with bone over time.

Example 5: Custom Multicomponent Implantable Guiding Device for Placing Implants Guiding Device D is a guide fabricated to be capable of the following: a.) relating to a bone site in a substantially immobile, geometrically defined manner, b.) being retained by one or several of its Implantable Components IC, substantially immobile, in a geometrically defined manner by reversible means, and c.) retaining one or several Implantable Objects IO, substantially immobile in a geometrically defined manner by reversible means. Implantable Components ICs of Guiding Device D, are intended to be attached to bone at one to several sites marginal to the area of interest and may or may not be intended to be indwelling, depending on the application. One, or several, Implantable Objects IO is intended to be precisely attached to the bone at a specific site and in a specific orientation relative the three translational dimensions and the three rotational axes and then to remain indwelling (e.g., prosthetic joint element, dental implant, attachment for limb amputation prosthesis, etc.). BIM is a bone-implantable material (e.g., Composition BA).
Method of Use:
1. Several Implantable Components IC are attached to the bone in the area of interest, either by adhesion, e.g., with Composition BA, by a screw feature, by both, or by any similar means.

2. Records (e.g., radiographic scan, optical scan) relating the precise positions and orientations of the IC reference elements in relation to the bone and each other are collected.
3. The information in the records is used to develop a three-dimensional spatial model M, virtual or physical, of the area of interest, including the locations and orientations of the reference elements of the ICs.
4. The physical Bridging Component of the Guiding Device D is fabricated (e.g., by CAD/CAM milling) from model M to be capable of a.) Unambiguously and simultaneously attaching to several of the ICs present (preferably at least three, possibly all), by reversible means and b.) Retaining one or more Implantable Objects IO in a substantially immobile, geometrically defined preplanned manner by reversible means. One or several versions of the Guiding Device D may be fabricated for various applications.
5. One, or several IOs, are attached, by means of the retention elements to the Guiding Device D in a preplanned relationship with Guiding Device D, the reference elements for the ICs, and each other in a substantially immobile fashion.
6. The assembled Guiding Device D, together with the attached IO or IOs, is attached by the means of the retention elements to the ICs placing them in the pre-planned relationship with the bone.
7. BIM is applied to the implantation site, (e.g., the bone surface, the IO surface, or the space between bone surface and the Implantable Object IO). The application of BIM may precede, be concurrent, or be subsequent to step 6.
8. As BIM is allowed to set, e.g., harden or cure, the one or several Implantable Objects is adhesively attached to the bone in the pre-planned position and orientation allowed.
9. Parts of Guiding Device D, e.g., the Bridging Component, are removed intraoperatively, with the Implantable Components IC either removed or remaining as needed.
10. Implantable Object(s) IO remain(s) in situ to function as the BIM is progressively degraded, resorbed and replaced by bone tissue.

Example 6: Custom Guiding Device for Precise Positioning and Adhering or Luting Implantable Objects Guiding Device E is a positioning guide fabricated to be capable of the following: a.) Relating to a bone site in a substantially immobile, geometrically defined manner, b.) Be retained by one or several of its Implantable Components ICs, in a substantially immobile, geometrically defined manner by reversible means, and c.) Retaining one, or several, Instruments in a stable geometrically defined manner by reversible means. The Implantable Components ICs of Guiding Device E, are intended to be attached to bone at one to several sites marginal to the area of interest and may or may not be intended to be indwelling, depending on the application. The retention elements of Implantable Components IC might be submerged in the connective tissue compartment might be transdermal or might be transmucosal in their location, depending on the application (e.g., oral, cranial, or hip prosthesis). One or several instruments can be attached to the Guiding Device E and used to affect the surrounding tissues by any of the following, or other, means: a.) cutting (e.g., with a blade, drill, abrasive, etc.; b.) cutting or ablating with concentrated energy (e.g., laser, electrosurgery, etc.); c.) releasing heat; d.) releasing a substance; e.) applying electric charge or current (e.g., neurostimulation); f.) or by any other means. BIM is a bone-implantable material (e.g., Composition BA).

Method of Use:
1. Several Implantable Components IC are attached to the bone in the area of interest, either by adhesion with BIM or by a screw feature, both, or similar means.
2. Records (e.g., radiographic, optical, magnetic resonance) relating the precise positions of the ICs in relation to the bone, each other, and to characteristics of interest (e.g., presence of neoplasm, specific brain activity, morphology of tissues (e.g., ear ossicles, facial bones or cartilages), etc.) are collected.
3. The records are used to develop three-dimensional spatial model M of the area of interest, including the IC locations and attributes of interest.
4. The Bridging Component of the Guiding Device E is fabricated from the model M to be capable of the following: a.) Unambiguously and simultaneously being retained by the retentive elements of the Implantable Components IC present, by reversible means and b.) Retaining any Instrument I in a stable geometrically defined pre-planned manner.
5. Guiding Device E is assembled by engagement of the retention elements to Implantable Components IC in situ.
6. Instrument I is attached to Guiding Device E in the planned relationship with the bone either prior to, concurrently, or following step 5.
7. BIM may be applied in contact with the surface of bone, Guiding Device E, and Instrument I to stabilize the attachment. Alternatively, or in addition, the attachment between Guiding Device E, its component IC, and the Instrument I may be mechanically secured or locked through retention elements.
8. Instrument I is used to affect the tissues through its action.
9. Parts of Guiding Device E, e.g., the Bridging Component, and Instrument I are removed. Alternatively, parts of Guiding Device E and/or Instrument I may remain in situ after closure of the access.
10. Parts of Guiding Device E and Instrument I might electively be reattached for repetition of the procedure, depending on the application (e.g., oncological irradiation, brain stimulation, brain activity monitoring, etc.).
11. Implantable Components IC might remain in situ indefinitely, remain in situ to be degraded or resorbed, or removed after the procedure is completed. The remainder of Guiding Device E may be removed.

Example 7: Implantable Multicomponent Guiding Device for Multiple Instruments and Implant Placements Guiding Device F is a positioning guide comprising a Bridging Component fabricated to be capable of the following: a.) Relating to a bone site in a substantially immobile, geometrically defined manner, b.) Be retained by one or several Implantable Components IC, in a substantially immobile, geometrically defined manner by reversible means, and c.) Retaining one, or several, Instruments in a stable geometrically defined manner by reversible means, d.) Retaining several types of implantable devices, e.g., Implantable Components IC and Implantable Objects IO. One or several Instruments can be attached to the Guiding Device F, e.g., by attaching to the Bridging Component, and used to affect the surrounding tissues by any of the following, or other, means: a.) cutting (e.g., with a blade, drill, trephine, saw, abrasive, etc.) or b.) releasing a substance, e.g., injecting BIM. BIM is a bone-implantable material (e.g., Composition BA. The Implantable Components IC, of Guiding Device F, are intended to be attached to bone at one to several sites marginal to the area of interest and may or may not be intended to be indwelling, depending on the application. The retention elements of Implantable Components IC might be submerged in the connective tissue compartment, might be transdermal, or might be transmucosal in their location, depending on the application (e.g., oral, cranial, or hip prosthesis). Implantable Objects IO, e.g., dental implants, dental implants with prosthetic abutments attached, dental implants with prosthesis attached, an acetabular cup prosthesis, an endosseous amputation limb prosthesis attachment, etc.) are intended to be precisely attached to the bone at a specific site and in a specific orientation relative the three translational dimensions and the three rotational axes and then to remain indwelling (e.g., prosthetic joint element, dental implant, attachment for limb amputation prosthesis, etc.).

Method of Use:
1. One or several Several Implantable Components IC are attached to the bone in the area of interest, either by adhesion with BIM or by a screw feature, both, or similar means.
2. Records (e.g., radiographic, optical, etc.) relating the precise positions of the ICs in relation to the bone, other tissues (e.g., teeth), dental implants, dental restorations, etc.) and each other are collected.
3. The records are used to develop three-dimensional spatial model M of the area of interest, including the IC locations and structures of interest.
4. The Bridging Component (or several, serving distinct functions, e.g., retaining different instruments, Implantable Objects), of the Guiding Device F is fabricated from the model M to be capable the following: a.) Unambiguously and simultaneously being retained by the retentive elements of the Implantable Components IC present, by reversible means, b.) Retaining any Instrument I (e.g., RSP Instrument, BIM injection Instrument, etc.) in a stable geometrically defined pre-planned manner, and c.) Retaining or accommodating Implantable Objects IO, directly or indirectly, in a stable and reversible manner.
5. Guiding Device F is assembled by attachment through retention elements to Implantable Components IC.
6. Instrument Ia, e.g., a soft tissue cutting instrument (e.g., a punch) is attached to Guiding Device F. This step may precede or follow step 5.
7. Instrument Ia is used (e.g., to uncover the bone tissue) at one or more implantation sites.
8. Instrument Ia is removed from the Device F or the Bridging Component is removed with Instrument Ia and a different Bridging Component of Device F is attached to the Implantable Components IC.
9. Instrument Ib, e.g., a hard tissue cutting instrument (e.g., a drill, RSP Instrument, or other) is attached to Guiding Device F.
10. Instrument Ib is used (e.g., to initiate the preparation of the recipient site, to initiate the preparation of the recipient site, to complete the preparation of the recipient site, etc.) at one or more implantation sites.
11. Instrument Ib is removed from the Device F or the Bridging Component is removed with Instrument Ib and a different Bridging Component of Device F is attached to the Implantable Components IC.
12. Instrument Ic, e.g., syringe for injection of the BIM, is attached to Guiding Device F.
13. Instrument Ic is used (e.g., apply the BIM at the recipient site) at one or more implantation sites.
14. Instrument Ic is removed from the Device F or the Bridging Component is removed with Instrument Ic and a different Bridging Component of Device F is attached to the Implantable Components IC
15. Steps 6-14 may be repeated with different instruments and at different sites, as needed.
16. Implantable Object IO, or several, is attached in a preplanned relationship to a Bridging Component of Guiding Device F (i.e., also in a pre-planned relationship to the bone. (This step may precede, be contemporaneous with, or follow steps 5 through 15.)
17. Device F, retaining at least one Implantable Objects IO is assembled once again by attachment of the Bridging Component to the indwelling Implantable Components IC.
18. BIM is allowed to set (harden, cure, etc.) while retaining Implantable Object IO in the desired pre-planned position, with immediate load bearing retention gained from adhesion with BIM.
19. Steps 16 through 18 may be repeated with several Implantable Objects, as needed.
20. Implantable Object IO might be intended to remain in situ functioning indefinitely (e.g., supporting dental restoration, serving as part of a prosthetic joint, serving as an anchor for a limb prosthesis).
21. Parts of Guiding Device F, e.g., the Bridging Component, might be removed or electively remain in situ, e.g., the Implantable Components IC.
22. BIM is replaced by bone tissue in course of time through biodegradation, resorption, remodeling and creeping substitution.

Example 8: Implantable Instrument Holder

Guiding Device G is a positioning guide comprising a Bridging Component fabricated to be capable of the following: a.) Relating to a bone site in a substantially immobile, geometrically defined manner, b.) Be retained by one or several Implantable Components IC, in a substantially immobile, geometrically defined manner by reversible means, and c.) Retaining one, or several, Instruments in a stable geometrically defined manner by reversible means. The Implantable Components IC of Device G are intended to be attached to bone at one or more sites marginal to the area of interest and may or may not be intended to be indwelling, depending on the application. The retention elements of Implantable Components IC might be transdermal or transmucosal. Instrument I is attached to the Guiding Device and used to affect its surroundings by any of the following, or another means: cutting (e.g., with a blade, drill, abrasive, trephine, saw, etc.; cutting with concentrated energy (e.g., laser, Bovie, etc.); releasing heat; releasing a substance; applying electric current; or by other means. BIM is a bone-implantable material (e.g., Composition BA).

Method of Use:
1. One or several Implantable Components IC are attached to the bone in the area of interest, either by adhesion with BIM or by a screw feature, both, or similar means.
2. Records (e.g., radiographic, optical, magnetic resonance, PET, etc.) relating the precise positions of the ICs in relation to the bone, each other, and to characteristics of interest (presence of neoplasm, brain activity, etc.) are collected
3. The records are used to develop three-dimensional spatial model M of the area of interest, including the IC locations and characteristics of interest
4. The Bridging Component (or several, serving distinct functions, e.g., retaining different instruments), of the Guiding Device G is fabricated from the model M to be capable the following: a.) Unambiguously and simultaneously being retained by the retentive elements of the Implantable Components IC, by reversible means, b.) Retaining any Instrument I, or several instruments, in a stable geometrically defined pre-planned manner.
5. Guiding Device G is assembled by attachment through retention elements to Implantable Components IC.
6. The Instruments (e.g., skin punch, bone drill, electrode holder, irradiation source, thermometer) which might be necessary to perform the procedure can be attached to the Bridging Component, or to several Bridging Components, together, or sequentially. The attachment of the instrument may be stabilized through retention elements of the Implantable Components or the Bridging Components or through the use of an adhesive, e.g., Composition BA.
7. The Instruments attached to the Device G can then be used to affect the substrate tissues, (e.g., osteotomy, ablation, stimulation, cutting, heating, substance deposition) or collect data from the tissues, (e.g., electrical activity, temperature, oxygen saturation, pH).
8. Guiding Device G and Instrument I is removed intraoperatively. Alternatively, Guiding Device G and an Instrument I may remain in situ after closure of the access, as needed.
12. The bridging Component of Guiding Device G and Instrument I might electively be reattached for repetition of the procedure, depending on the application (e.g., oncological irradiation, brain stimulation).
13. Implantable Components IC might remain in situ indefinitely, remain in situ to be degraded or resorbed, or removed after the procedure or procedure series is completed.

Example 9: Recipient Site Preparation and its Shape Matching Injectable Object

One or several RSP Instruments can be used to prepare the recipient site for placement of an implantable object into or onto a bony tissue. The RSP Instrument for this implantable object shape is substantially matched in its three-dimensional shape and size to the implantable object and need not be intended to be rotated (e.g., vibrational motion, reciprocal motion) with its motion generated by magnetostrictive, piezoelectric, electromechanical, magnetic, hydraulic means, or other. Implantable Objects IO, e.g., dental implants, dental implants with prosthetic abutments attached, dental implants with prosthesis attached, an acetabular cup prosthesis, an endosseous amputation limb prosthesis attachment, etc.) with its shape matching contour to the recipient site are intended to be precisely placed to the bone at the recipient site and in a specific orientation relative the three translational dimensions and the three rotational axes and then to remain indwelling (e.g., prosthetic joint element, dental implant, attachment for limb amputation prosthesis, etc.). BIM is a bone-implantable material (e.g., Composition BA). BIM is intended to be placed as a layer between the surface of bone at the recipient site and the IC and serves the function of adhesive attachment after curing.
Method of Use:
1. The RSP Instrument, e.g., shape matching to IO, is use to prepare the recipient site using non-rotational motion, e.g., vibrational or reciprocal, that is generated to effect the implantation site (e.g., to subtract, to impact) in a manner to accept the placement of the shape-matching IO.
2. The shape-matching Implantable Object IO, or several, is inserted into the recipient site and whereby the IO placement is effectively located within the recipient site prepared by the RSP Instrument.
3. Alternatively, BIM is applied to contact both the bone surface of the recipient site and IOs, contacting or enclosing parts of IOs and filling voids or gaps between the bone surface and ICs. (This step may precede, be contemporaneous with, or follow steps 2.)
4. BIM is allowed to set (harden, cure, etc.) while retaining Implantable Object IO in the desired preplanned position, with immediate load bearing retention gained from adhesion with BIM.
5. BIM is degraded, resorbed and replaced by bone tissue, maintaining the attachment of the IOs to bone in their predetermined locations and orientations.

Example 10: Guiding Device for Both Recipient Site Preparation and its Shape Matching Implantable Object Guiding Device H is a positioning guide comprising a Bridging Component fabricated to be capable of the following: a.) Relating to a bone site in a substantially immobile, geometrically defined manner, b.) Alternatively, being retained by one or several Implantable Components IC, in a substantially immobile, geometrically defined manner by reversible means, c.) Retaining one, or several, Recipient Site Preparation (RSP) Instruments and d.) Retaining one, or several, Implantable Objects IO in a substantially immobile, geometrically defined manner by reversible means. One or several RSP Instruments can be attached to the Guiding Device H, e.g., by attaching to the Bridging Component, and used to prepare the recipient site for placement of an implantable object into or onto a bony tissue. The RSP Instrument for this implantable object is substantially matched in its three-dimensional shape and size to the implantable object and needs not to be rotated (e.g., vibrational motion or reciprocal motion is sufficient) with its motion generated by magnetostrictive, piezoelectric, electromechanical, magnetic, hydraulic means, or other. An Implantable Objects IO, e.g., dental implant, dental implant with prosthetic abutment attached, dental implant with prosthesis attached, an acetabular cup prosthesis, an endosseous limb amputation prosthesis attachment, etc.) with its shape matching contour to the recipient site are intended to be precisely placed into or onto the bone at the recipient site and in a specific orientation relative the three translational dimensions and the three rotational axes and then to remain indwelling (e.g., prosthetic joint element, dental implant, attachment for limb amputation prosthesis, etc.). BIM is a bone-implantable material (e.g., Composition BA). BIM is intended to be placed as a layer between the surface of bone at the recipient site and the IO and serve the function of adhesive attachment after curing.

Method of Use:
1. One or several Several Implantable Components IC are attached to the bone in the area of interest, either by adhesion with BIM or by a screw feature, both, or similar means.
2. Records (e.g., radiographic scans, optical scans, etc.) relating the precise positions of the ICs in relation to the bone, other hard tissues (e.g., teeth), the soft tissues (e.g., muscle attachments, skin surface), dental implants, dental restorations, other prostheses, etc.) and each other are collected.
3. The records are used to develop three-dimensional spatial model M of the area of interest, including the IC locations and structures of interest.
4. The Bridging Component (or several, serving distinct functions, e.g., retaining different instruments, Implantable Objects), of the Guiding Device H is fabricated from the model M to be capable the following: a.) Unambiguously and simultaneously being retained by the retentive elements of the Implantable Components IC present, by reversible means, b.) Retaining one, or several, RSP Instruments in a stable geometrically defined pre-planned manner, and c.) Retaining or accommodating Implantable Objects IO, directly or indirectly, in a stable and reversible manner.
5. Guiding Device H is assembled by attachment through retention elements to Implantable Components IC.
6. The RSP Instrument, e.g., shape matching to IO, is attached to Guiding Device H. This step may precede or follow step 5.
7. The non-rotational RSP Instrument motion, e.g., vibrational or reciprocal, is generated to effect the implantation site (e.g., to subtract, to compact) in a manner to accept the placement of the shape-matching IO.
8. The RSP Instrument is removed from the Device H: or the Bridging Component is removed together with the RSP Instrument from the Implantable Components IC of Guiding Device H, and a different Bridging Component of Device H is attached to the Implantable Components IC.
9. The shape-matching Implantable Object IO, or several, is attached and retained in a preplanned relationship to a Bridging Component of Guiding Device H (i.e., also in a pre-planned relationship to the bone) and whereby the IO placement is effectively located within the recipient site prepared by the RSP Instrument.
10. Alternatively, BIM is applied to contact both the bone surface of the recipient site and IOs, contacting or enclosing parts of IOs and filling voids or gaps between the bone surface and ICs. (This step may precede, be contemporaneous with, or follow step 9.)
11. BIM is allowed to set (harden, cure, etc.) while retaining Implantable Object IO in the desired pre-planned position, with immediate load bearing retention gained from adhesion with BIM.
12. Steps 6 through 11 may be repeated with several Implantable Objects, as needed.
13. Parts or all of Guiding Device H, including the Bridging Component, including the Implantable Components, might be removed intraoperatively, allowed to biodegrade, or remain indefinitely.
14. BIM is degraded, resorbed and replaced by bone tissue, maintaining the attachment of the IO, or several IOs, to bone in their predetermined locations and orientations.

Example 11: Guiding Device for Placement of Implantable Object with Capability of Injecting Bone-Implantable Material Guiding Device I is a guide (positioner) fabricated to be capable of the following: a.) Retaining a Implantable Object IO, e.g., interbody cage for spine fusion, in a geometrically defined manner by reversible means, b.) Conducting the flow of a Bone-Implantable Material through a channel within or along the Implantable Object IO, c.) Electively generating hydrostatic pressure, e.g., through the action of a piston, and d.) Electively comprising Implantable Components IC for orientation. Implantable Object IO is intended to be attached to the bone at a specific site and in a specific orientation, and then to remain indwelling (e.g., interbody spinal fusion cage, facet joint fixation device, intertransverse process fixation device). BIM is a bone-implantable material (e.g., Composition BA).

Method of Use:
1. The implantation site is prepared to receive the Implantable Object IO.
2. The Implantable Object IO is attached to the Guiding Device I.
3. The Implantable Object IO is surgically introduced (guided) to the recipient site. One or several Guiding Devices I and Implantable Objects may be used during the procedure.
4. BIM is injected into Guiding Device I through a port. Step 4 may precede, be concurrent, of follow steps 2 and 3.
5. Guiding Device I is used to generate hydrostatic pressure of BIM and to induce its flow into and through or along the Implantable Object IO into the space surrounding Implantable Object IO, e.g. the intervertebral space, facet joint, intertransverse processes. Alternatively BIM is injected into and through Guiding Device I to flow into, through or along Implantable Object OI and into the space surrounding the Implantable Object IO.
6. The Implantable Object IO is adhesively attached to bone as BIM, e.g., Composition BA is allowed to set (cure) and establish fixation.
7. Guiding Device I is disengaged from Implantable Object IO and removed from the operative field prior to closure.
8. The Implantable Object IO remains indwelling as BIM is degraded, resorbed and replaced by bone tissue (e.g., to effect interbody spinal fusion, facet joint fusion, or postero-lateral fusion).

Example 12: One Device Serving Both as an RSP Instrument and the Implantable Object Device K possesses the attributes required of the RSP instrument bone-contacting element, e.g., stable attachment to the motive element, sufficient strength to withstand expected loads, surface and bulk characteristics required to affect the recipient site in a desirable manner, but also possesses the attributes required of an implantable object, e.g., long term compatibility with the tissues, sufficient strength to withstand expected loads, features needed for attachment of prosthetic parts, BIM is a bone-implantable material (e.g., Composition BA).

Method of Use:
1. The Recipient Site Preparation for the implantation of an Implantable Object is nearing completion, i.e., the bony is site is nearly shaped to the desired form to receive the Implantable Object, i.e., Device J.
2. An RSP instrument bone-contacting element, i.e., Device J, is mounted on the motive element, e.g., the actuator,
3. The RSP instrument is used to modify the recipient site, e.g., by abrasion. chipping, cutting, compacting, etc., of the bone at the site to a desired state, e.g., completion of the site preparation.
4. Device J is removed with the motive element of the RSP instrument and is separated from it away from the recipient site.
5. BIM is applied to the recipient site or the Device J, i.e., the Implantable Object.
6. The Device J, i.e. the Implantable Object, is seated in the desired location and orientation within the recipient site.
7. BIM is degraded, resorbed and replaced by bone tissue, maintaining the attachment of the IO, or several IOs, to bone in their predetermined locations and orientations.

Example 13: One Device Serving Both as an RSP Instrument and the Implantable Object Device K possesses the attributes required of the RSP instrument bone-contacting element, e.g., stable attachment to the motive element, sufficient strength to withstand expected loads, surface and bulk characteristics required to affect the recipient site in a desirable manner, but also possesses the attributes required of an implantable object, e.g., long term compatibility with the tissues, sufficient strength to withstand expected loads, features needed for attachment of prosthetic parts.

Method of Use:
1. The Recipient Site Preparation for the implantation of an Implantable Object is near completion, i.e., the bony site is nearly shaped to the desired form to receive the Implantable Object, i.e., Device K.
2. An RSP instrument bone-contacting element (i.e., Device K) is mounted on the motive element, e.g., the actuator.
3. The RSP instrument is used to modify the recipient site, e.g., by abrasion. chipping, cutting, compacting, etc., of the bone at the site to a desired state, e.g., completion of the site preparation.
4. The motive element of the RSP instrument is disengaged from Device K without withdrawing Device K from the recipient site.
5. Device K, remains at the recipient site as the Implantable Object, retained by frictional forces.
6. Bone surrounding Device K heals through its natural processes and mechanically integrates with Device K.

INCORPORATION

The disclosures of each and every patent, patent application, and publication cited herein are hereby incorporated herein by reference in their entirety. While this disclosure has been described with reference to specific aspects, it is apparent that other aspects and variations may be devised by others skilled in the art without departing from the true spirit and scope of the disclosure. The appended claims are intended to be construed to include all such aspects and equivalent variations. Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference.

While this disclosure has been particularly shown and described with references to preferred embodiments thereof, it will be understood by those skilled in the art that various changes in form and details may be made therein without departing from the scope of the disclosure encompassed by the appended claims.

We claim:
1. A method of implanting an implantable object in a tooth socket of a subject, the method comprising:
   (a) preparing the tooth socket by substantially removing the periodontal ligament;
   (b) injecting an adhesive composition to the prepared tooth socket; and
   (c) implanting the implantable object into the prepared tooth socket, wherein
      (i) the shape of the implantable object is asymmetrical and matches the size, shape, or other dimension of the tooth socket;
      (ii) the implantable object comprises a changing contour and is substantially free of a thread;
      (iii) the adhesive composition comprises an aqueous medium, a powdered multivalent metal having a mean particle size between 0.005 mm and 0.150 mm, and an acidic compound of Formula (I):

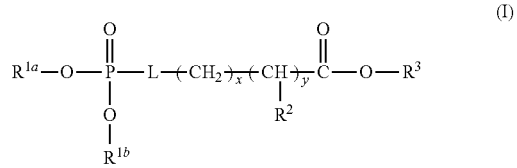

or a pharmaceutically acceptable salt thereof, wherein:
L is O, S, NH, or $CH_2$;
each of $R^{1a}$ and $R^{1b}$ is independently H, optionally substituted alkyl, or optionally substituted aryl;
$R^2$ is H, $NR^{4a}R^{4b}$, $C(O)R^5$, or $C(O)OR^5$;
$R^3$ is H, optionally substituted alkyl, or optionally substituted aryl;
each of $R^{4a}$ and $R^{4a}$ is independently H, $C(O)R^6$, or optionally substituted alkyl;
$R^5$ is H, optionally substituted alkyl, or optionally substituted aryl;
$R^6$ is optionally substituted alkyl or optionally substituted aryl; and
each of x and y is independently 0, 1, 2, or 3;
      (iv) the adhesive composition forms a tacky state after mixing with the aqueous medium;
      (v) the adhesive composition is resorbable; and
      (vi) upon adhering the implantable object to the tooth socket, the implantable object is load bearing.
2. The method of claim 1, wherein the implantable object comprises a bone-engaging element.
3. The method of claim 1, wherein the implantable object is custom produced.
4. The method of claim 1, wherein the implantable object matches the size and/or shape of a tooth root.
5. The method of claim 1, wherein the implantable object is between about 1 mm and about 10 mm in diameter.

6. The method of claim 1, wherein the implantable object comprises a port or opening.

7. The method of claim 1, wherein the implantable object and/or adhesive composition further comprise a naturally occurring polymer or a synthetic polymer.

8. The method of claim 1, wherein the implantable object is configured for partial implantation in the bone.

9. The method of claim 1, wherein the implantable object is configured for implantation fully in the bone.

10. The method of claim 1, wherein placing the implantable object comprises a transition zone between an endosseous portion and a transdermal portion of the implantable object.

11. The method of claim 10, wherein the implantable object comprises a geometry permitting variation in a thickness of the adhesive composition by about 0.8 to 1.2 mm.

12. The method of claim 10, wherein the implantable object comprises a geometry permitting variation in a thickness of the adhesive composition by about 0.1 to 0.3 mm.

13. The method of claim 10, wherein the implantable object comprises a geometry permitting variation in a thickness of the adhesive composition by more than 3.0 mm.

14. The method of claim 1, further comprising using a guiding device in contact with a portion of the implantable object.

15. The method of claim 1, wherein the implantable object is custom designed to be patient specific based on a scan, wherein the scan is one of a CT scan, an optical scan, or an MRI scan.

16. The method of claim 1, wherein the implantable object comprises titanium or one or more ceramics.

17. The method of claim 1, wherein the multivalent metal salt is selected from the group consisting of tetracalcium phosphate and tricalcium phosphate.

18. The method of claim 1, wherein the implantable object has a load-bearing capacity of greater than about 0.5 MPa.

19. The method of claim 1, wherein the adhesive composition further comprises an additive.

* * * * *